US012534487B2

(12) United States Patent
Morrow et al.

(10) Patent No.: US 12,534,487 B2
(45) Date of Patent: *Jan. 27, 2026

(54) COMPOUNDS FOR USE AS IRON(III) MRI CONTRAST AGENTS

(71) Applicant: The Research Foundation for The State University of New York, Buffalo, NY (US)

(72) Inventors: Janet R. Morrow, Williamsville, NY (US); Eric M. Snyder, Williamsville, NY (US); Didar Asik, Buffalo, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 430 days.

This patent is subject to a terminal disclaimer.

(21) Appl. No.: 17/682,695

(22) Filed: Feb. 28, 2022

(65) Prior Publication Data

US 2022/0259244 A1 Aug. 18, 2022

Related U.S. Application Data

(63) Continuation of application No. 16/615,024, filed as application No. PCT/US2018/033759 on May 21, 2018, now Pat. No. 11,261,208.

(60) Provisional application No. 62/508,548, filed on May 19, 2017.

(51) Int. Cl.

| | |
|---|---|
| ***C07F 15/02*** | (2006.01) |
| ***A61K 49/08*** | (2006.01) |
| ***A61K 49/10*** | (2006.01) |
| ***A61K 49/12*** | (2006.01) |
| ***A61K 49/14*** | (2006.01) |

(52) U.S. Cl.
CPC .......... *C07F 15/025* (2013.01); *A61K 49/085* (2013.01); *A61K 49/106* (2013.01); *A61K 49/124* (2013.01); *A61K 49/128* (2013.01); *A61K 49/143* (2013.01)

(58) Field of Classification Search
CPC .. A61K 49/085; A61K 49/106; C07D 255/02; C07F 15/025
See application file for complete search history.

(56) References Cited

U.S. PATENT DOCUMENTS 4,885,363 A 12/1989 Tweedle et al.
11,261,208 B2 * 3/2022 Morrow ............... A61K 49/106
2014/0193344 A1 * 7/2014 Morrow ............... C07D 471/04 540/465
2016/0052894 A1 2/2016 Chong
2016/0228581 A1 8/2016 Morrow et al.

FOREIGN PATENT DOCUMENTS

WO WO-2015038943 A1 * 3/2015 ........... A61K 49/106

OTHER PUBLICATIONS

Lane, B.S., et al., Metal-Catalyzed Epoxidations of Alkenes with Hydrogen Peroxide, Chemical Reviews, May 17, 2003, vol. 103, No. 7, pp. 2457-2573.

Yang, C. et al., Synthesis and Characterization of a Novel Macrocyclic Chelator with 3-Hydroxy-4-Pyrone Chelating Arms and Its Complexes with Medicinally Important Metals, Inorganic Chemistry, Feb. 19, 2008, vol. 47, No. 7, pp. 2719-2727.

Auerbach, U. et al., Synthesis and Coordination Chemistry of the Hexadentate Ligands 1,4,7-Tris(2-hydroxybenzyl)-1,4,7-triazacyclononane (H3L1) and 1,4,7-Tris(3-tert-butyl-2-hydroxybenzyl)-1,4,7-triazacyclononane (H3L2). Crystal Structures of [HL1CuII] and [L2FeIII]acacH, Inorganic Chemistry, Mar. 1990, vol. 29, No. 5, pp. 938-944.

Wieghardt, K. et al., 1,4,7-Triazacyclononane-N,N', N"-triacetate (TCTA), a Hexadentate Ligand for Divalent and Trivalent Metal Ions. Crystal Structures of [CrIII(TCTA)], [FeIII(TCTA)], and Na[CuII(TCTA)]-2NaBr-8H2O, Inorganic Chemistry, 1982, vol. 21, pp. 4308-4314.

Stockheim, C. et al., First-row transition-metal complexes of mixed 'pendant-arm' derivatives of 1,4,7-triazacyclononane containing phenolate and carboxylate functional groups, Journal of The Chemical Society. Dalton Transactions, Jan. 1996, No. 23, pp. 4409-4416.

Gamelin, D.R., et al., Excited-State Contributions to Ground-State Properties of Mixed-Valence Dimers: Spectral and Electronic-Structural Studies of [Fe2(OH)3(tmtacn)2]2+ Related to the [Fe2S2]+ Active Sites of Plant-Type Ferredoxins, Journal of the American Chemical Society, Aug. 28, 1996, vol. 118, Issue 34, pp. 8085-8097.

Shiraishi, K., et al., MRI contrast agents with targeting ability, 2008, Drug Delivery System, vol. 23-1, pp. 33-39.

* cited by examiner

*Primary Examiner* — Michael G. Hartley
*Assistant Examiner* — Jagadishwar R Samala
(74) *Attorney, Agent, or Firm* — Hodgson Russ LLP

(57) ABSTRACT

Provided are macrocyclic compounds and compounds with two or more macrocyclic groups, iron coordinated macrocyclic compounds, and iron coordinated compounds with two or more macrocyclic groups. The iron is high-spin iron(III). The iron coordinated compounds may exhibit a negative redox potential (e.g., relative to a normal hydrogen electrode at a biologically relevant pH, for example, a pH of 6.5-7.5). The compounds can be used as MRI contrast agents.

4 Claims, 23 Drawing Sheets

TOB

TOB

Fe(TOB)(Cl)

TOB

Fe(TOB)Cl

X = $Cl^-$, $CF_3SO_3^-$

| Fe(TACO) | log β | $pK_a$ |
|---|---|---|
| AH | 11.7828 ± 0.08 | 9.97 ± 0.08 |
| $AH_2$ | 18.3565 ± 0.09 | 6.57 ± 0.04 |
| Meglumine | | |
| MH | 9.9685 ± 0.0134 | 9.9685 ± 0.0134 |
| $MH_2$ | 12.894 ± 0.0203 | 2.9255 ± 0.0153 |
| Fe(TOB) | | |
| AH | 7.1788 ± 0.0902 | 7.17 ± 0.01 |
| $AH_2$ | 10.6795 ± 0.1076 | 3.8 ± 0.4 |

| | **$T_1$ relaxivity at 3.0 Tesla and 25 °C.** |
|---|---|
| **Complex** | $T_1$ ($mM^{-1}s^{-1}$) |
| **Fe-TOB** | 2.6 |
| **Fe-TOB-HSA** | 2.3 |
| **Fe-TACO** | 1.3 |
| **Fe-TACO-HSA** | 1.3 |
| **Fe-EDTA** | 1.5 |

(i) Pd/C, $H_2$(g), MeOH, 3 days. (ii) ACN, DIPEA, 12 hr, and one of the following (a) Methyl Iodide (b) 4-(bromomethyl)-1,1'-biphenyl (c) 1-(bromomethyl)-4-methoxybenzene (d) 2-bromoacetamide (e) N-benzyl-2-bromoacetamide (f) tert-butyl 2-(4-(bromomethyl)-1H-1,2,3-triazol-1-yl)acetate (g) 1-benzyl-4-(bromomethyl)-1H-1,2,3-triazole (h) 1-bromo-2-(2-(2-methoxyethoxy)ethoxy)ethane (i) 2-chloro-N-(2-(4,4-diphenylpiperidin-1-yl)ethyl)acetamide.

a b c d e f g h i (i) Propargyl Alcohol, Azidomethyl pivalate 1:1, t-BuOH/$H_2O$ 2:1. 0.1 equivalence $CuSO_4$, 0.6 equivalence sodium ascorbate. 12 hr at RT. (ii) $CHCl_3$, 1.5 equivalence $PBr_3$ under Ar(g). 12 hr at RT. ESI-MS: m/z = 275.9/277.9 $[M+H]^+$.

(i) Propargyl Alcohol, Benzyl Azide 1:1, THF/$H_2O$ 2:1. 0.1 equivalence $CuSO_4$, 0.2 equivalence sodium ascorbate. 12 hr at RT. (ii) $CHCl_3$, 2.0 equivalence $PBr_3$ under Ar(g). 12 hr at RT. ESI-MS: m/z = 252.0/254.0 $[M+H]^+$.

(i) EtOH, 1.2 equivalence NaOH. 6 hr at RT. (ii) 1.2 equivalence HCl. ESI-MS: m/z = 327.2 $[M+H]^+$

COMPOUNDS FOR USE AS IRON(III) MRI CONTRAST AGENTS

CROSS REFERENCE TO RELATED APPLICATIONS

This application is a continuation of U.S. patent application Ser. No. 16/615,024, filed Nov. 19, 2019, which is the National Stage Entry of PCT/US2018/033759, filed on May 21, 2018, which claims priority to U.S. Provisional Application No. 62/508,548, filed on May 19, 2017, the disclosures of which are hereby incorporated by reference.

STATEMENT REGARDING FEDERALLY SPONSORED RESEARCH

This invention was made with government support under Grant No. CHE1310374 awarded from the National Science Foundation and EB025369 from the National Institutes of Health. The government has certain rights in this invention.

FIELD OF THE DISCLOSURE

This disclosure relates generally to iron(III) macrocyclic compounds. More particularly, this disclosure relates to iron(III) macrocyclic compounds that can be used as MRI contrast agents.

BACKGROUND OF THE DISCLOSURE

Nearly all clinically-used contrast agents contain gadolinium (Gd as trivalent Gd(III)), yet a substantial proportion of patients in the US population (ca 10%) are considered at risk for being given Gd(III) contrast agents due to toxicity arising from long-term exposure. In addition, there are new concerns that Gd(III) based MRI contrast agents are leading to the deposition of Gd(III) into brain, bone and skin of all patients. Alternatives to Gd(III) contrast agents include biologically relevant transition metal ions such as high-spin Fe(III) complexes.

An alternative approach in magnetic resonance imaging (MRI) is the development of contrast agents that utilize iron as an endogenous metal ion. Contrast agents containing Fe(III), as trivalent iron, would provide an alternative to Gd(III) contrast agents that are problematic for patients who cannot tolerate Gd(III). Most Fe(III) MRI contrast agents that have been reported to date contain simple linear chelates. There are three commonly used types of complexes. The most heavily studied are the class which contains an ethylene diamine backbone with a combination of phenol and carboxylate pendents such as EHBG (NN'-ethylenebis [(2-hydroxybenzyl)glycine). The second type contains polyaminocarboxylate ligands, such as Fe(III) complexes of EDTA. The third type contains the bacterial siderophore, desferrioxamine (DFO). All of these complexes have drawbacks including lack of exchangeable water ligands, reduction potentials that are amenable for ROS generation and/or difficulty of synthetic modification. Also, the aqueous solution chemistry of Fe(III) complexes is dominated by the formation of insoluble complexes with hydroxides and bridging oxide ligands. Improvements are needed to obtain Fe(III) complexes that are not effective catalysts for the production of ROS by tuning redox potential to stabilize Fe(III), are water soluble and are desirable $T_1$ relaxivity agents.

Based on at least the foregoing, there is an ongoing an unmet need in the art for Fe(III) Mill contrast agents with improved properties.

SUMMARY OF THE DISCLOSURE

High-spin Fe(III) complexes were developed as $T_1$ MRI contrast agents. High-spin Fe(III) has favorable paramagnetic properties that can shorten $T_1$ relaxation times of the protons of water for MRI contrast.

High-spin Fe(III) coordination complexes for use as $T_1$ MRI contrast agents are disclosed. The disclosed Fe(III) $T_1$ MRI contrast agents comprise macrocyclic ligands for control of spin and oxidation state as well as stability and solubility in water and biological media. The Fe(III) complexes may also be used as $T_2$ MRI contrast agents.

It is an object of the present disclosure to provide macrocyclic compounds, Fe(III) macrocyclic complexes, compounds, and compositions and methods of making and using same. In various examples, macrocyclic complexes and compositions of the present disclosure are used as MRI contrast agents.

The present disclosure provides a macrocyclic compound having i) a macrocyclic core comprising at least one heteroatom as a ligand donor and ii) at least one pendant donor as a substituent of the macrocyclic core. A macrocyclic compound may be referred to as a ligand when the macrocyclic compound is coordinated to an iron(III) ion. The macrocyclic core has a ring structure comprising carbon atoms and at least one heteroatom (e.g. N atom, O atom, or S atom).

The macrocyclic compound may comprise one or more ancillary pendant groups. The ancillary pendant group (s) may be one or more coordinating ancillary pendant groups and/or one or more non-coordinating ancillary pendant groups.

Certain pendants may have more than one N or O donor atom (e.g., pyrazole or imidazole. carboxylate or carboxylic acid) although generally only one is coordinated to metal ion.

A macrocyclic compound can have various pendant groups and combinations of pendant groups. When more than one pendant donor is present, they may be the same or different.

In an embodiment, the compounds of the present disclosure can have more than one macrocyclic core tethered together (i.e., covalently bound) via a linker group (e.g., aromatic groups), one or more macrocyclic compound of the present disclosure, a polymer, a dendrimer, or peptide.

In an aspect, the present disclosure provides imaging methods using the macrocyclic complexes and compounds described herein. The imaging methods use magnetic resonance imaging methods. Non-limiting examples of such methods include, Magnetic Resonance Imaging (MRI). Specifically, the macrocyclic compounds of the present disclosure, which are complexed to Fe(III), can be used as $T_1$ MRI contrast agents. The imaging methods of the present disclosure can be used to image a cell, tissue, organ, vasculature, or a part thereof. The cell, tissue, organ, vasculature can be a part of an individual.

Figure 2:
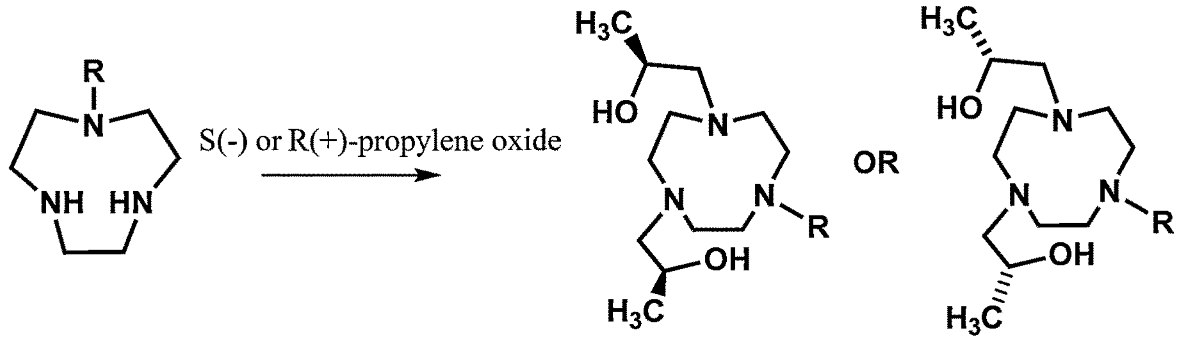

FIG. 2 general synthesis of TACN ligands with two chiral propyl alcohol pendents. Either R or S propylene oxide can be used to give pendents with opposite chirality. The non-coordinate group, R, is typically benzyl, methyl or biphenyl.

Figure 3:
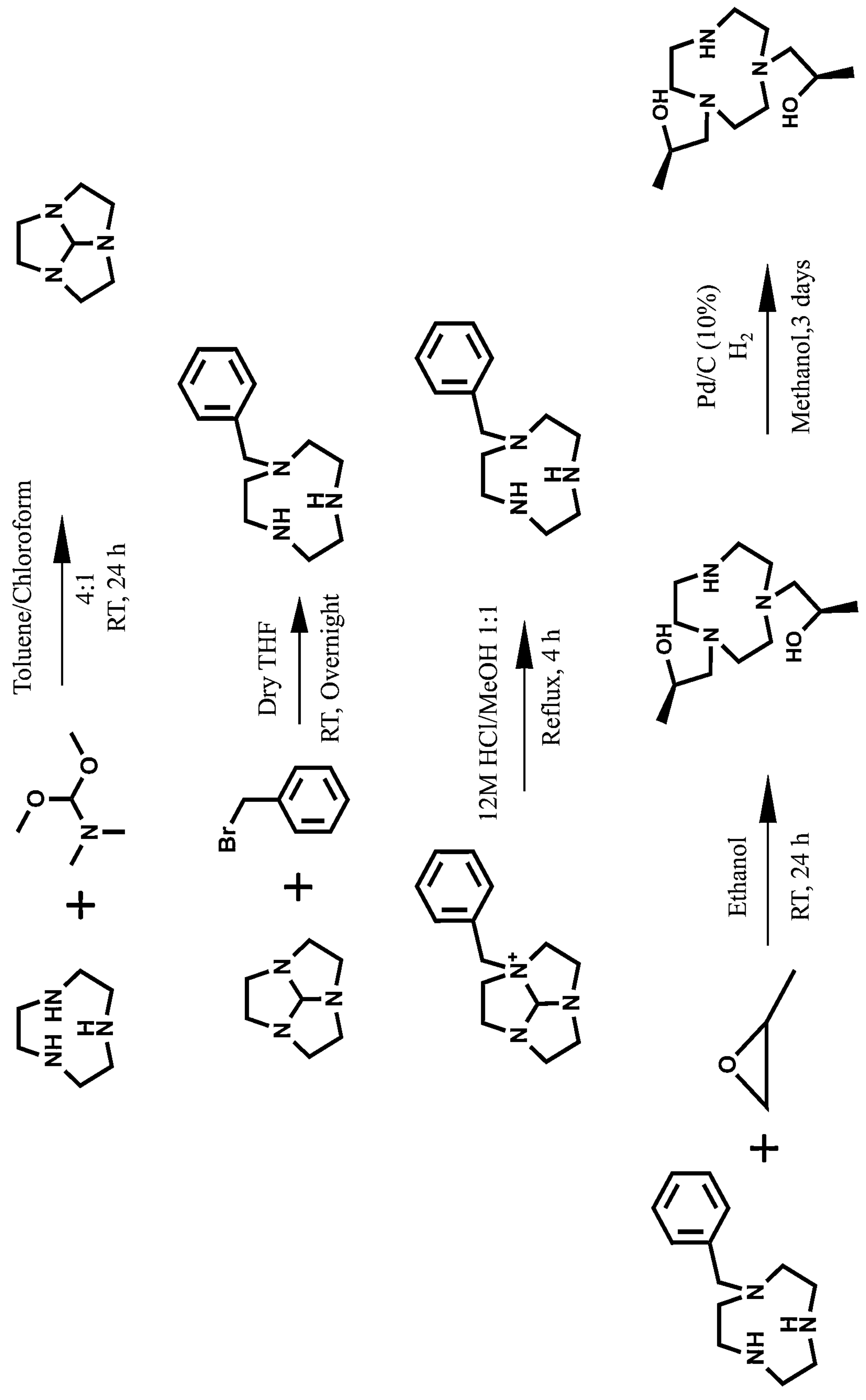

FIG. 3 shows synthesis of the TON ligand, a synthetic precursor from the TOB ligand. The benzyl group is removed by catalytic hydrogenation to produce TON.

Figure 4:
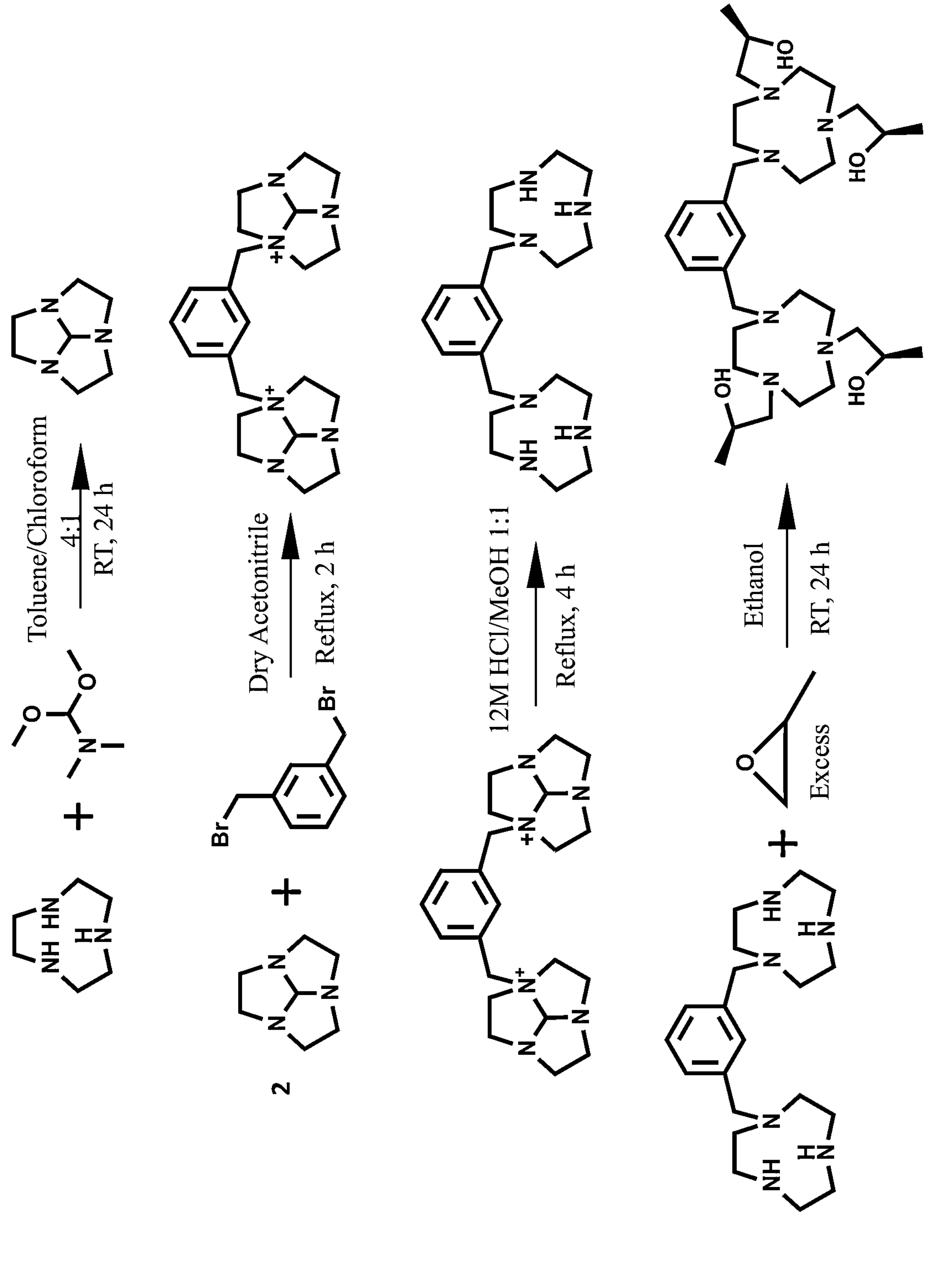

FIG. 4 shows example synthesis of a ligand that binds two Fe(III) ions. This figure shows the synthetic scheme for DT-meta.

Figure 5:
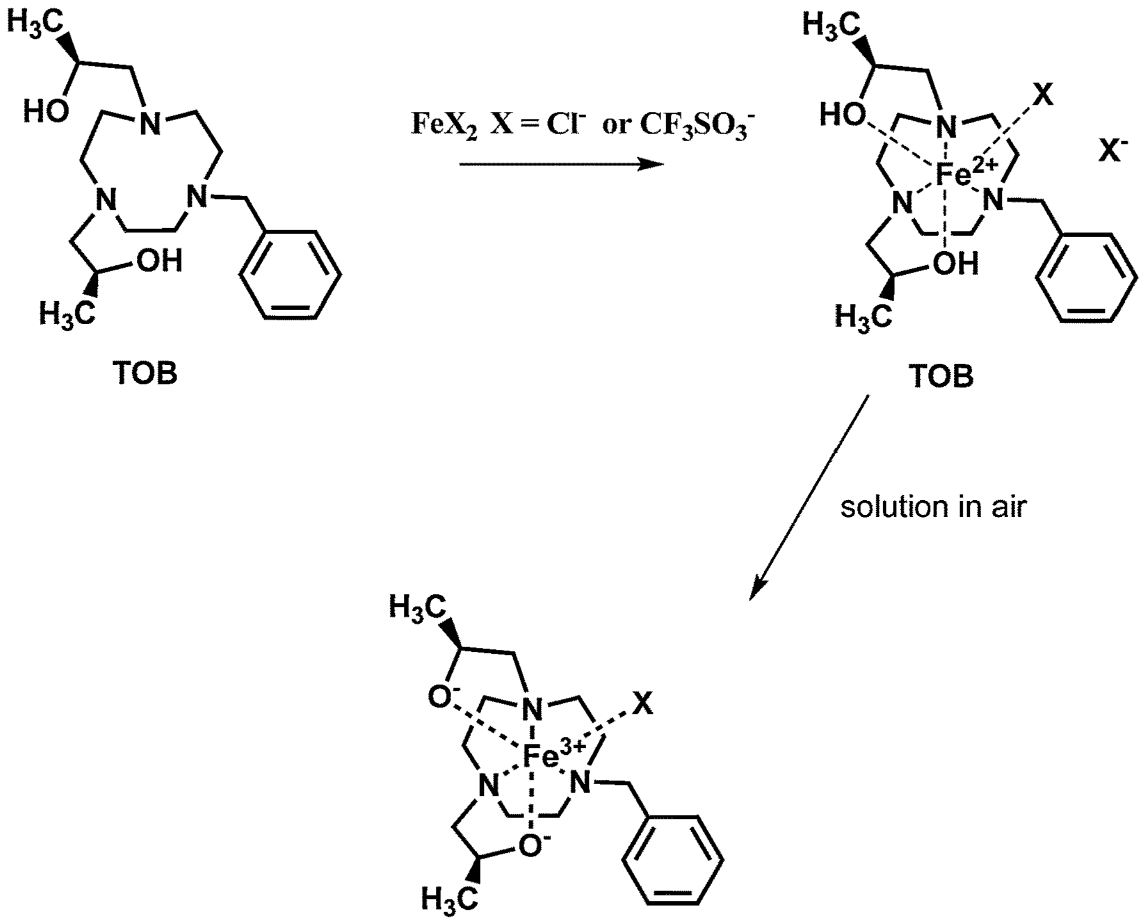

FIG. 5 shows synthesis of Fe(III) complex using Fe(II) salts. To 1,1'-7-benzyl-1,4,7-triazonane-1,4-diyl)bis(propan-2-ol) (TOB) was added $FeCl_2 \cdot 6H_2O$ or $Fe(CF_3SO_3)_2$ in ethanol and heated for 1 hr. Solution was cooled to room temperature, and diethyl ether was added until product precipitated followed by a diethyl ether wash. This produces the Fe(III) complex that results from oxidation of the Fe(II) complex. Fe(TOB)Cl, when dissolved in water, loses the Cl ligand and binds water or hydroxide.

Figure 6:
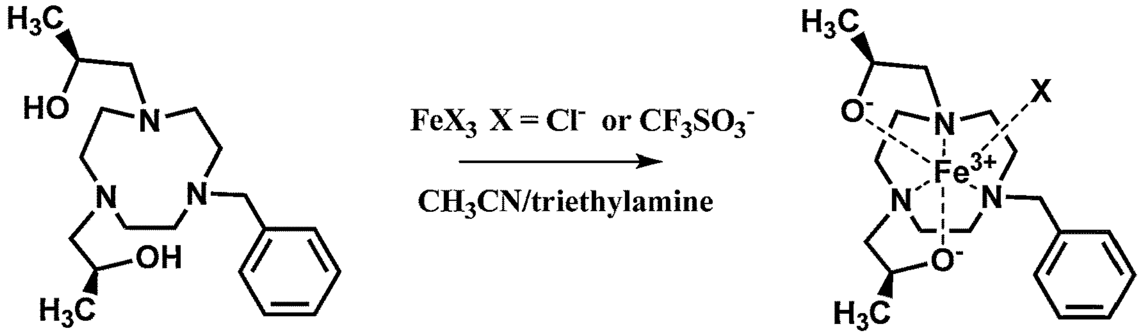

FIG. 6 shows synthesis of Fe(TOB) derivatives from Fe(III) salts. The free base of TOB is mixed with Fe(III) chloride in acetonitrile with two equivalents of trimethylamine base.

Figure 7:
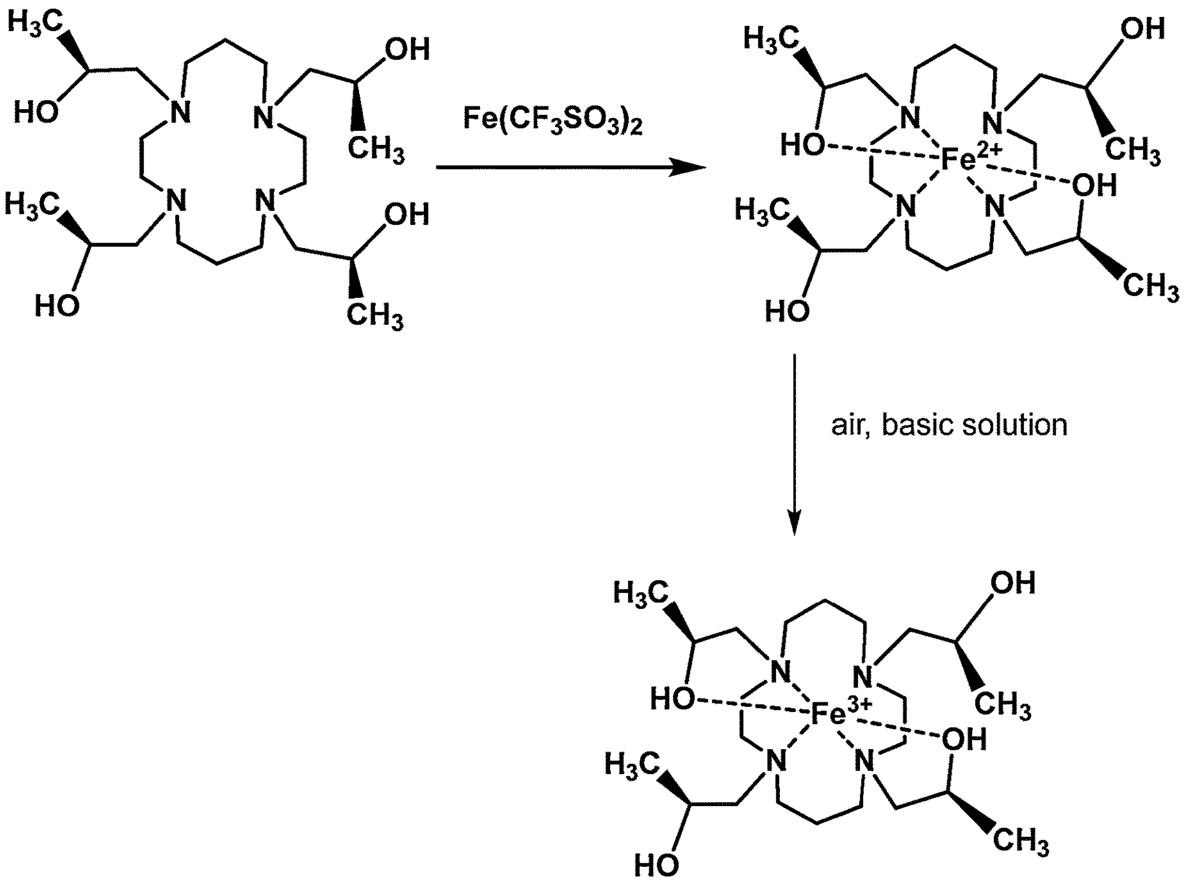

FIG. 7 shows synthesis of the Fe(III) complex of 1,4,8,11-tetrakis(2-hydroxypropyl)-1,4,8,11-tetrazacyclotetradecane (STHC).

Figure 8:
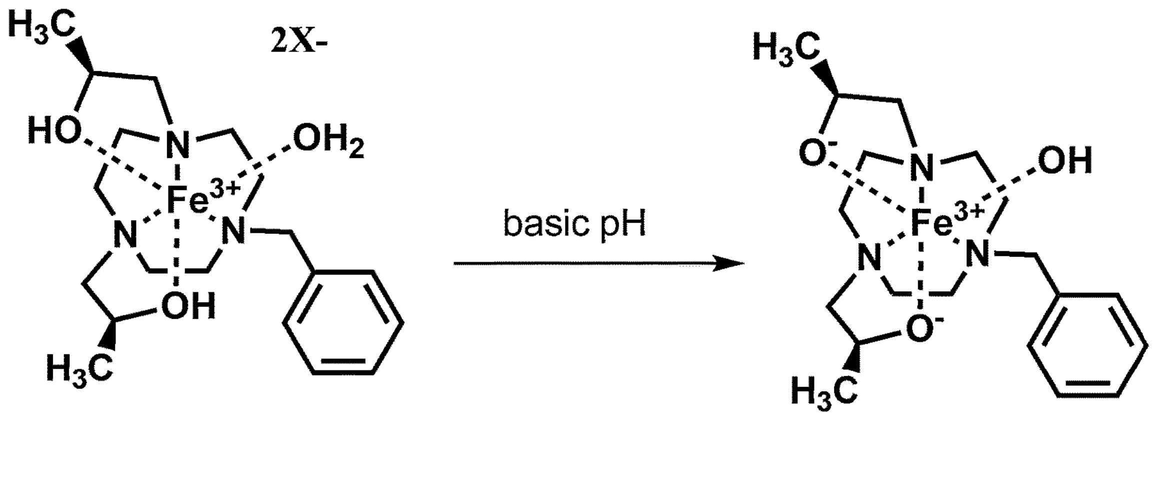

FIG. 8 shows bound water of Fe(TOB) may deprotonate to give a hydroxide ligand which is also a good $T_1$ relaxivity agent.

Figure 9:
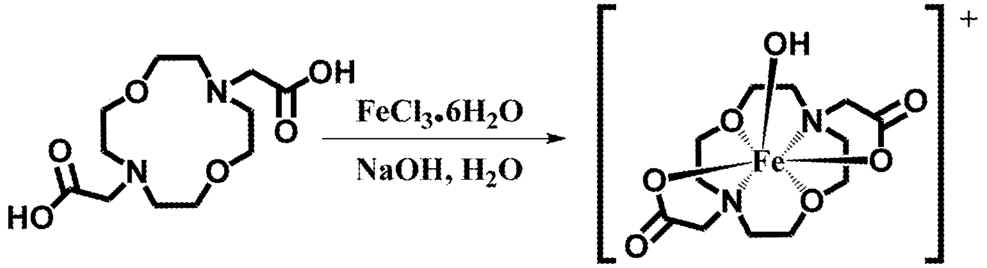

FIG. 9 shows synthesis of Fe(III) complex of 2,2'-(1,7-dioxa-4,10-diazacyclododecane-4,10-diyl) (NODAC) proceeds with Fe(III) salt.

Figure 10:
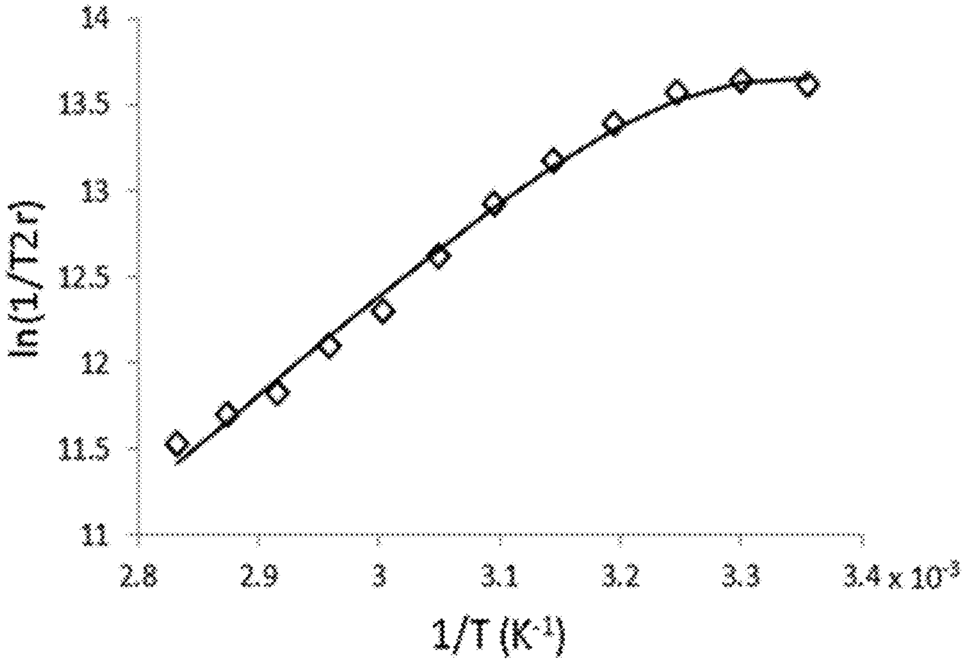

FIG. 10 shows a plot of data from variable temperature $^{17}O$ nuclear magnetic resonance (NMR) studies. The natural log of the inverse of the transverse relaxivity of the $^{17}O$ NMR resonance as a function of temperature is shown for an experiment containing 45 mM Fe(TOB) at pH 4. The $k_{ex}$ from this plot was determined to be $6.1\times10^6\ s^{-1}$ by fitting to the Swift-Connick equations.

Figure 11:
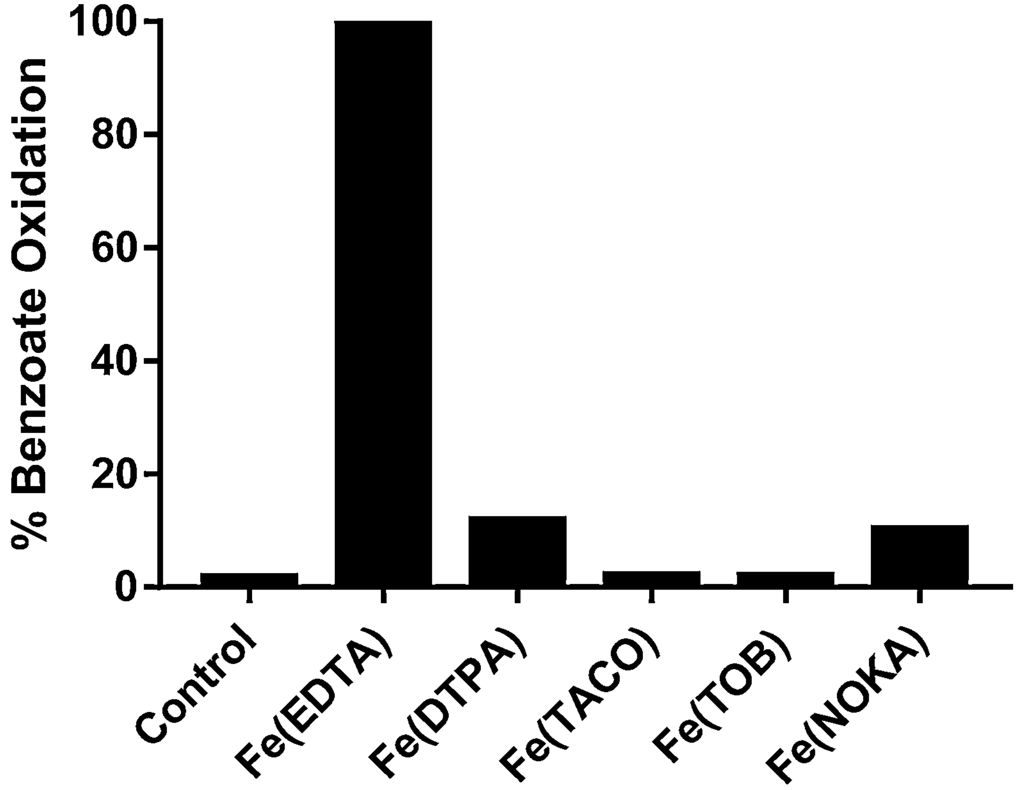

FIG. 11 shows Fe(III) contrast agents do not oxidize benzoate in the presence of peroxide and ascorbate, unlike Fe(III) complex of EDTA. Benzoate oxidation with 50 μM complex, 50 μM $H_2O_2$ and 50 μM ascorbate at pH 7.2. $[Fe(EDTA)]^-$ oxidation is set at 100%.

Figure 12:
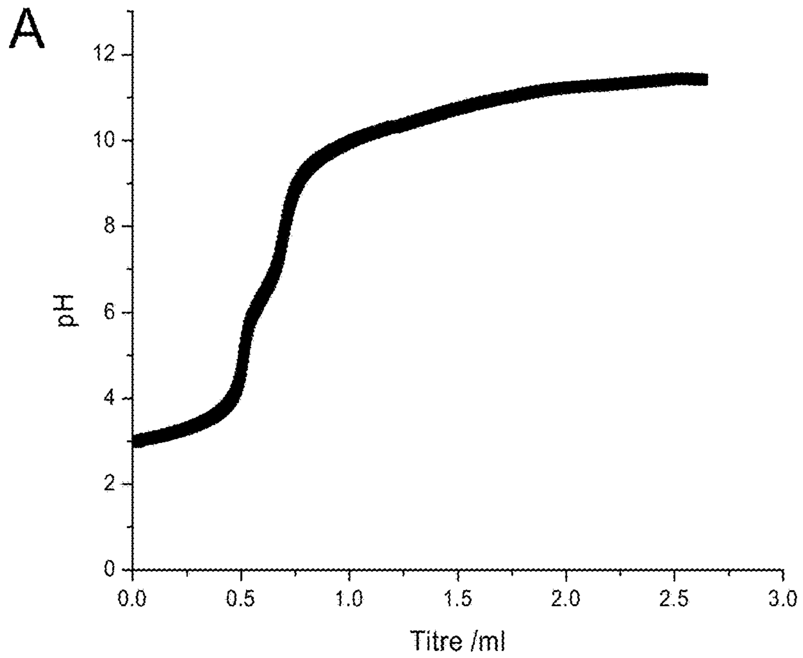
Figure 12:
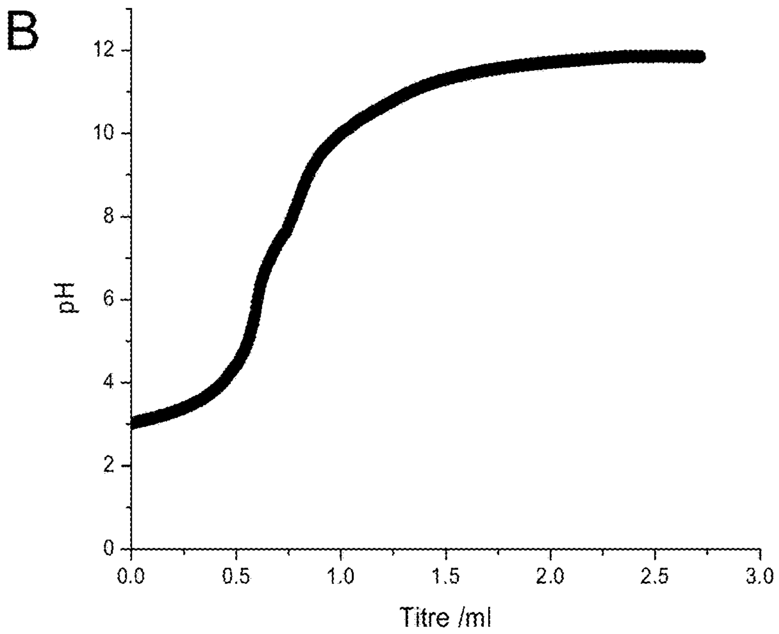

FIG. 12 shows pH-potentiometric titrations of Fe(TACO) and Fe(TOB) and equilibrium ionization constants from fitting the data. These data show that the Fe(TOB) has two $pK_a$ values at 3.8 and 7.2, supporting the deprotonation of two donor groups such as the alcohol pendents.

Figure 13:
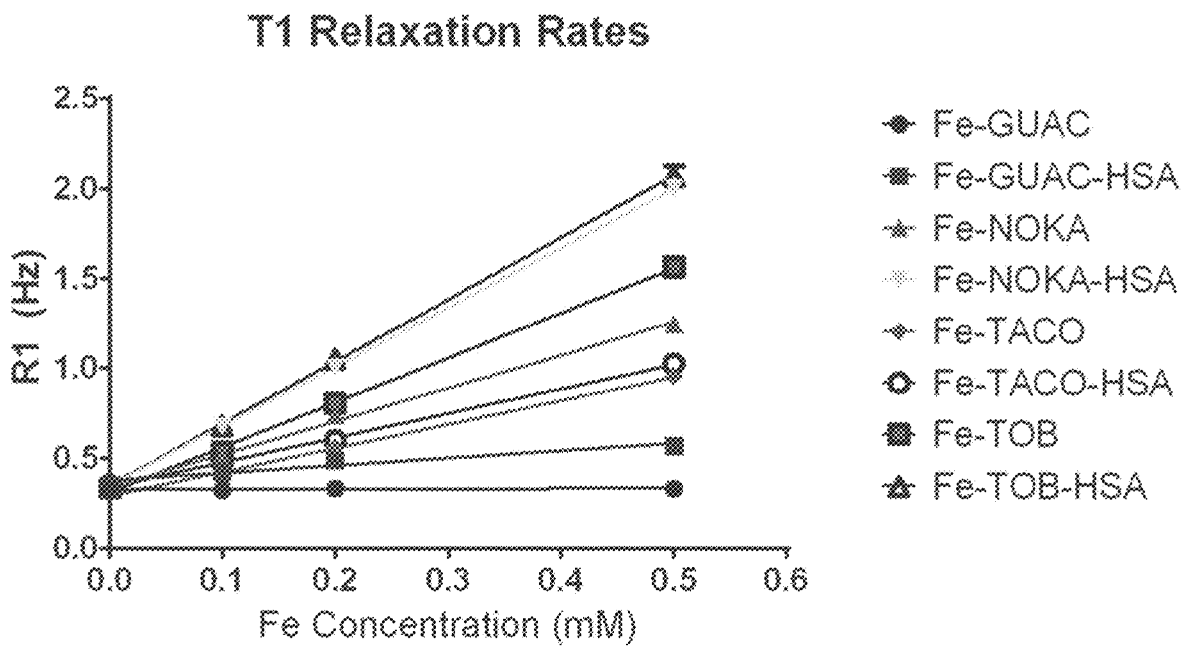

FIG. 13 shows plots of $T_1$ relaxation constants in Hz as a function of iron complex concentration on a 4.7 T MRI scanner at 37° C. The slope of the line is the $T_1$ relaxivity.

Figure 14:
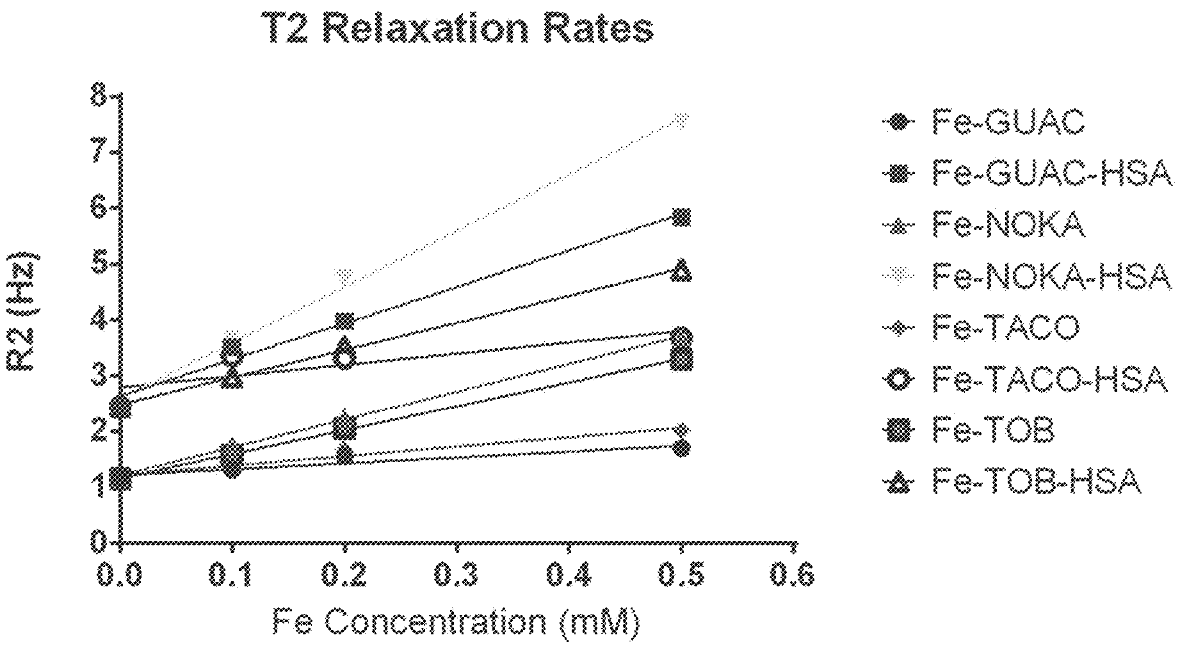

FIG. 14 shows plots of $T_2$ relaxation constants in Hz as a function of iron complex concentration on a 4.7 T MRI scanner at 37° C. The slope of the line is the $T_2$ relaxivity.

Figure 15:
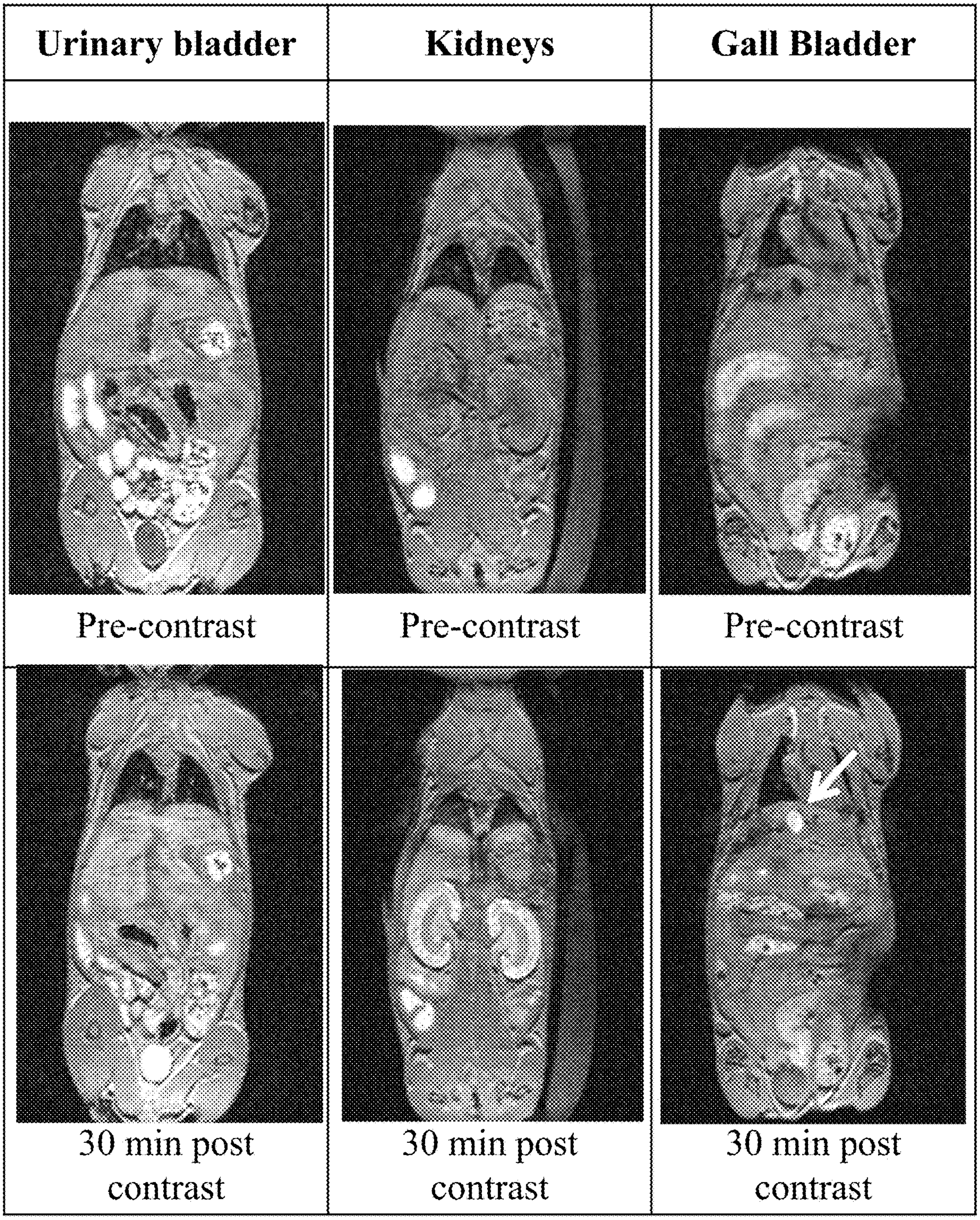

FIG. 15 shows MM scans of Mice: Balb/cAnNCr (n=2); injected with a dose of 0.2 mL of 6.2 mM Fe-TOB-HSA (10.5 mg of HSA). Scans are shown precontrast agent and 30 minutes post contrast.

Figure 16:
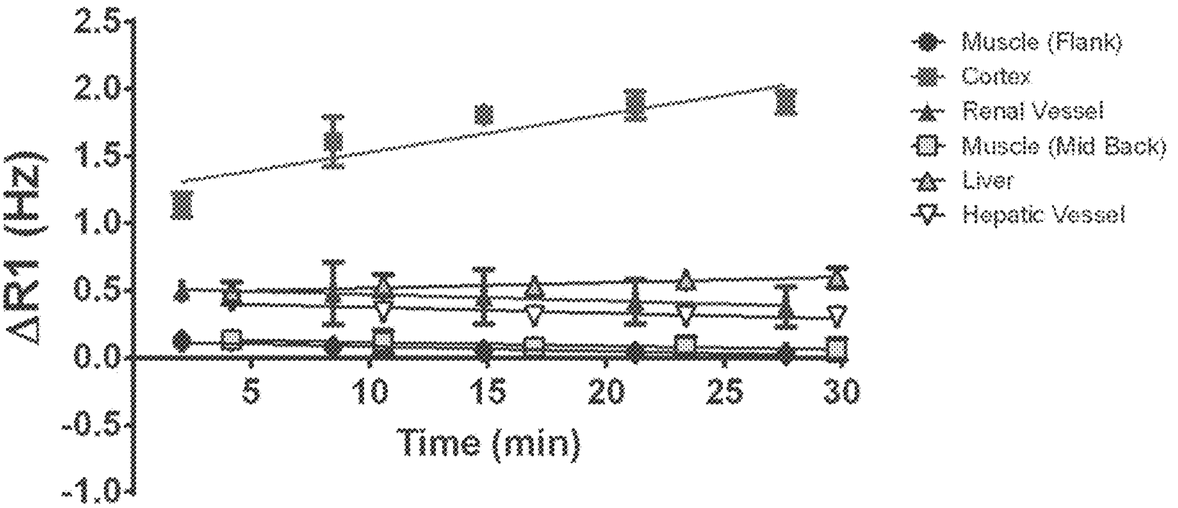

FIG. 16 shows plots of the change in $T_1$ relaxivity in the mouse over time after injection of Fe-TOB-HAS for various tissues including liver, muscle, renal vessel and cortex.

Figure 17:
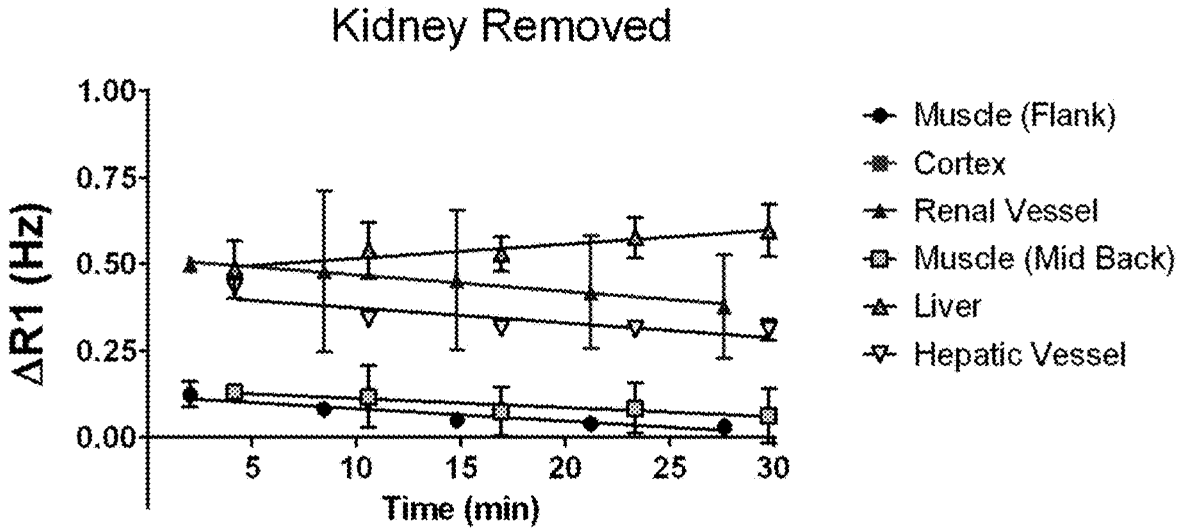

FIG. 17 shows plots of the change in $T_1$ relaxivity in the mouse over time after injection of Fe-TOB-HSA for various tissues including liver, muscle, renal vessel, but with kidney cortex data removed.

Figure 18:
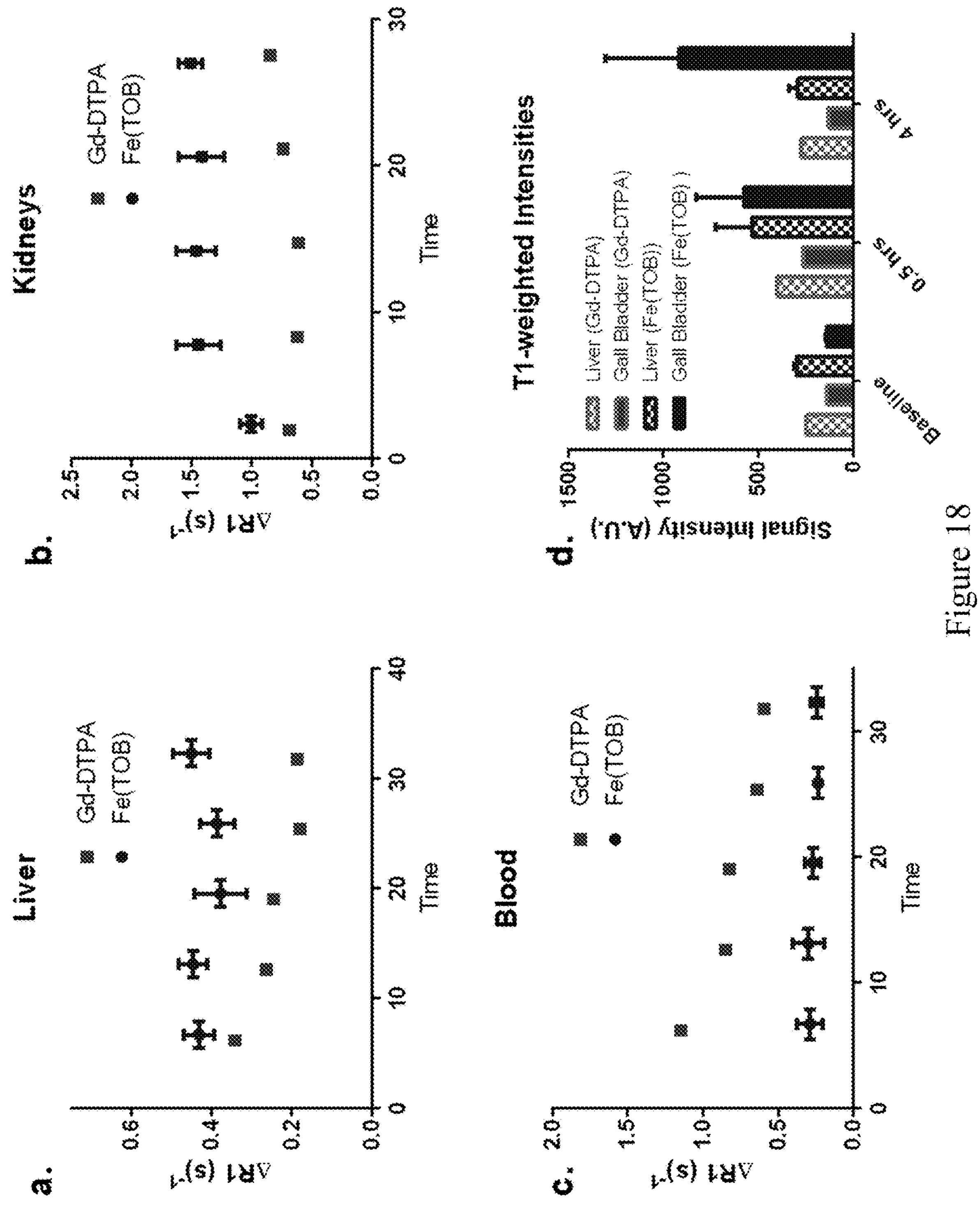

FIG. 18 shows (a-c) changes in $T_1$ rate constants for kidneys, liver and blood for Gd-DTPA vs. Fe(TOB), 50 μmol/kg each. Greater uptake of Fe(TOB) in kidneys and liver (a, b) results in faster removal from the blood (c). Elimination of Fe(TOB) by the biliary system is confirmed by strong enhancement of the gall bladder at 30' and 4 h post-injection (d).

Figure 19:
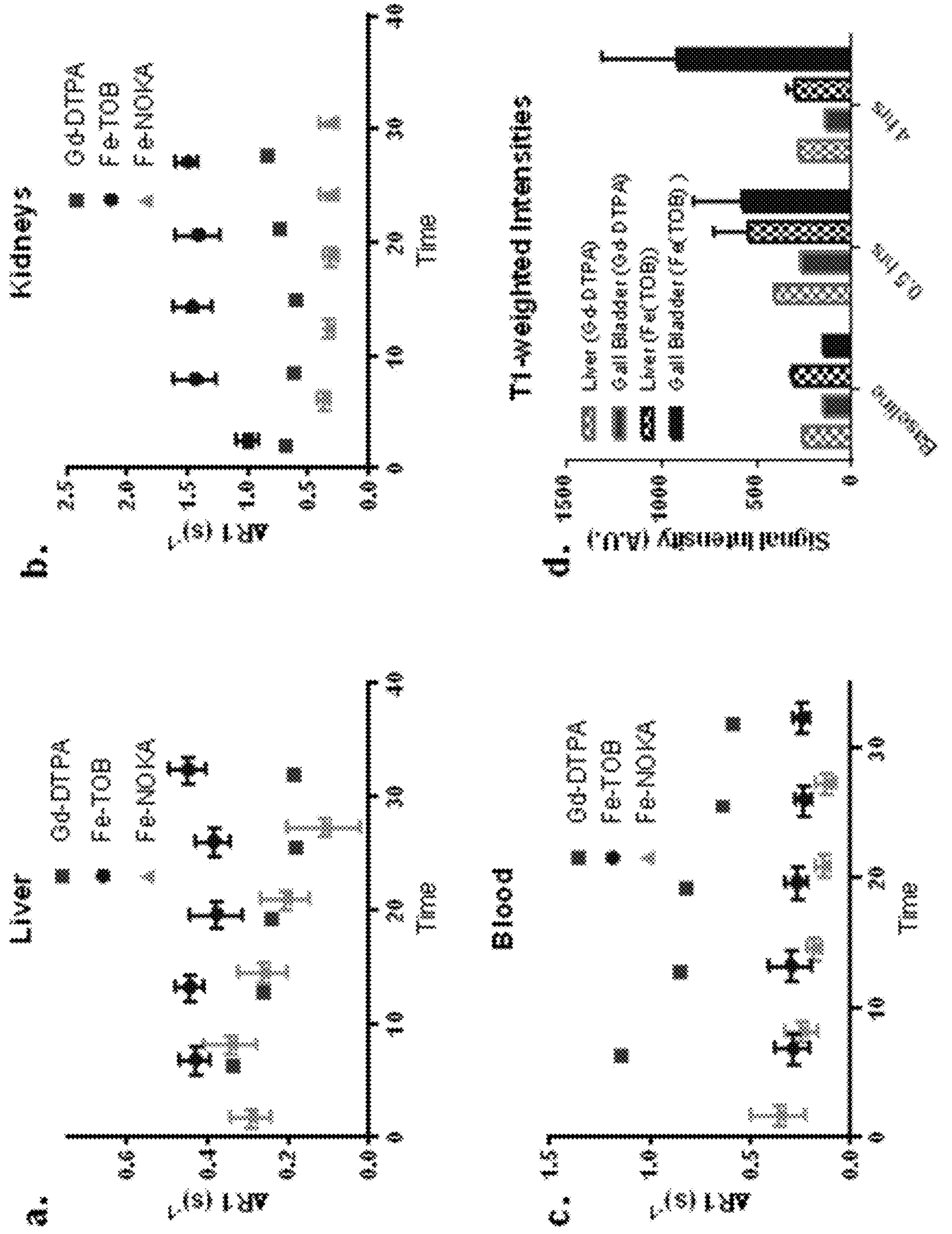

FIG. 19 shows (a-c) changes in $T_1$ rate constants for kidneys, liver and blood for Gd-DTPA vs. Fe(TOB) vs. Fe(NOKA), at 50 μmol/kg each. Data shows that Fe(NOKA) does not produce $T_1$ contrast as great of that of Fe(TOB) or Gd(DTPA) in liver (a), kidneys(b) whereas Gd(DTPA) produces larger contrast in blood(c). Comparison shown in (d).

Figure 20:
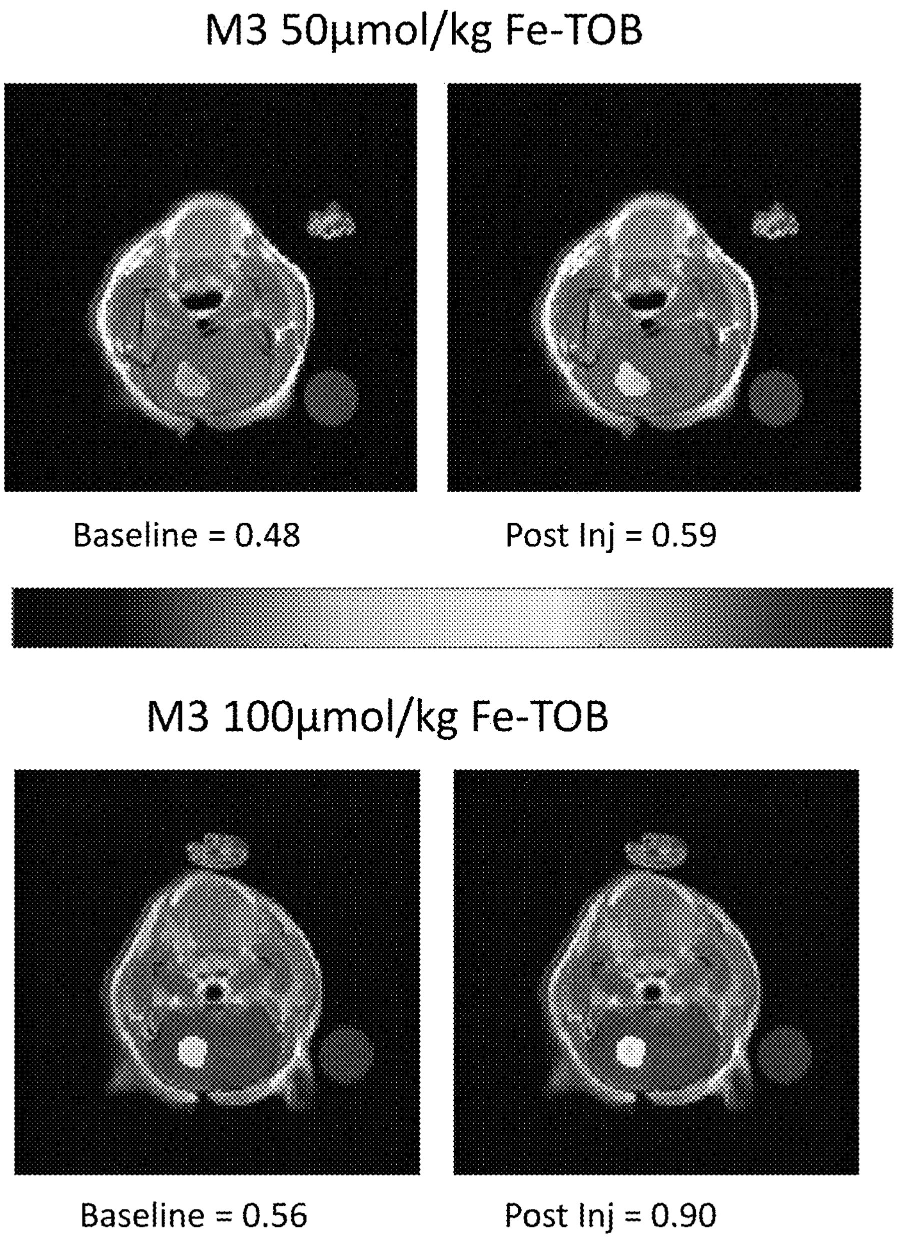

FIG. 20 shows MM scans of mice with brain tumors (C57BL/6NCr mice) at about 75 weeks old. Mice were dosed with Fe(TOB) at 0.05 mmol/kg Fe(TOB) complex or 0.1 mmol/kg Fe(TOB) complex.

Figure 21:
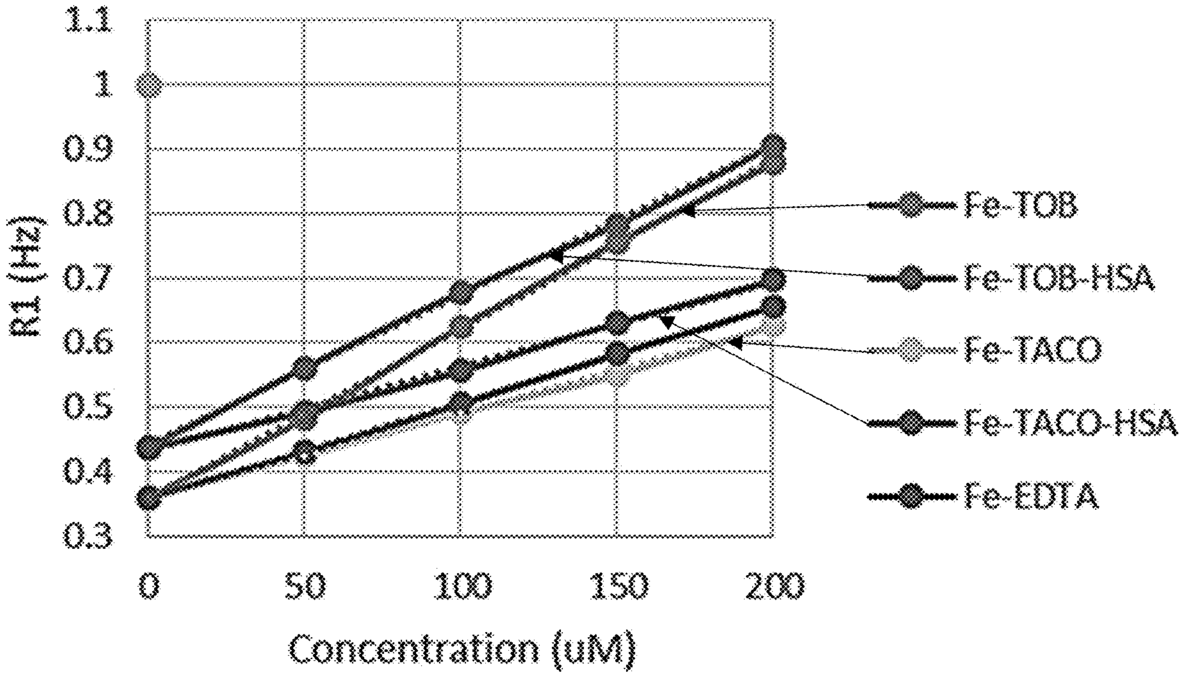

FIG. 21 shows $T_1$ relaxivity data for Fe(III) complexes on a 3 Tesla Toshiba clinical scanner at 25° C. Complexes were prepared in standard phosphate buffered saline (PBS) at pH 7.2.

Figure 22:
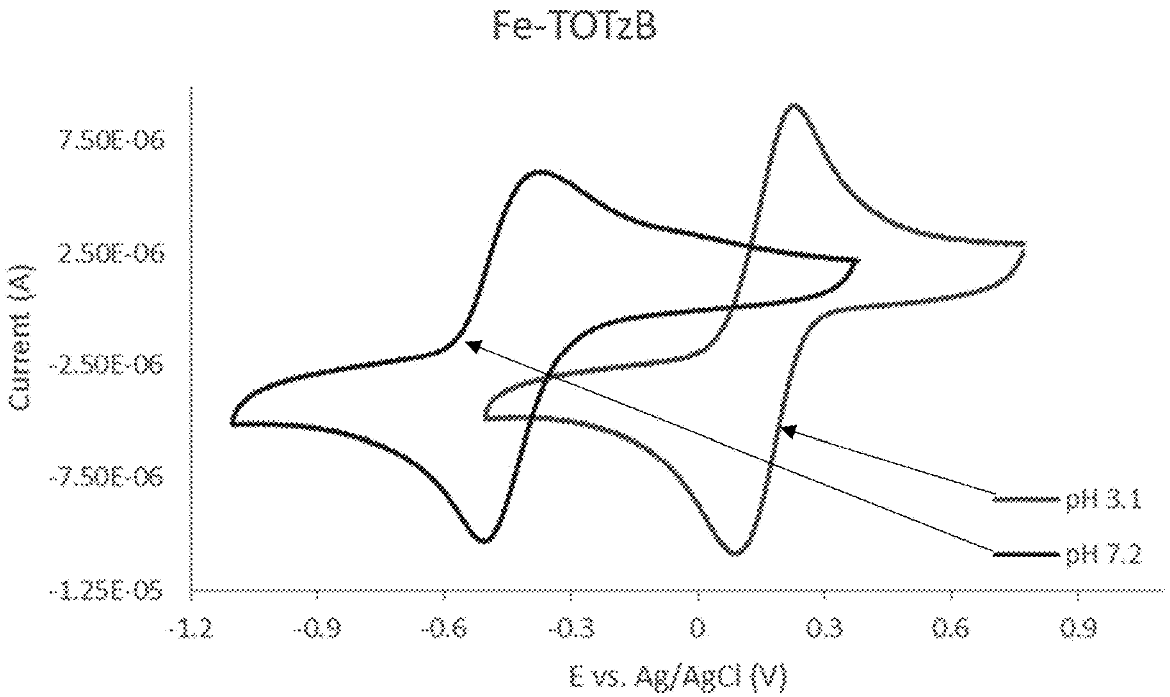

FIG. 22 shows cyclic voltammetry scans of Fe(TOTzB) in water versus NHE at two different pH values including pH 3.1 (right) with $E_o$ of about 200 mV and at pH 7.2 (left) with $E_o$ of about −400 mV. Change in redox potential at more basic pH is due to deprotonation of alcohol pendents.

Figure 23:
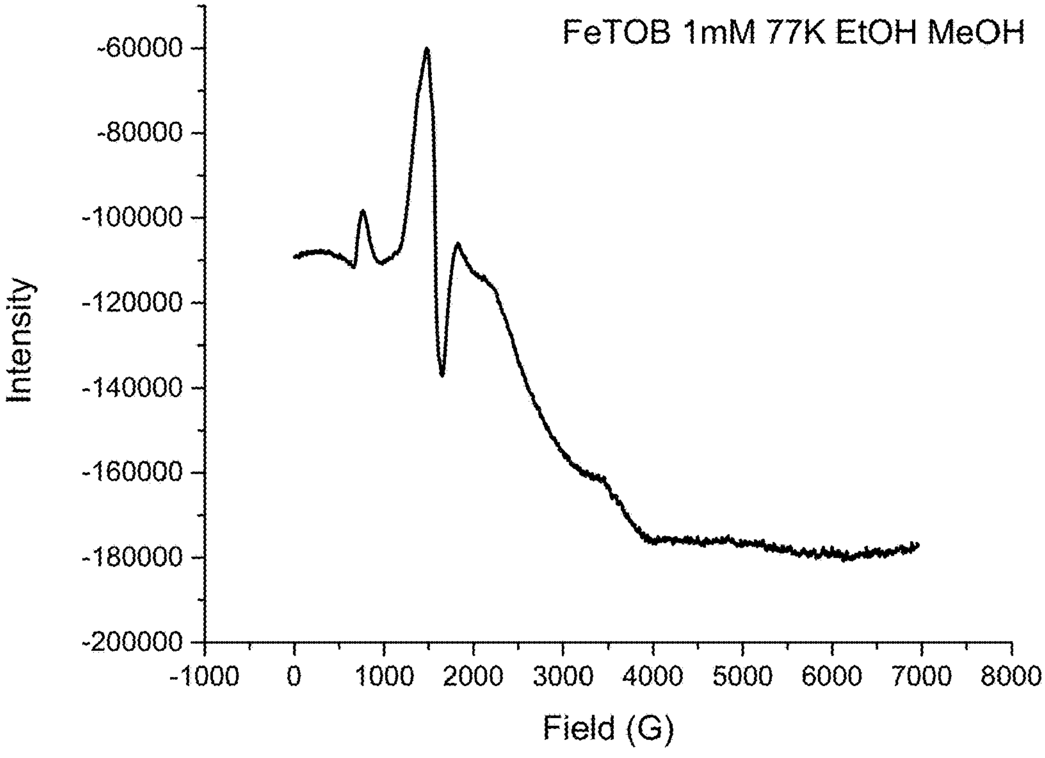

FIG. 23 shows X-band EPR spectrum of Fe(TOB) in methanol at 77 K.

Figure 24:
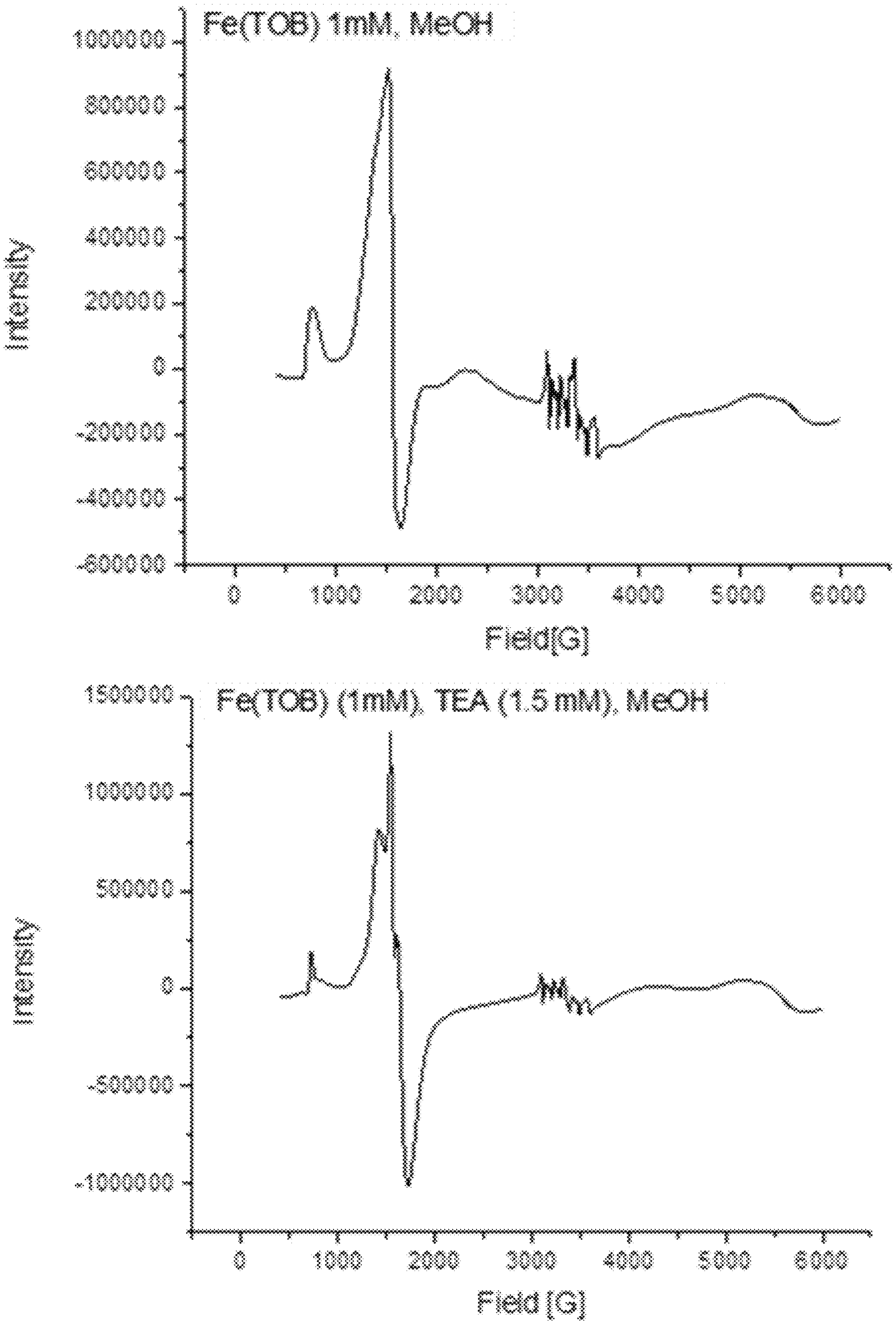

FIG. 24 shows X-band EPR spectrum of Fe(TOB) in methanol at 10 K and Fe(TOB) in methanol with 1.5 equivalents of triethylamine at 10 K. The signal at approximately 3400 G is due to a Mn(II) impurity.

Figure 25:
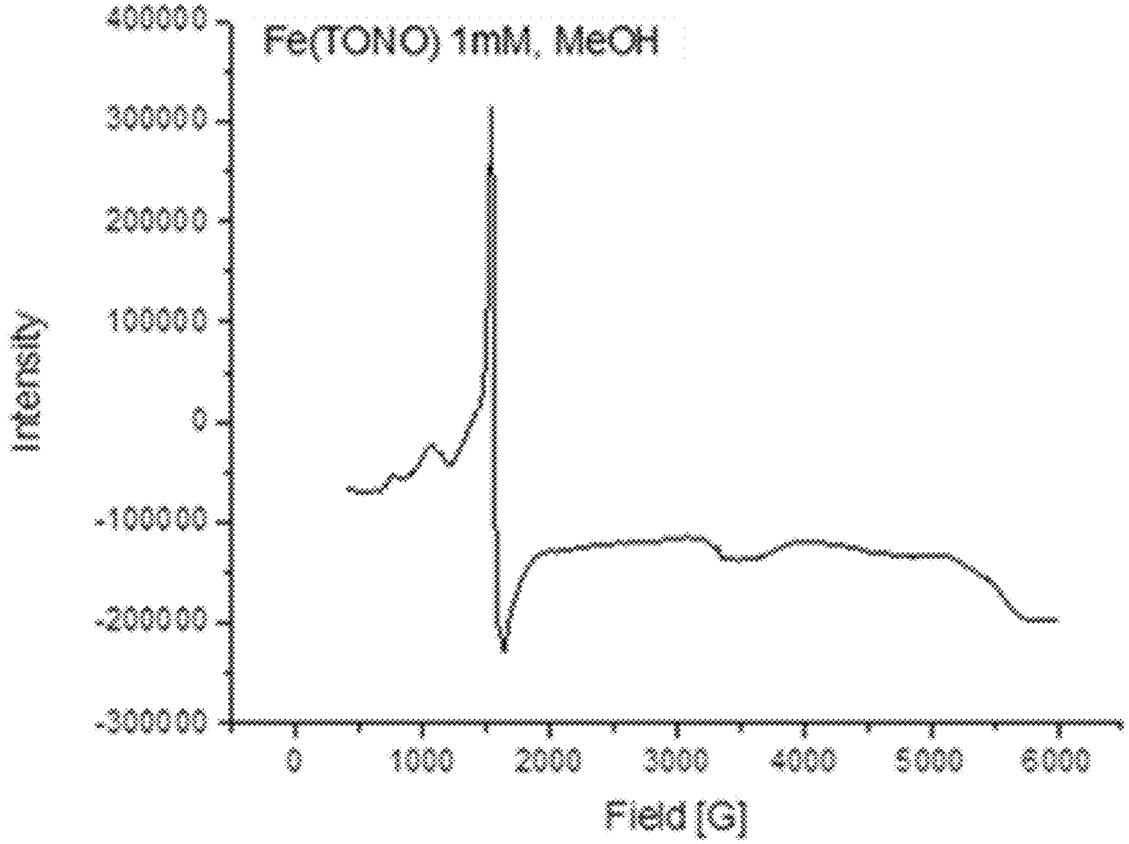

FIG. 25 shows X-band EPR spectrum of $Fe_2$(TONO) in methanol at 10 K.

Figure 26:
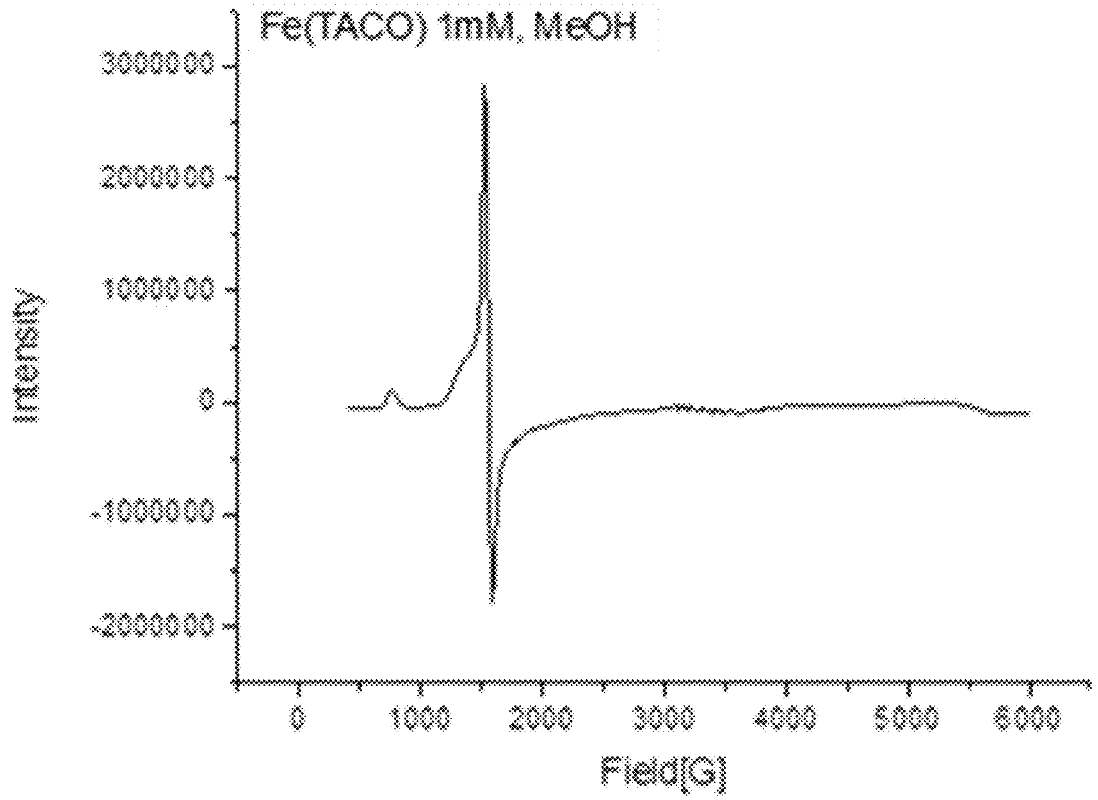

FIG. 26 shows X-band EPR spectrum of Fe(TACO) in methanol at 10 K.

Figure 27:
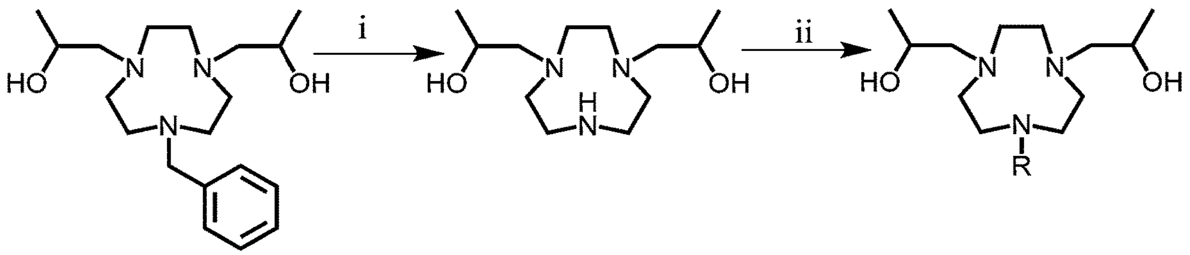
Figure 27:
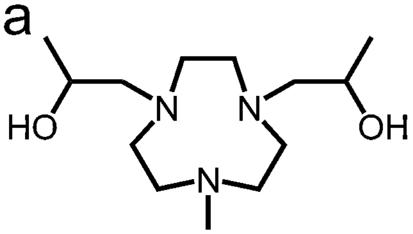
Figure 27:
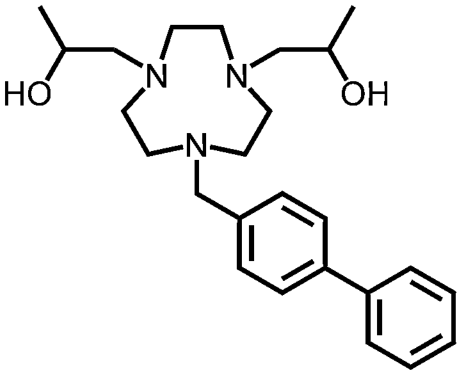
Figure 27:
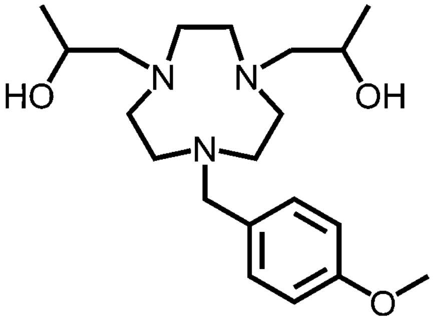
Figure 27:
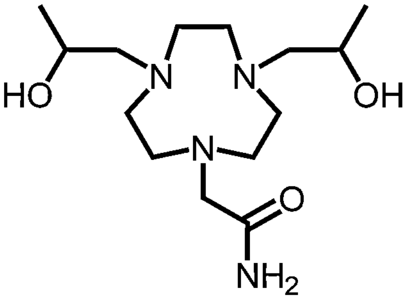
Figure 27:
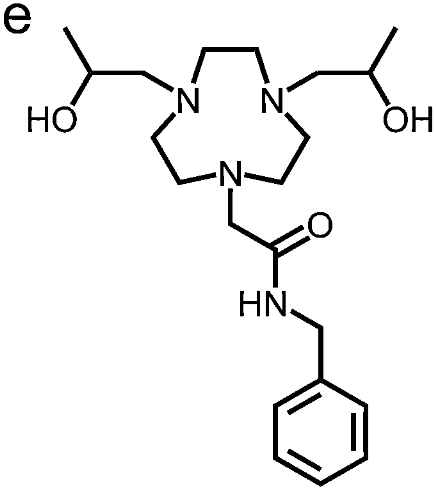
Figure 27:
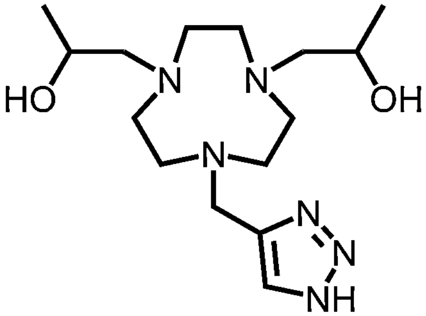
Figure 27:
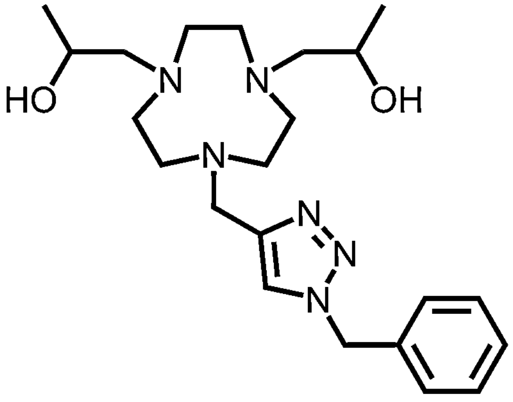
Figure 27:
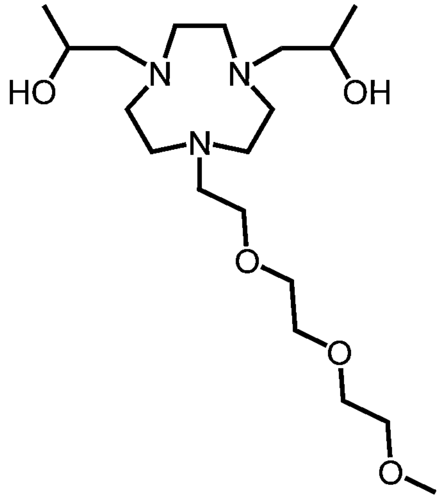
Figure 27:
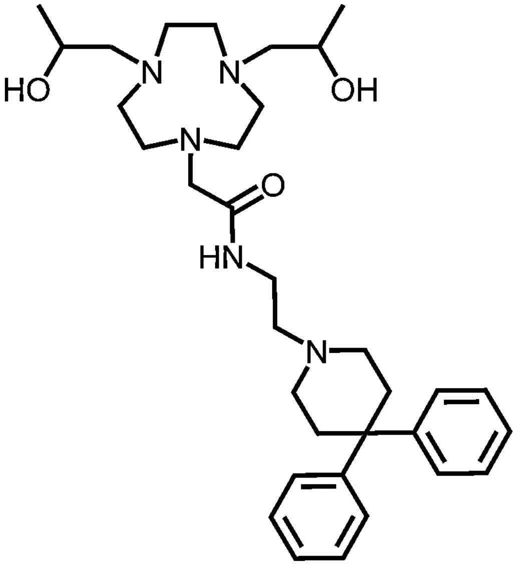

FIG. 27 shows a general synthesis of TACN derivatives with two hydroxypropyl pendents and a third variable pendent. Mass spectrometry data is given for each of the new ligands: L(a): ESI-MS: m/z=260.3 $[M+H]^+$; L(b): ESI-MS: m/z=612.3 $[M+H]^+$; L(c): ESI-MS: m/z=366.3 $[M+H]^+$; L(d): ESI-MS: m/z=303.2 $[M+H]^+$; L(e): ESI-MS: m/z=393.3 $[M+H]^+$; L(f): ESI-MS: m/z=327.2 $[M+H]^+$; L(g): ESI-MS: m/z=417.3 $[M+H]^+$; L(h): ESI-MS: m/z=392.3 $[M+H]^+$; and L(i): ESI-MS: m/z=566.4 $[M+H]^+$.

Figure 28:
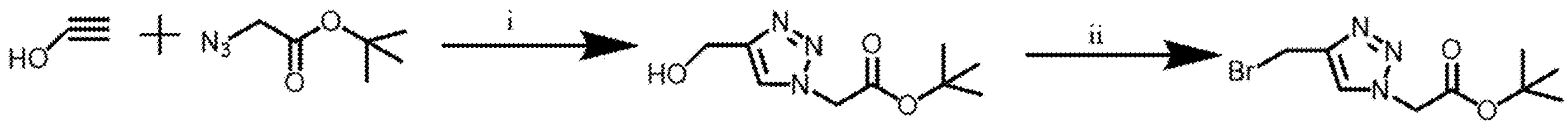

FIG. 28 shows a scheme for synthesis of triazole pendent used to synthesize TOTO.

Figure 29:
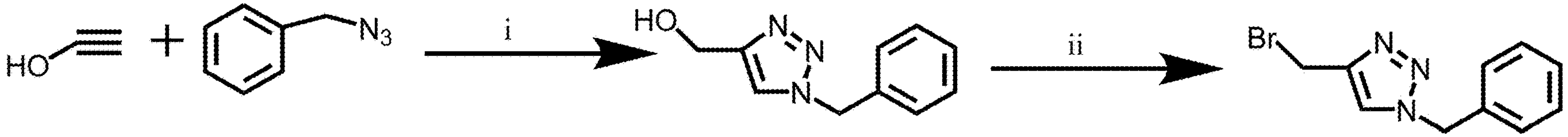

FIG. 29. Scheme for synthesis of triazole pendent used to synthesize TOTBz.

Figure 30:
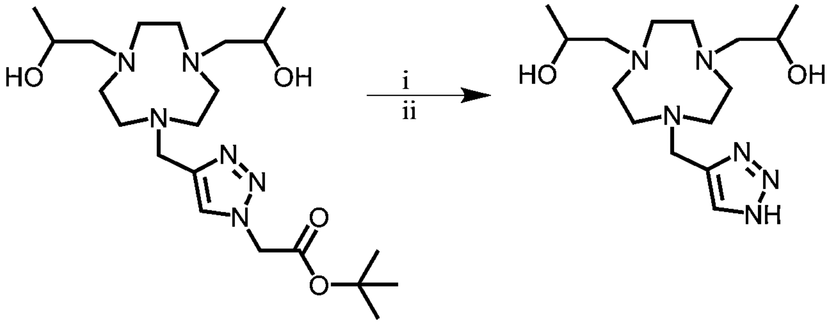

FIG. 30 shows a scheme for the synthesis of TOTO.

DETAILED DESCRIPTION OF THE DISCLOSURE

Although claimed subject matter will be described in terms of certain embodiments/examples, other embodiments/examples, including embodiments/examples that do not provide all of the benefits and features set forth herein, are also within the scope of this disclosure. Various structural, logical, and process step may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range. As an illustrative example, any range provided herein includes all values that fall within the ranges to the tenth decimal place, unless indicated otherwise.

As used herein, unless otherwise stated, the term "group" refers to a chemical entity that has one terminus that can be covalently bonded to other chemical species. Illustrative examples of groups include, but are not limited to:

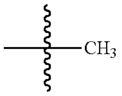
and
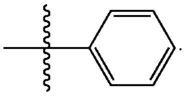

As used herein, unless otherwise stated, the term "moiety" refers to a chemical entity that has two or more termini that can be covalently bonded to other chemical species. Illustrative examples of moieties include, but are not limited to:

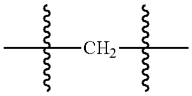
and
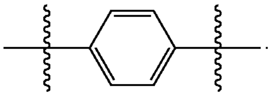

A moiety is also referred to herein as a segment.

As used herein, unless otherwise indicated, the term "alkyl" refers to branched or unbranched saturated hydrocarbon groups/moieties. Examples of alkyl groups/moieties include, but are not limited to, methyl groups/moieties, ethyl groups/moieties, propyl groups/moieties, butyl groups/moieties, isopropyl groups/moieties, tert-butyl groups/moieties, and the like. For example, the alkyl groups/moieties is a $C_1$ to $C_{12}$ alkyl group/moiety, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, or $C_{12}$). The alkyl group/moiety can be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups), aryl groups, alkoxide groups, amine groups, carboxylate groups, carboxylic acids, ether groups, alcohol groups, alkyne groups (e.g., acetylenyl groups), and the like, and combinations thereof.

As used herein, unless otherwise indicated, the term "aryl" refers to $C_5$ to $C_{14}$, including all integer numbers of carbons and ranges of numbers of carbons therebetween, aromatic or partially aromatic carbocyclic groups/moieties. The aryl groups/moieties can comprise polyaryl moieties such as, for example, fused ring or biaryl moieties. The aryl group/moiety can be unsubstituted or substituted with one or more substituent. Examples of substituents include, but are not limited to, substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof. Examples of aryl gr groups/moieties groups include, but are not limited to, phenyl groups/moieties, biaryl groups/moieties (e.g., biphenyl groups/moieties), and fused ring groups/moieties (e.g., naphthyl groups/moieties).

As used herein, unless otherwise indicated, the term "heteroaryl" refers to a $C_5$ to $C_{14}$, including all integer numbers of carbons and ranges of numbers of carbons therebetween, monocyclic, polycyclic, or bicyclic ring groups/moieties (e.g., aryl groups) comprising one or two aromatic rings containing at least one heteroatom (e.g., nitrogen, oxygen, and sulfur atom) in the aromatic ring(s). The heteroaryl groups/moieties can be substituted or unsubstituted. Examples of heteroaromatic groups/moieties include, but are not limited to, benzofuranyl groups/moieties, thienyl groups/moieties, furyl groups/moieties, pyridyl groups/moieties, pyrimidyl groups/moieties, oxazolyl groups/moieties, quinolyl groups/moieties, thiophenyl groups/moieties, isoquinolyl groups/moieties, indolyl groups/moieties, triazinyl groups/moieties, triazolyl groups/moieties, isothiazolyl groups/moieties, isoxazolyl groups/moieties, imidazolyl groups/moieties, benzothiazolyl groups/moieties, pyrazinyl groups/moieties, pyrimidinyl groups/moieties, thiazolyl groups/moieties, and thiadiazolyl groups/moieties.

It is an object of the present disclosure to provide macrocyclic compounds, Fe(III) macrocyclic complexes, compounds, and compositions and methods of making and using same. In various examples, macrocyclic complexes and compositions of the present disclosure are used as MRI contrast agents.

The macrocyclic compounds of the present disclosure as ligands have advantages towards accomplishing control over spin and oxidation state of the Fe(III) complexes and also interactions of the complex with innersphere and outersphere water. The cavity of these macrocyclic ligands can be suitable for stabilization of Fe(III) in high-spin form. Also, control of the aqueous solution chemistry of the Fe(III) complex can be accomplished with these macrocyclic compounds. The macrocyclic complexes described here nearly encapsulate the Fe(III), but in some cases, have a coordination site for water ligands that enhances their efficacy as $T_1$ MRI contrast agents. Without intending to be bound to any particular theory, it is considered that the iron-based MRI contrast agents described herein (as high-spin, trivalent Fe(III)) produce contrast by the same paramagnetic mechanism as Gd(III) agents and are in small molecule form as coordination complexes, i.e., they are not nanoparticles.

In the present disclosure, the macrocyclic compounds have a variety of macrocyclic core structures and a variety of substituents (also referred to as "pendant donor groups," "pendant groups," "pendant donors," or "donor groups") on the macrocyclic core. Most typically, donor groups contain amides, alcohols or phenols, but with at least two alcohol groups or other groups that can deprotonate to form anionic groups. The macrocyclic compounds are complexed to Fe(III) to provide a stabilized trivalent state (e.g., $E_o<0$ mV versus NHE).

The present disclosure provides a macrocyclic compound having i) a macrocyclic core comprising at least one heteroatom as a ligand donor and ii) at least one pendant donor as a substituent of the macrocyclic core. A macrocyclic compound may be referred to as a ligand when the macrocyclic compound is coordinated to an iron(III) ion. The macrocyclic core has a ring structure comprising carbon atoms and at least one heteroatom (e.g. N atom, O atom, or S atom). As used herein, "macrocycle donor" refers to a heteroatom with an available lone pair of electrons to donate to the Fe(III) center when present in the macrocyclic core of the macrocyclic compound. For example, the macrocycle donor can be a nitrogen atom (e.g. a tertiary amine, a secondary amine), or an oxygen atom (e.g., an ether). As used herein, "pendant donor" refers to a heteroatom with an available lone pair of electrons to donate to the Fe(III) center when present in a substituent on the macrocyclic core of the macrocyclic compound. For example, the pendant donor can be a nitrogen-containing group (e.g., amino, benzimidazole, imidazole, aniline, pyrazoyl, triazole, benzotriazole, and the like), an oxygen-containing group (e.g., ketone, alcohol, alkoxide, carboxylic acid, and the like). Some pendant donors, such as, for example, carboxylic acid, alcohol, imidazole or pyrazole may deprotonate when complexed with Fe(III) or at certain pHs. Such protonated and deprotonated forms are within the scope of the disclosure. For example, the pendant donor may be a carboxylate ion, an imidazolate ion, a pyrazolate ion or an oxide (e.g., an alkoxide or a phenoxide).

In certain embodiments, the macrocyclic compounds have the following structure:

A

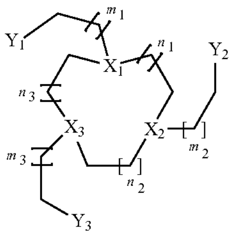

B

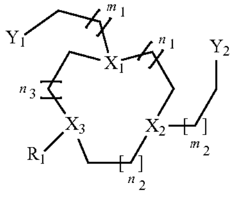

C

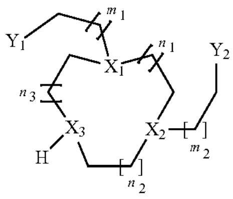

D

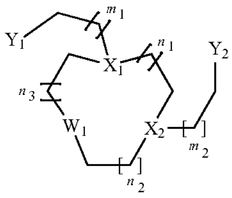

-continued

E

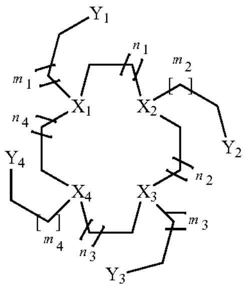

F

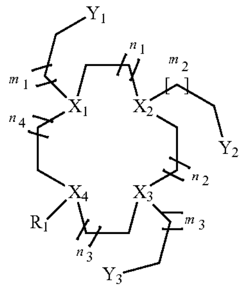

G

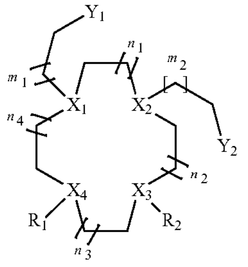

H

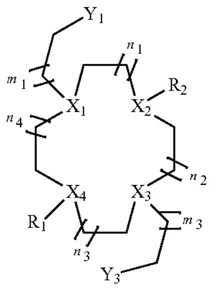

I

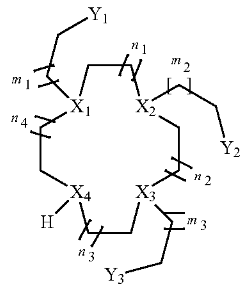

-continued

J

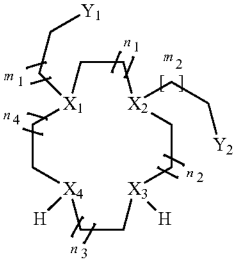

K

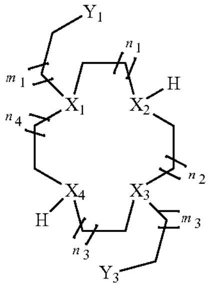

L

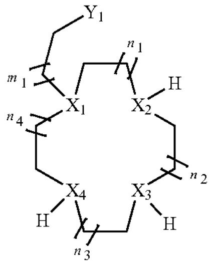

M

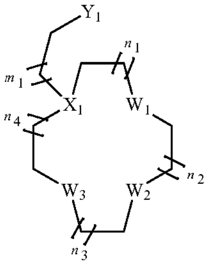

N

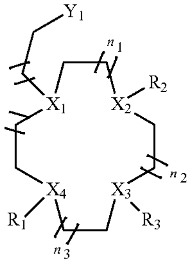

-continued

O

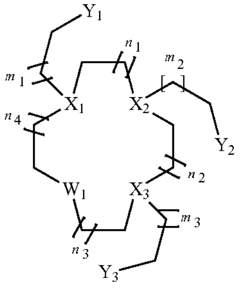

P

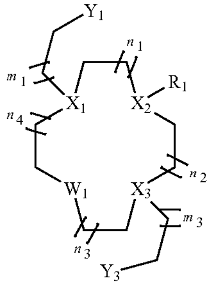

Q

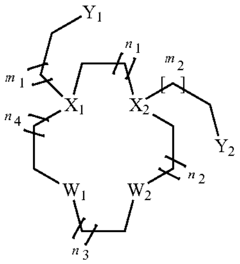

R

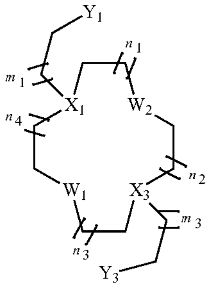

wherein $X_1$, $X_2$, $X_3$, and $X_4$ are N; $W_1$, $W_2$, and $W_3$ are each independently O or S; $Y_1$, $Y_2$, $Y_3$, and $Y_4$ are each independently pendant donors comprising N, wherein N has a lone pair of electrons (e.g., amino, benzimidazole, imidazole, aniline, pyrazoyl, triazole, benzotriazole, and the like), or a pendant donor comprising O, wherein O has at least one lone pair of electrons but preferably two or three lone pairs (e.g., ketone, alcohol, alkoxide, carboxylic acid, amide, phenol or phenoxide, or a deprotonated form of the foregoing, such as, for example, a carboxylate ion, an imidazolate ion, a pyrazolate ion or an oxide, including an alkoxide or a phenoxide; $m_1$, $m_2$, $m_3$, and $m_4$ are each independently 0, 1, or 2; $n_1$, $n_2$, $n_3$, and $n_4$ are each independently 1 or 2; and $R_1$, $R_2$, and $R_3$ are each independently substituted or unsubstituted aryl, substituted or unsubstituted heteroaryl or substituted or unsubstituted alkyl group, wherein $R_1$, $R_2$, and $R_3$ are not substituted by a pendant donor, wherein the alkyl segment of the alkyl-Y chain (alkyl-$Y_1$, alkyl-$Y_2$, alkyl-$Y_3$ and/or alkyl-$Y_4$) may each independently be substituted (e.g., Structure a or Structure b) or unsubstituted (Structure c or Structure d). For Structures a-f, the pendent may have either R or S configuration at the chiral carbon:

a

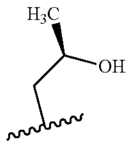

b

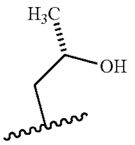

c

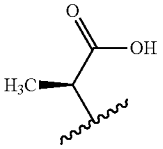

d

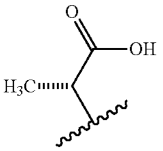

e

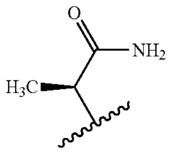

f

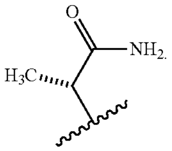

This paragraph is hereinafter referred to as "Scheme I."

In an embodiment, the disclosure provides macrocyclic compounds having the structures and definitions set forth in Scheme I with the proviso that when the above macrocyclic compounds have the structures labeled I-XVI in Scheme II, one combination or any combination of the provisos for Structures I-XVI apply.

In another embodiment, any or all of alkyl-$Y_1$, alkyl-$Y_2$, alkyl-$Y_3$, and alkyl-$Y_4$ may each independently be any of Structures 1-19 as defined in Scheme III.

Examples of suitable macrocyclic compounds include:

Scheme II (I)

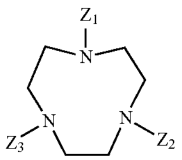

-continued (II)

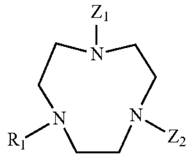

(III)

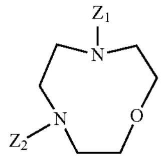

(IV)

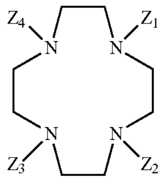

(V)

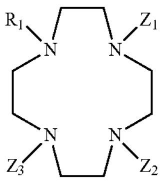

(VI)

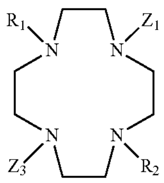

(VII)

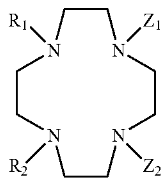

(VIII)

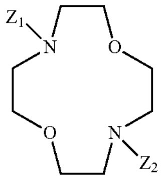

(IX)

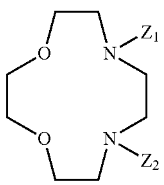

-continued (X)

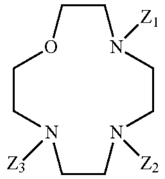

(XI)

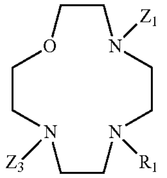

(XII)

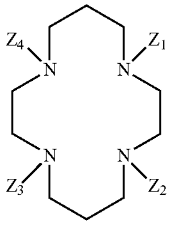

(XIII)

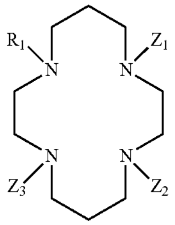

(XIV)

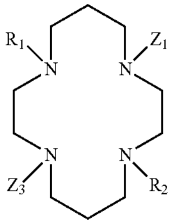

(XV)

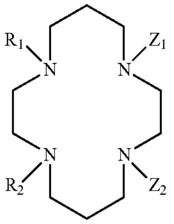

(XVI)

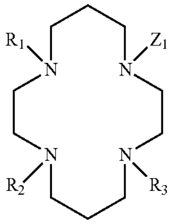

where $R_1$, $R_2$, and $R_3$ each independently is substituted or unsubstituted aryl, substituted or unsubstituted heteroaryl or substituted or unsubstituted alkyl group, where $R_1$, $R_2$, and $R_3$ are not substituted by pendant donors; and when the macrocyclic core has Structure I, $Z_1$ is H or one of the pendant groups in Scheme III and $Z_2$ and $Z_3$ each independently is a pendant group (e.g., one of the pendant groups in Scheme III);

when the macrocyclic compound has Structure II, III, VII, VIII, IX or XV, $Z_1$ and $Z_2$ each independently is a pendant group (e.g., one of the pendant groups in Scheme III);

when the macrocycle has Structure VI, XI or XIV, $Z_1$ and $Z_3$ each independently is a pendant group (e.g., one of the pendant groups in Scheme III);

when the macrocycle has Structure XVI, $Z_1$ is a pendant group (e.g., one of the pendant groups in Scheme III);

when the macrocycle has Structure IV, $Z_4$ is a pendant group (e.g., one of the pendant groups in Scheme III) and $Z_1$, $Z_2$ and $Z_3$ each independently is H or is a pendant group (e.g., one of the pendant groups in Scheme III), provided that at most two of $Z_1$, $Z_2$ and $Z_3$ is H;

when the macrocycle has Structure V, $Z_1$ and $Z_2$ each independently is H or a pendant group (e.g., one of the pendant groups in Scheme III) and $Z_3$ is a pendant group (e.g., one of the pendant groups in Scheme III);

when the macrocycle has Structure X, $Z_1$ and $Z_3$ each independently is a pendant group (e.g., one of the pendant groups in Scheme III) and $Z_2$ is H or a pendant group (e.g., one of the pendant groups in Scheme III);

when the macrocycle has Structure XII, $Z_4$ is a pendant group (e.g., one of the pendant groups in Scheme III) and $Z_1$, $Z_2$ and $Z_3$ each independently is H or a pendant group (e.g., one of the pendant groups in Scheme III), provided that at most two of $Z_1$, $Z_2$, and $Z_3$ is H;

when the macrocycle has Structure XIII, $Z_1$ and $Z_3$ each independently is a pendant group (e.g., one of the pendant groups in Scheme III) and $Z_2$ is H or a pendant group (e.g., one of the pendant groups in Scheme III);

wherein for all Structures I-XVI, each of $Z_1$, $Z_2$, $Z_3$ and $Z_4$, as applicable, are selected independently of each other. This paragraph is hereinafter referred to as "Scheme II."

The macrocyclic compound has at least one pendant donor on the macrocyclic core. For example, the pendant donor can have the following structure:

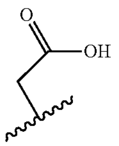

1

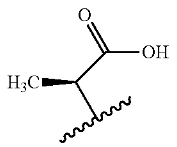

2

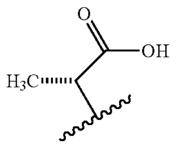

2'

-continued
3
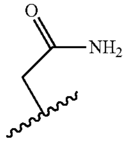
4
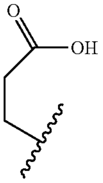
5
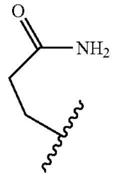
6
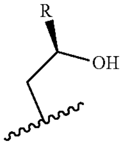
6′
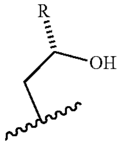
7
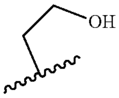
8
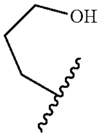
9
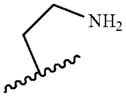
10
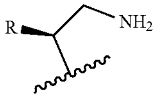
11
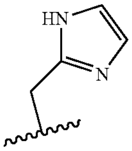
-continued
12
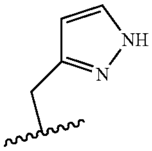
13
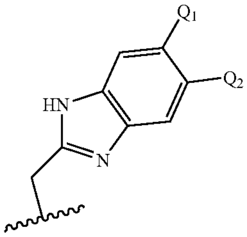
14
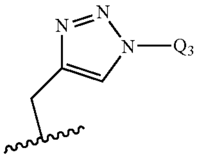
15
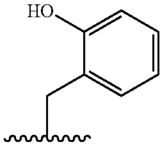
16
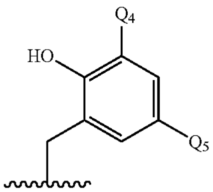
17
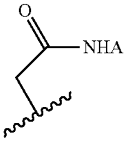
18
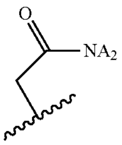
19
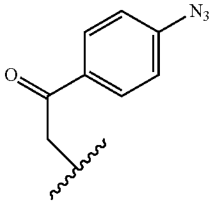
wherein $Q_1$ and $Q_2$ are each independently —H, —$OCH_3$, —$CO_2H$, or —$CH_2CO_2G_4$, $G_4$ is H, $C_1$ to $C_{12}$ substituted or unsubstituted alkyl groups of linear or branched structure or PEG group (—$CH_2CH_2O$—)$_n$ (n=1-12, e.g., 1, 2, 3, 4, 5, 6, 7, 8, 9, 10, 11, and 12), $Q_3$ is H, $C_1$ to $C_{12}$ substituted or unsubstituted alkyl groups of linear or branched structure or PEG group (—$CH_2CH_2O$—)$_n$ (n=1-12, e.g., 1, 2, 3, 4, 5, 6, 7, 8, 9, 10, 11, and 12), $Q_4$ and $Q_5$ are each independently —H, —$OCH_3$, —$CO_2H$, or substituted or unsubstituted alkyl groups of linear or branched structures, A is a substituted or unsubstituted alkyl group of linear or branched structure with $C_1$ to $C_{12}$ or is a substituted or unsubstituted aryl group or naturally occurring (e.g., glycine) or synthetic amino acid or analog thereof. Some pendant donors, such as, for example, carboxylic acid, alcohol, imidazole or pyrazole, may deprotonate when complexed with Fe(III) or at certain pH values. Such protonated and deprotonated forms are within the scope of the disclosure. For example, the pendant donor is a carboxylate ion, an imidazolate ion, a pyrazolate ion, or an oxide (e.g., an alkoxide or a phenoxide). This paragraph is hereinafter referred to as "Scheme III."

The macrocyclic compound may comprise one or more ancillary pendant groups. The ancillary pendant group (s) may be one or more coordinating ancillary pendant groups and/or one or more non-coordinating ancillary pendant groups.

A non-coordinating ancillary pendant group does not have a heteroatom that can bind to the Fe(III) metal ion to form a five-membered or six-membered chelate. Non-limiting examples of non-coordinating ancillary pendant groups include benzyl groups, phenyl groups, and other aromatic (e.g., aryl) groups that have one or more methylene group attached to aromatic group or no methylene groups), alkyl groups (both branched and linear groups), and the like. Other non-limiting examples of non-coordinating ancillary pendant groups include biphenyl, napthyl, anthracenyl, pyridyl, quinolyl, methyl, ethyl, isopropyl, n-propyl, ethyl methoxyether, PEG derivatives (polyethylene glycol), and the like.

Non-limiting examples of coordinating ancillary pendant groups (e.g., which is a third pendent group when two are already hydroxyl propyl) include oxygen or nitrogen donors that form five or six-membered chelates such as, for example, amides, carboxylates, alcohols or phenols, or derivatives of triazole, imidazole, pyrazole, picolyl, pyridine, alkylamines, aminopyridine, aminophenol, aniline, and the like. Some of these groups may deprotonate when bound to Fe(III).

A macrocyclic complex comprising one or more non-coordinating ancillary pendant group may have an open coordination site (have open coordination). A macrocyclic complex comprising one or more coordinating ancillary pendant group may not have an open coordination site (have closed coordination).

In an embodiment, the subject disclosure provides macrocyclic compounds having the structures and definitions set forth in Schemes II-IV, Scheme IV i

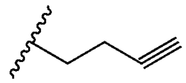

ii

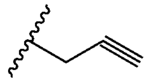

iii

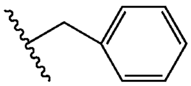

-continued iv

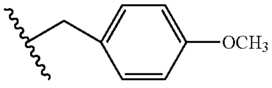

v

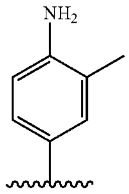

vi

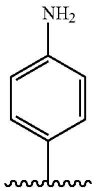

vii

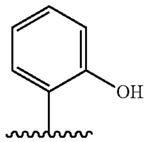

viii

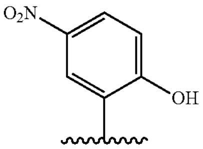

ix

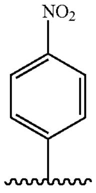

x

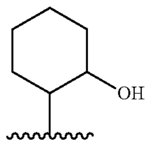

xi

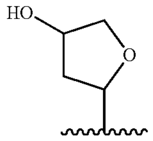

xii

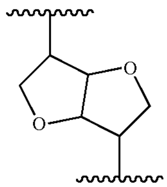

-continued xiii

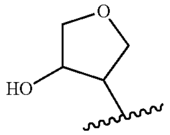

xiv xvi

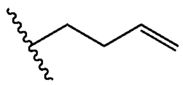

xv

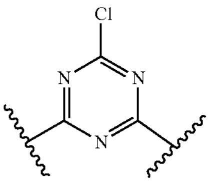

xvi

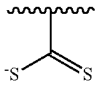

xvii

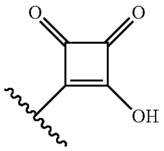

xviii

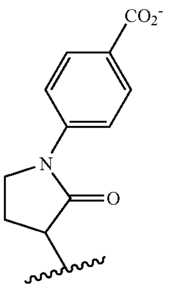

xix

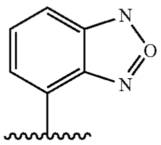

xx

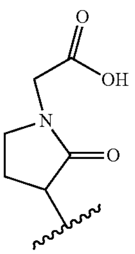

where any or all of the following provisos apply when the macrocycle has structure II: when $Z_1$=$Z_2$=Structure 1, $R_1$≠methyl, ethyl, isopropyl, n-hexyl or Structure i, ii, iii, or iv; when $Z_1$=$Z_2$=Structure 7, $R_1$≠Structure v or vi; when $Z_1$=$Z_2$=Structure 9, $R_1$≠ethyl; when $Z_1$=$Z_2$=Structure 12, $R_1$≠ethyl; when $Z_1$=$Z_2$=Structure 16 when $Q_4$=t-butyl and $Q_5$=$OCH_3$ or when $Q_4$=$Q_5$=t-butyl, $R_1$≠ethyl or isopropyl; when $Z_1$=$Z_2$=Structure 15, $R_1$≠methyl;

where any or all of the following provisos apply when the macrocycle has Structure III: when $Z_1$=Structure 16 when $Q_4$=t-butyl and $Q_5$=$OCH_3$ or when $Q_4$=$Q_5$=t-butyl, $Z_2$≠Structure 16 when $Q_4$=t-butyl and $Q_5$=$OCH_3$ or when $Q_4$=$Q_5$=t-butyl;

where any or all of the following provisos apply when the macrocycle has Structure V: when $Z_1$=$Z_2$=$Z_3$=Structure 17, $R_1$≠methyl, ethyl, n-propyl, n-butyl, n-dodecyl, or Structure ii, xiii, xv, ix, xvi or xix; when $Z_1$=$Z_2$=$Z_3$=structure 2, $R_1$≠Structure xvii or xx; when $Z_1$=$Z_2$=$Z_3$=Structure 1, $R_1$≠methyl, ethyl, n-propyl, n-butyl, n-pentyl, n-hexyl, n-octyl, n-decyl, n-octadecyl ($C_{18}$) or Structure ii, x, xi, xii, xiii, xiv or xvii;

where any or all of the following provisos apply when the macrocycle has Structure VI: when $Z_1$=$Z_3$=Structure 1, $R_1$=$R_2$≠methyl, Structure ii, x, or xi; when $Z_1$=$Z_3$=Structure 9, $R_1$=$R_2$≠methyl; when $Z_1$=$Z_3$=Structure 18, $R_1$=$R_2$≠methyl; when $Z_1$=$Z_3$=Structure 16 when $Q_4$=$Q_5$=methyl or t-butyl, $R_1$=$R_2$≠methyl; when $Q_4$=H and $Q_5$=Br, $R_1$=$R_2$≠methyl; when $Z_1$=$Z_3$=Structure 15, $R_1$=$R_2$≠methyl; when $Z_1$=$Z_3$=Structure 17, $R_1$=$R_2$≠methyl;

where any or all of the following provisos apply when the macrocycle has Structure XI: when $Z_1$=$Z_2$=Structure 1, $R_1$=$R_2$≠methyl;

where any or all of the following provisos apply when the macrocycle has Structure XIII: when $Z_1$=$Z_2$=$Z_3$=Structure 7, $R_1$≠methyl;

where any or all of the following provisos apply when the macrocycle has Structure XV: when $Z_1$=$Z_2$=Structure 1, Rid methyl; when $Z_1$=$Z_2$=Structure 3, Rid methyl; when $Z_1$=$Z_2$=Structure 4, $R_1$=$R_2$≠methyl; when $Z_1$=$Z_2$=Structure 1, $R_1$=$R_2$≠methyl; when $Z_1$=$Z_2$=Structure 5, $R_1$=$R_2$≠methyl; when $Z_1$=$Z_2$=Structure 7, $R_1$=$R_2$≠methyl; when $Z_1$=Structure 3 and $Z_2$=Structure 9, $R_1$=$R_2$≠methyl; when $Z_1$=$Z_2$=Structure 9, $R_1$=$R_2$≠methyl; when $Z_1$=$Z_2$=Structure 17, $R_1$=$R_2$≠methyl; when $Z_1$=$Z_2$=Structure 18, $R_1$=$R_2$≠methyl;

where any or all of the following provisos apply when the macrocycle has Structure XVI: when $Z_1$=Structure 1, $R_1$=$R_2$=$R_3$ methyl; when $Z_1$=Structure 3, $R_1$=$R_2$=$R_3$ methyl; when $Z_1$=Structure 4, $R_1$=$R_2$=$R_3$ methyl; when $Z_1$=Structure 5, $R_1$=$R_2$=$R_3$ methyl; when $Z_1$=structure 7, $R_1$=$R_2$=$R_3$ methyl; when $Z_1$=structure 15, $R_1$=$R_2$=$R_3$ methyl.

In one embodiment, the subject disclosure provides macrocyclic compounds having the structures and definitions set forth in Schemes II-IV, where any or all of the following provisos apply when the macrocycle has Structure I: when $Z_1$=$Z_2$=Structure 1, $Z_3$≠Structure 1; when $Z_1$=$Z_2$=Structure 2, $Z_3$≠Structure 2; when $Z_1$=$Z_2$=Structure 3, $Z_3$≠Structure 3; when $Z_1$=$Z_2$=Structure 6, $Z_3$≠Structure 6; when $Z_1$=$Z_2$=Structure 7, $Z_3$≠Structure 7; when $Z_1$=$Z_2$=Structure 9, $Z_3$≠Structure 9; when $Z_1$=$Z_2$=Structure 11, $Z_3$≠Structure 11; when $Z_1$=$Z_2$=Structure 12, $Z_3$≠Structure 12; when $Z_1$=$Z_2$=Structure 13 when $Q_1$=$Q_2$=H, $Z_3$≠Structure 13 when $Q_1$=$Q_2$=H; when $Z_1$=$Z_2$=Structure 15, $Z_3$≠Structure 15; at most two of $Z_1$, $Z_2$ or $Z_3$=Structure 16 when i) $Q_4$=$Q_5$=t-butyl, ii) $Q_4$=$Q_5$=$OCH_3$, iii) $Q_4$=t-butyl and $Q_5$=$OCH_3$ or iv) $Q_4$=$OCH_3$ and $Q_5$=t-butyl; when $Z_1$=H, $Z_2$≠Structure 1; when $Z_1$=H, $Z_2$≠Structure 7; when $Z_1$=H, $Z_2$≠Structure 9;

when $Z_1$=H, $Z_2$≠Structure 13; when $Z_1$=$Z_2$=Structure 1, $Z_3$≠Structure 15; when $Z_1$=Structure 1 and $Z_2$=H, $Z_3$≠Structure 16 when Q=t-butyl;

where any or all of the following provisos apply when the macrocycle has Structure III: when $Z_1$=Structure 1, $Z_2$≠Structure 1; when $Z_1$=Structure 17, $Z_2$≠Structure 17;

where any or all of the following provisos apply when the macrocycle has Structure IV: when $Z_1$=$Z_2$=$Z_3$=Structure 1, $Z_4$≠Structure 1; when $Z_1$=$Z_2$=$Z_3$=Structure 2, $Z_4$≠Structure 2; when $Z_1$=$Z_2$=$Z_3$=Structure 3, $Z_4$≠Structure 3; when $Z_1$=$Z_2$=$Z_3$=Structure 6, $Z_4$≠Structure 6; when $Z_1$=$Z_2$=$Z_3$=Structure 7, $Z_4$≠Structure 7; when $Z_1$=$Z_2$=$Z_3$=Structure 9, $Z_4$≠Structure 9; when $Z_1$=$Z_2$=$Z_3$=Structure 11, $Z_4$≠Structure 11; when $Z_1$=$Z_2$=$Z_3$=Structure 12, $Z_4$≠Structure 12; when $Z_1$=$Z_2$=$Z_3$=Structure 15, $Z_4$≠Structure 15; when $Z_1$=$Z_2$=$Z_3$=Structure 16, $Z_4$≠Structure 16; when $Z_1$=$Z_2$=$Z_3$=Structure 17, $Z_4$≠$Z_1$, $Z_4$≠Structure 17; when $Z_1$=$Z_2$=$Z_3$=Structure 1, $Z_4$≠H; when $Z_1$=$Z_2$=$Z_3$=Structure 2, $Z_4$≠H; when $Z_1$=$Z_2$=$Z_3$=Structure 3, $Z_4$≠H; when $Z_1$=$Z_2$=$Z_3$=Structure 6, $Z_4$≠H; when $Z_1$=$Z_2$=$Z_3$=Structure 7, $Z_4$≠H; when $Z_1$=$Z_2$=$Z_3$=Structure 17, $Z_4$≠H; when $Z_1$=$Z_2$=H and $Z_3$=Structure 1, $Z_4$≠Structure 1; $Z_1$=$Z_2$=H and $Z_3$=structure 2, $Z_4$ structure 2; when $Z_1$=$Z_2$=H and $Z_3$=Structure 3, $Z_4$≠Structure 3; when $Z_1$=$Z_2$=H and $Z_3$=Structure 6, $Z_4$≠Structure 6; when $Z_1$=$Z_2$=H and $Z_3$=Structure 7, $Z_4$≠Structure 7; when $Z_1$=$Z_2$=H and $Z_3$=Structure 17, $Z_4$≠Structure 17; when $Z_1$=$Z_3$=H and $Z_2$=Structure 1, $Z_4$≠Structure 1; when $Z_1$=$Z_3$=H and $Z_2$=Structure 2, $Z_4$≠Structure 2; when $Z_1$=$Z_3$=H and $Z_2$=Structure 3, $Z_4$≠Structure 3; when $Z_1$=$Z_3$=H and $Z_2$=Structure 6, $Z_4$≠Structure 6; when $Z_1$=$Z_3$=H and $Z_2$=Structure 7, $Z_4$≠Structure 7; when $Z_1$=$Z_3$=H and $Z_2$=Structure 17, $Z_4$≠Structure 17; when $Z_1$=$Z_3$=Structure 6 and $Z_2$=Structure 3, $Z_4$≠$Z_2$; when $Z_1$=$Z_3$=Structure 7 and $Z_2$=Structure 3, $Z_4$≠$Z_2$; when $Z_1$=$Z_3$=Structure 1 and $Z_2$=Structure 3, $Z_4$≠$Z_2$; when $Z_1$=$Z_2$=$Z_3$=Structure 1, $Z_4$≠Structure 3; when $Z_1$=$Z_2$=$Z_3$=Structure 1, $Z_4$≠Structure 17; when $Z_1$=$Z_2$=$Z_3$=Structure 1, $Z_4$≠Structure 6; when $Z_1$=$Z_2$=$Z_3$=Structure 1, $Z_4$≠Structure 7; when $Z_1$=$Z_2$=$Z_3$=Structure 1, $Z_4$≠Structure 9; where any or all of the following provisos apply when the macrocycle has Structure V: when $Z_1$=$Z_2$=Structure 1, $Z_3$≠Structure 1; when $Z_1$=$Z_2$=Structure 3, $Z_3$≠Structure 3; when $Z_1$=$Z_2$=Structure 6, $Z_3$≠Structure 6; when $Z_1$=$Z_2$=Structure 9, $Z_3$≠Structure 9; when $Z_1$=$Z_2$=Structure 17, $Z_3$≠Structure 17; when $Z_1$=Structure 1 and $Z_2$=H, $Z_3$≠Structure 1; when $Z_1$=Structure 3 and $Z_2$=H, $Z_3$≠Structure 3; when $Z_1$=Structure 6 and $Z_2$=H, $Z_3$≠Structure 6;

where any or all of the following provisos apply when the macrocycle has Structure VII: when $Z_1$=Structure 1, $Z_2$≠Structure 1; when $Z_1$=Structure 2, $Z_2$≠Structure 2; when $Z_1$=Structure 6, $Z_2$≠Structure 6;

where any or all of the following provisos apply when the macrocycle has Structure IX: when $Z_1$=Structure 1, $Z_2$≠Structure 1; when $Z_1$=Structure 6, $Z_2$≠Structure 6; $Z_1$=Structure 7, $Z_2$≠Structure 7;

where any or all of the following provisos apply when the macrocycle has Structure X: when $Z_1$=$Z_3$=Structure 1, $Z_2$≠Structure 1; when $Z_1$=$Z_3$=Structure 3, $Z_2$≠Structure 3; when $Z_1$=$Z_3$=Structure 7, $Z_2$≠Structure 7; when $Z_1$=$Z_3$=Structure 1, $Z_2$≠H;

where any or all of the following provisos apply when the macrocycle has Structure XII: when $Z_1$=$Z_2$=$Z_3$=Structure 1, $Z_4$≠Structure 1; when $Z_1$=$Z_2$=$Z_3$=Structure 3, $Z_4$≠Structure 3; when $Z_1$=$Z_2$=$Z_3$=Structure 6, $Z_4$≠Structure 6; when $Z_1$=$Z_2$=$Z_3$=Structure 7, $Z_4$≠Structure 7; when $Z_1$=$Z_2$=$Z_3$=Structure 9, $Z_4$≠Structure 9; when $Z_1$=$Z_2$=$Z_3$=Structure 12, $Z_4$≠Structure 12; when $Z_1$=$Z_2$=$Z_3$=Structure 15, $Z_4$≠Structure 15; when $Z_1$=$Z_2$=$Z_3$=Structure 17, $Z_4$≠Structure 17; when $Z_1$=$Z_2$=$Z_3$=Structure 7, $Z_4$≠H; when $Z_1$=$Z_2$=$Z_3$=Structure 3, $Z_4$≠H; when $Z_1$=$Z_3$=H and $Z_2$=Structure 1, $Z_4$≠Structure 1; when $Z_1$=$Z_3$=H and $Z_2$=Structure 7, $Z_4$≠Structure 7; when $Z_1$=$Z_3$=H and $Z_2$=Structure 14, $Z_4$≠Structure 14; when $Z_1$=$Z_2$=H and $Z_2$=Structure 1, $Z_4$≠Structure 1; when $Z_1$=$Z_2$=$Z_3$=H, $Z_4$≠Structure 7; when $Z_1$=$Z_2$=$Z_3$=H, $Z_4$≠Structure 9; when $Z_1$=$Z_2$=$Z_3$=H, $Z_4$≠Structure 14; when $Z_1$=$Z_2$=$Z_3$=H, $Z_4$≠Structure 17.

In an embodiment, the subject disclosure provides macrocyclic compounds having the structures and definitions set forth in Scheme I with the proviso that when the macromolecule has Structure A, at most two of $Y_1$, $Y_2$ and $Y_3$ is

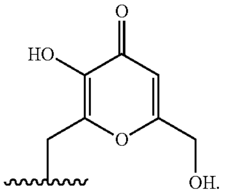 [SMILES: *Cc1oc(CO)cc(=O)c1O]

In certain embodiments, Fe(III) cation is complexed to the macrocyclic compound. In certain other embodiments, Fe(III) cation is not complexed to the macrocyclic compound. The Fe(III) may be complexed to the macrocycle as shown herein.

As previously noted, some pendant donors, such as, for example, carboxylic acid, alcohol, imidazole or pyrazole may deprotonate when complexed with Fe(III). Their corresponding carboxylate ions, imidazolate ions, pyrazolate ions, triazolate ions or oxides (e.g., alkoxide or phenoxide) are within the scope of the disclosure.

In an embodiment, the subject disclosure provides Fe(III) complex comprising Fe(III) complexed with a macromolecule having a structure set forth in Schemes II-IV, as defined in Schemes II-IV.

In another embodiment, the subject disclosure provides Fe(III) complexes comprising Fe(III) complexed with a macromolecule having a structure set forth in Schemes II-IV, as defined in Schemes II-IV, where any or all of the following provisos apply when the macromolecule has Structure I: when $Z_1$=$Z_2$=Structure 1, $Z_3$≠Structure 1; when $Z_1$=$Z_2$=Structure 2, $Z_3$≠Structure 2; when $Z_1$=$Z_2$=Structure 3, $Z_3$≠Structure 3; when $Z_1$=$Z_2$=Structure 4, $Z_3$≠Structure 4; when $Z_1$=$Z_2$=Structure 6, $Z_3$≠Structure 6; when $Z_1$=$Z_2$=Structure 7, $Z_3$≠Structure 7; when $Z_1$=$Z_2$=Structure 11, $Z_3$≠Structure 11; when $Z_1$=$Z_2$=Structure 12, $Z_3$≠Structure 12; when $Z_1$=$Z_2$=Structure 15, $Z_3$≠Structure 15; at most two of $Z_1$, $Z_2$, or $Z_3$=Structure 16 when $Q_4$=$Q_5$=t-butyl, ii) when $Q_4$=$Q_5$=$OCH_3$, iii) when $Q_4$=t-butyl and $Q_5$=$OCH_3$ and iv) when $Q_4$=$OCH_3$ and $Q_5$=t-butyl; $Z_3$≠Structure 16 when $Q_4$=$Q_5$=t-butyl, ii) when $Q_4$=$Q_5$=$OCH_3$, iii) when $Q_4$=t-butyl and $Q_5$=$OCH_3$ and iv) when $Q_4$=$OCH_3$ and $Q_5$=t-butyl; when $Z_1$=$Z_2$=Structure 17, $Z_3$≠Structure 17; when $Z_1$=$Z_2$=Structure 1, $Z_3$≠Structure 15; when $Z_1$=Structure 1 and $Z_2$=H, $Z_3$≠Structure 16 when Q=t-butyl; when $Z_1$=$Z_2$=Structure 15, R methyl; where any or all of the following provisos apply when the macromolecule has Structure IV: when $Z_1$=$Z_2$=$Z_3$=Structure 1, $Z_4$≠Structure 1; when $Z_1$=$Z_2$=$Z_3$=Structure 7, $Z_4$≠Structure 7; when $Z_1$=$Z_2$=$Z_3$=Structure 1, $Z_4$≠Structure 3; when $Z_1$=$Z_2$=$Z_3$=Structure 1, $Z_4$≠Structure 7; when $Z_1$=$Z_2$=$Z_3$=Structure 1, $Z_4$≠Structure 17; when $Z_1$=$Z_2$=$Z_3$=Structure 1, $Z_4$≠H; when $Z_1$=Structure 7, $Z_2$≠Structure 7;

where any or all of the following provisos apply when the macromolecule has Structure XII: when $Z_1$=$Z_2$=$Z_3$=Structure 1, $Z_4$≠Structure 1; when $Z_1$=$Z_2$=$Z_3$=H, $Z_4$≠Structure 1; when $Z_1$=$Z_2$=$Z_3$=H, $Z_4$≠Structure 3; when $Z_1$=$Z_2$=$Z_3$=H, $Z_4$≠Structure 7; where when the macromolecule has Structure XVI and $Z_1$=$Z_2$=$Z_3$=methyl, $Z_4$≠Structure 1.

In an embodiment, Fe(III) complex comprising Fe(III) complexed with a macromolecule having a structure set forth in Scheme I with the proviso that when the macromolecule has Structure A, at most two of $Y_1$, $Y_2$ and $Y_3$ is

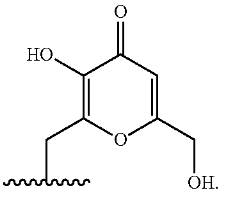 [SMILES: *Cc1oc(CO)cc(=O)c1O]

The Fe(III) complex may have a bound water, hydroxide, or no bound water or hydroxide ligands. However, without being bound by any theory, it is believed that desirable agents have an open coordination site for binding water or anions.

In an embodiment, the subject disclosure provides a macromolecule having a structure set forth in Schemes II-IV, as defined in Schemes II-IV, with the proviso that when the macromolecule has Structure IV and $Z_1$, $Z_2$ and $Z_4$=Structure 1, $Z_3$≠Structure 6. In another embodiment, the subject disclosure provides Fe(III) complex comprising Fe(III) complexed with a macromolecule having a structure set forth in Schemes II-IV, as defined in Schemes II-IV, with the proviso that when the macromolecule has Structure IV and $Z_1$, $Z_2$ and $Z_4$=deprotonated Structure 1, i.e.,

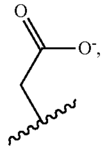

$Z_3$≠Structure 6. In still another embodiment, the subject disclosure provides Fe(III) complex comprising Fe(III) complexed with a macromolecule having a structure set forth in Schemes II-IV, as defined in Schemes II-IV, with the proviso that when the macromolecule has Structure IV and $Z_1$, $Z_2$ and $Z_4$=deprotonated Structure 1, $Z_3$ deprotonated Structure 6, i.e.,

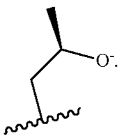

In yet another embodiment, the subject disclosure provides a macromolecule having a structure set forth in Schemes II-IV, as defined in Schemes II-INT, with the proviso that when the macromolecule has Structure IV and $Z_1$=$Z_2$=$Z_3$=deprotonated Structure 1, $Z_4$≠$Z_1$.

Certain pendants may have more than one N or O donor atom (e.g., pyrazole or imidazole, carboxylate or carboxylic acid) although generally only one is coordinated to metal ion.

A macrocyclic compound can have various pendant groups and combinations of pendant groups. When more than one pendant donor is present, they may be the same or different.

In various examples, the macrocyclic core has 1, 2, 3, or 4 nitrogen atoms, 1, or 2 oxygen atoms and/or 1, or 2 sulfur atoms. For example, the macrocyclic core has 6, 7, 8, 9, or 10 carbons. For example, the macrocyclic core has from 9 to 16 atoms, including all ranges and integers there between, where at least one of the atoms in the macrocyclic core is a heteroatom, such as N. In another embodiment, at least two of the atoms in the macrocyclic core are heteroatoms, such as, for example, N. In various examples, there are 2, 3, 4, or 5 carbon atoms separating the heteroatoms in the macrocyclic core. The one or more carbons in the macrocyclic core can be unsubstituted (e.g., $—CH_2—$) or substituted (e.g., —CHR—, or $—CR_2—$, where the R groups are, for example, alkyl groups or aryl groups (e.g., benzyl groups) as described herein), provided that at least one carbon in the macrocyclic core is substituted with a pendant donor. For example, they can be substituted with the substituents disclosed herein. In another embodiment, the macrocyclic core comprises at least two heteroatoms, each of which is independently N or O, which are separated from each other by at least two carbon atoms.

The pendant groups can be covalently attached to a macrocyclic core (e.g. at a nitrogen): especially for cyclen (III), cyclam (VII), TACN (I).

Macrocyclic compounds can be macrocyclic ligands. The macrocyclic ligands described herein stabilize the trivalent iron (Fe(III)) state. The coordination geometry is designed for desirable binding of Fe(III) in comparison to Fe(II) to maintain the Fe(III) oxidation state, for example, under biologically relevant conditions. Stabilization of the Fe(III) state (e.g., $E_o$<0 mV vs. NHE) also serves to inhibit the production of reactive oxygen species that occur through reduction to the Fe(II) state of the complex.

It is desirable that the Fe(III) center is stabilized relative to Fe(II) so that there is no reaction with biological reductants to produce reactive oxygen species (ROS) (see, e.g., FIG. 11). Such redox-inactive (under biological conditions) Fe(III) centers have negative redox potentials versus NHE. Examples of macrocyclic complexes of the present with macrocyclic core and pendant groups that produce stabilized Fe(III) include, but are not limited to, 1,4,9-triazacyclononane macrocyclic core and alcohol pendent groups that become deprotonated upon binding of Fe(III) (see, e.g., FIG. 6).

In various examples, a macrocyclic compound or compound of the present disclosure exhibits a reduction potential ($E_o$) of less than 0 mV vs. normal hydrogen electrode (NHE) in aqueous solution at a biologically relevant pH (e.g., a pH of 6.5-7.5 or 7.2-7.4, including all 0.1 pH values and ranges therebetween). In various other examples, a macrocyclic compound or compound of the present disclosure exhibits a reduction potential ($E_o$) of at least −100, at least −150, at least −200, at least −300, at least −400, at least −500, or at least −600 mV vs. normal hydrogen electrode (NHE) in aqueous solution at a biologically relevant pH (e.g., a pH of 6.5-7.5 or 7.2-7.4, including all 0.1 pH values and ranges therebetween). In various other examples, a macrocyclic compound or compound of the present disclosure exhibits a reduction potential ($E_o$) of less than 0 to −600 mV vs. normal hydrogen electrode (NHE) in aqueous solution at a biologically relevant pH (e.g., a pH of 6.5-7.5 or 7.2-7.4, including all 0.1 pH values and ranges therebetween).

Figure 1:
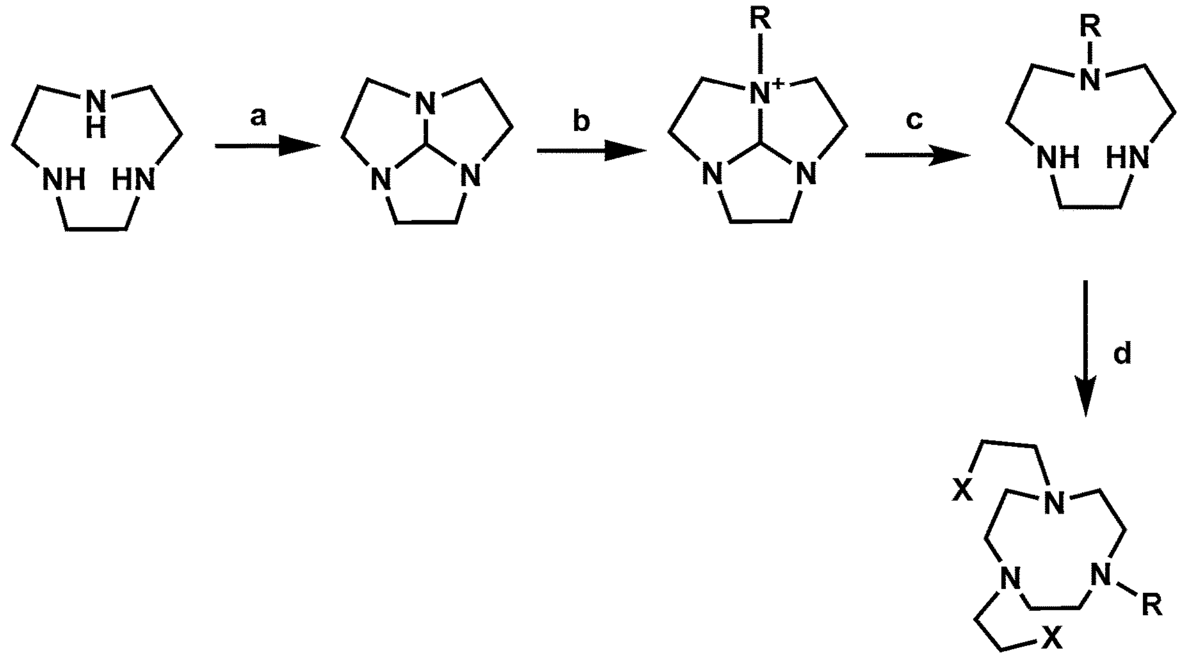
FIG. 1 shows general synthesis of TACN (1,4,7-triazacyclononane) derivatives. a) N,N-Dimethylformamide Dimethylacetal, Toluene/Chloroform 4:1. b) R-X; R=Benzyl, methyl, propargyl, methylphenyl, methyl-benzoate, 2-(2-methoxy-ethoxy)ethane, 4-(methyl)-1,1'-biphenyl, Benzyl methyl ether; Dry THF and X=chloro, bromo or iodo c) Reflux; 12M HCl/MeOH 1:1 OR KOH solution, then extraction with chloroform. d) Addition of coordinating pendents by addition of chloro or bromomethyl derivatives of coordinating pendents such as bromomethyl-pyrazole, or bromoacetamide. Addition of pendents by reductive amination by addition of aldehyde with reducing agent such as imidazole-2-carboxaldehyde. Addition of pendents by addition of $H_2O$/ethanol mixture and (S)-(−) propylene oxide or (R)-(+)propylene oxide.

The shortening of the $T_1$ relaxation times of the protons of water by the Fe(III) complexes, $T_1$ relaxivity, is promoted by both innersphere water and outersphere water interactions. Accordingly, in various examples, macrocyclic complexes and compounds of the present disclosure comprise one or more pendant donor groups that can hydrogen bond to water through heteroatoms such as, for example, oxygen or nitrogen (see, e.g., FIG. 1).

Non-limiting examples of such pendant donor groups are pendent alcohol groups that deprotonate to alkoxide groups (see, e.g., FIGS. 2, 3, 4, and 7). In addition, in various examples, macrocyclic compounds and compounds of the present disclosure comprise an open coordination site, which may bind water (see, e.g., FIGS. 5 and 6). These water ligands may ionize to form hydroxide ligands at neutral pH (see, e.g., FIGS. 8 and 9), for example, as shown by, pH-potentiometric titrations (see, e.g., FIG. 12). It may desirable that the water ligands are rapidly exchanging. Rate constants for innersphere water exchange is dependent on both the magnetic field strength of the scanner and also on the rotational correlation time of the contrast agent which is related to size. For clinical MRI scanners with field strengths of 3 Tesla, the following is desirable. In various examples, for a molecule with a rotational correlation time of about 1-4 nanoseconds, the exchange rate constant for the contrast agents is from $10^5$ $s^{-1}$ to $10^9$ $s^{-1}$ or greater than $2\times10^5$ $s^{-1}$. In various examples, for a molecule with a rotational correlation time of about 0.1 to 0.2 nanoseconds, the exchange rate constant for the contrast agents is from $10^6$ $s^{-1}$ to $10^9$ $s^{-1}$. Evidence for rapidly exchanging water ligands is shown by variable temperature $^{17}O$ NMR spectroscopy studies (see, e.g., FIG. 10). The reduced transverse relaxation times ($T_{2r}$) is approximated by measurement of the linewidth of the $^{17}O$ resonance.

Coordination chemistry of Fe(III) is dependent on the coordination number. The macrocyclic compounds of the present disclosure have donor groups which can be part of the macrocyclic core, also referred to as macrocycle donors, and donor groups can be part of the substituents (e.g., pendant groups) on the macrocyclic core, also referred to as pendant donors. When Fe(III) is complexed to a macrocyclic compound of the present disclosure, 4 to 7 donors are complexed to the metal ion center. In an embodiment, the macrocyclic core can have from 2 to 4 donors and from 2 to 4 pendant donors. In various embodiments, there are 2 macrocycle donors and 3 pendant donors, 2 macrocycle donors and 4 pendant donors, 3 macrocycle donors and 2 pendant donors, 3 macrocycle donors and 3 pendant donors, 3 macrocycle donors and 4 pendant donors, 4 macrocycle donors and 2 pendant donors, 4 macrocycle donors and 3 pendant donors.

Examples of suitable macrocyclic compounds include:

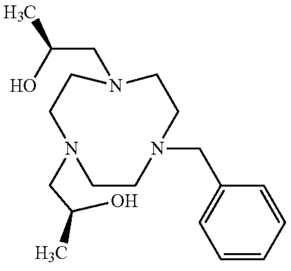,

TOB

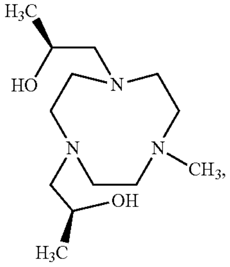,

TOM

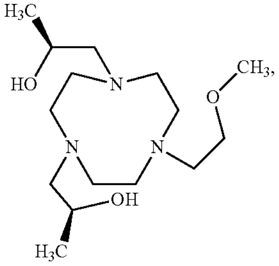,

TOP

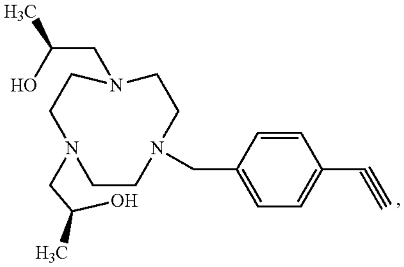,

TOBAC

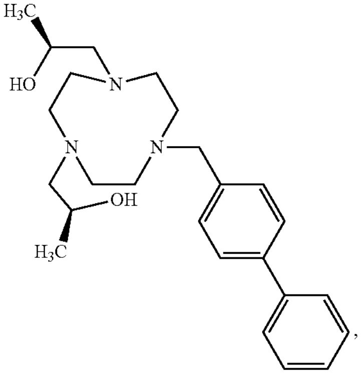,

TOBI

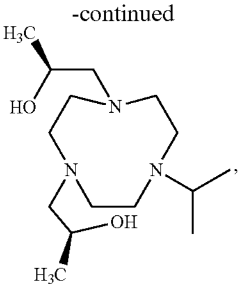
TOPI
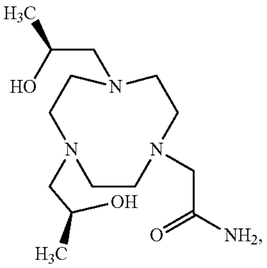
TOA
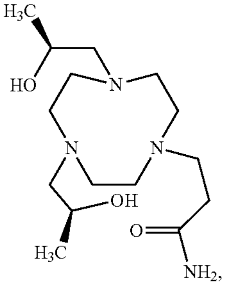
TOPID
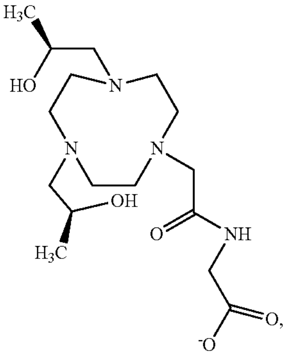
TOAG
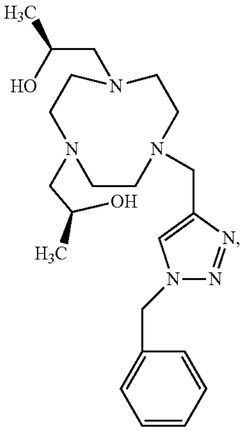
TOTzB
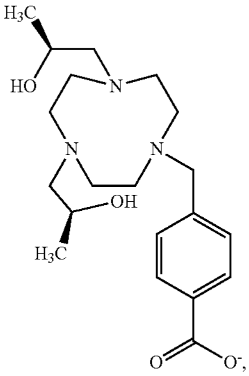
TOBA
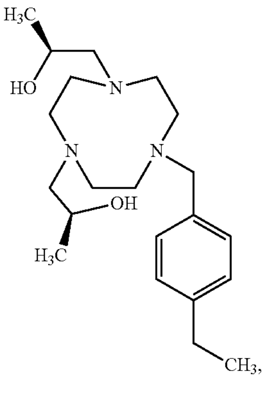
MeoxyBz -continued
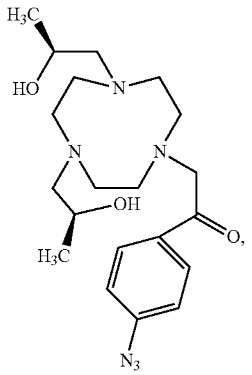
TOCBA
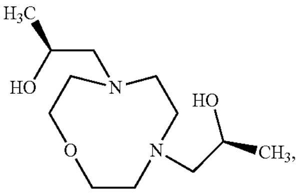
(HPN2O)
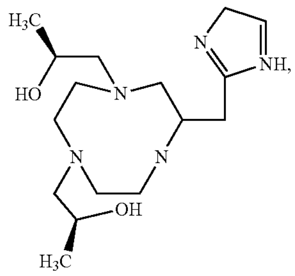
TOI
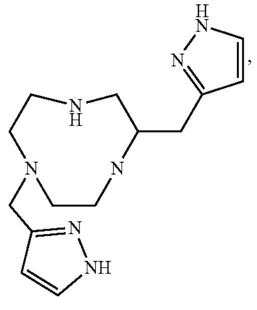
TBP
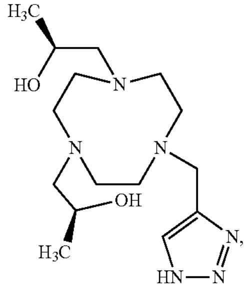
TOTO
-continued
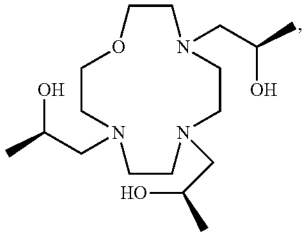
(HPN3O)
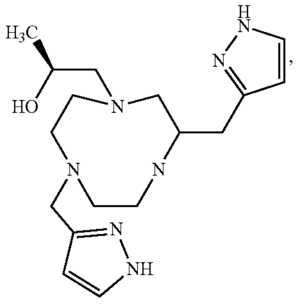
TOBP
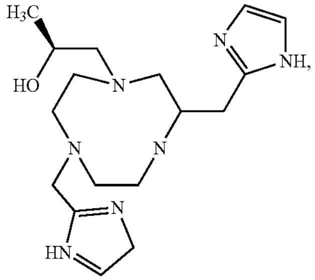
TOBIM
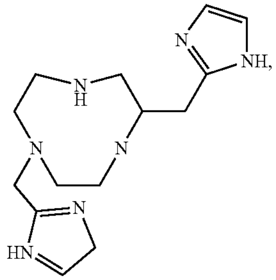
TBI
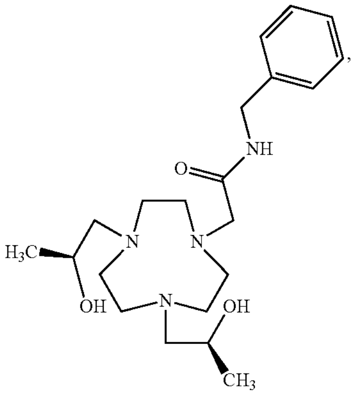
TOPID -continued

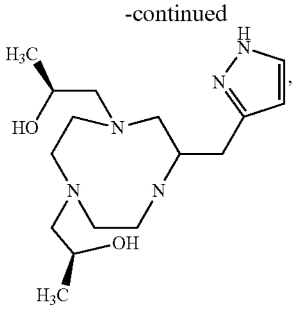

, and

TOPy

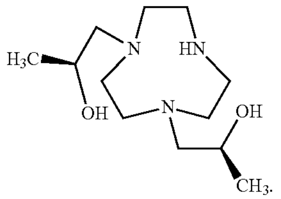

TON

In an embodiment, the compounds of the present disclosure can have more than one macrocyclic core tethered together (i.e., covalently bound) via a linker group (e.g., aromatic groups), one or more macrocyclic compound of the present disclosure, a polymer, a dendrimer, or peptide.

It is desirable to produce an oligomeric molecule with a rotational correlation time of approximately 1 to 4 nanoseconds for effective contrast agent at field strengths of 3 Tesla to 7 Tesla. For example, linking three macrocyclic Fe(III) complexes together, e.g. through the functionalized benzene by using click chemistry (shown below), is expected to produce a compound (and produces a compound for the compound shown below) that will have a rotational correlation time which has a value which is intermediate between a macrocyclic complex, such as, for example, Fe(TACO) and a molecule linked or bound to a large protein.

Linkers may have multiple fused aromatic groups such as, for example, anthracene, or carbazole or linked through the nitrogens of triazacyclononane or tetraazacyclododecane. There may be a direct attachment to the macrocyclic nitrogen donor of the contrast agent (e.g., as shown below) or there may be an intervening methylene group (e.g., as shown for $Fe_2$(DT-meta)).

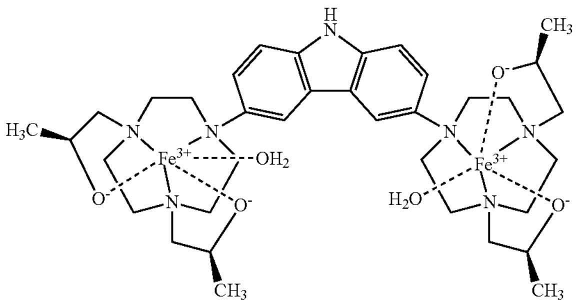

Linkers may have one or more coordinating groups or be non-coordinating.

One or more macrocyclic compound may be covalently bound to a protein, such as, for example, human serum albumin, which is the predominant protein in the blood. This approach is considered to slow the rotational correlation time and increase the relaxivity of the tethered macrocyclic compound(s) (e.g., at field strengths of 3 Tesla) and to increase the residency time of the contrast agent in the blood.

Peptides may be used to link (tether) two or more iron complexes together. In this approach, the complexes are, for example, linked through the carboxy or amino terminus of the peptide. A peptides may have one or more sequences that allow for targeting to other biopolymers such as, for example, fibrin targeting peptides.

A compound may be a dendrimer with a plurality of pendant macrocyclic complexes. For example, dendrimers based on ethylenediamine cored PAMAM dendrimers will be prepared where PAMAM is polyamidoamine with 4 up to 36 chelates. The iron complexes will be attached either through click chemistry or by coupling of carboxylic acid group to the terminal amines of the PAMAM.

Polymeric contrast agents may be made by, for example, using click chemistry as described for the complexes containing triazole linkers or, alternatively, by radical polymerization (as shown below). In this approach, a styrene functionality is put in place of a benzyl group and the macrocyclic ligand is incorporated into the polymer. This approach is also amenable with macrocyclic compounds such as, for example, the TOB type TACN macrocyclic compound.

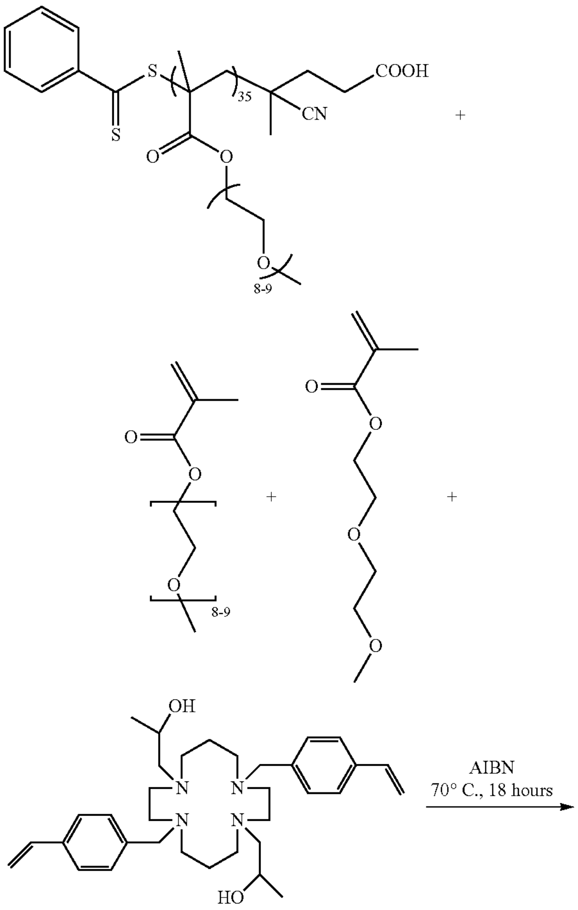

-continued

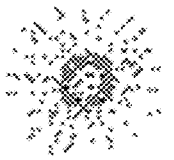

In the above reaction, the resulting polymer may be reacted with a source of Fe(III), such as, for example, $FeCl_3$, to provide a compound of the present disclosure that can be used as an MRI contrast agent.

For tumor uptake and retention, the size of the molecule containing the contrast agent is important. In addition, given that the magnitude of the $T_1$ relaxivity increases proportionally with the number of iron complexes and also increase with the size of the molecule, or more precisely the rotational correlation time ($\tau_c$), the use of multiple tethered macrocyclic complexes should increase contrast. This can be accomplished by the formation of dimeric or oligomeric Fe(III) complexes with three macrocyclic compounds as shown below. For example, the compound can have the following structures:

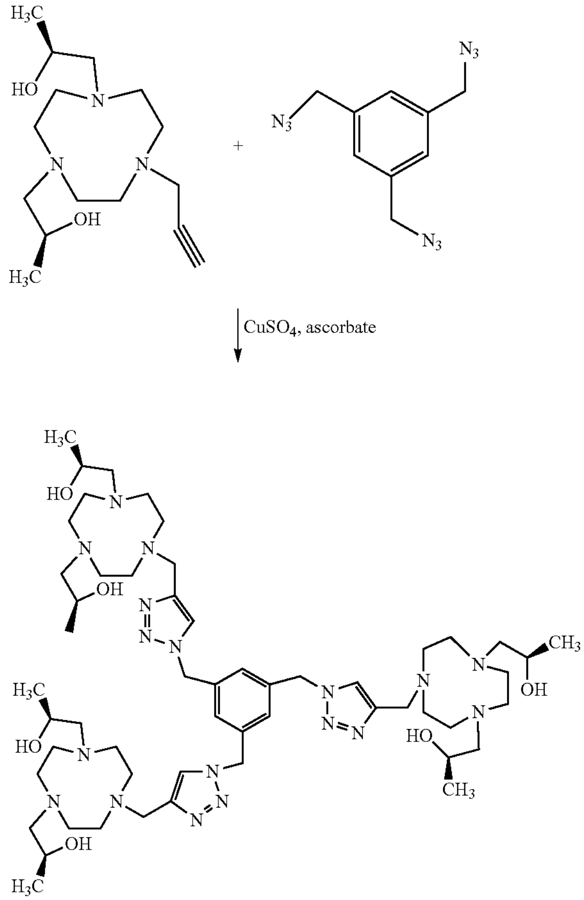

Alternatively, the macrocyclic compounds may be linked in the following manner to form dinuclear complexes in scheme below.

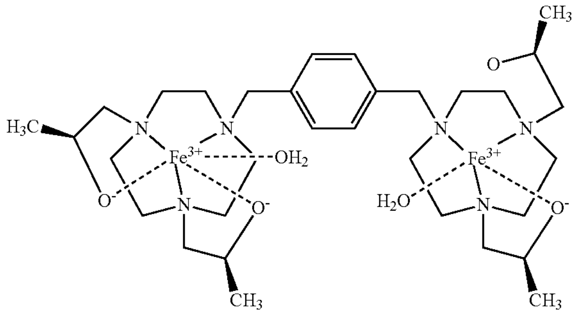

$Fe_2$(DT-para)

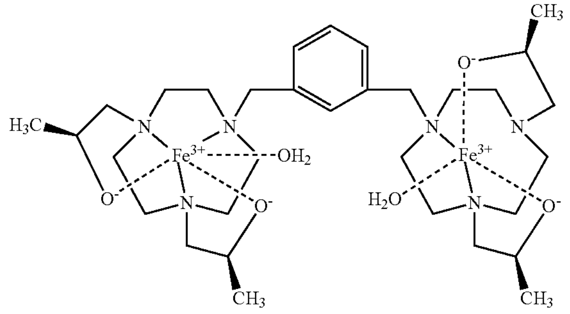

$Fe_2$(DT-meta)

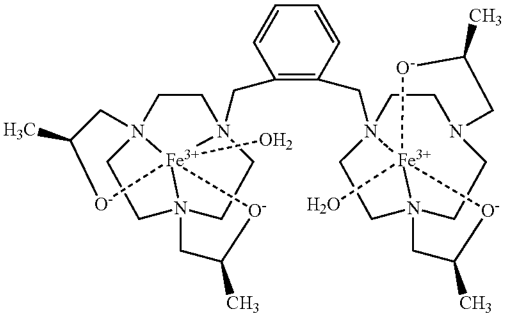

$Fe_2$(DT-ortho)

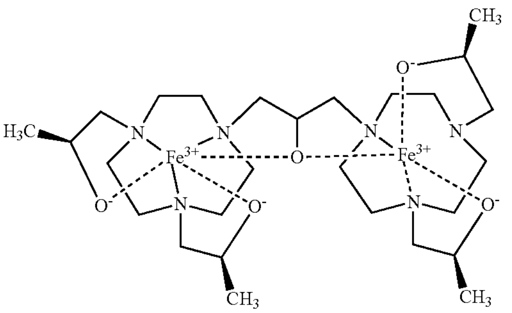

$Fe_2$(TONO)

Alternatively, the complex can be attached to a polymeric structure (e.g., water-soluble polymers such as, for example, polyesters, polylactides, polylactide-polystryene copolymers, and the like), for example, as shown below by using click chemistry.

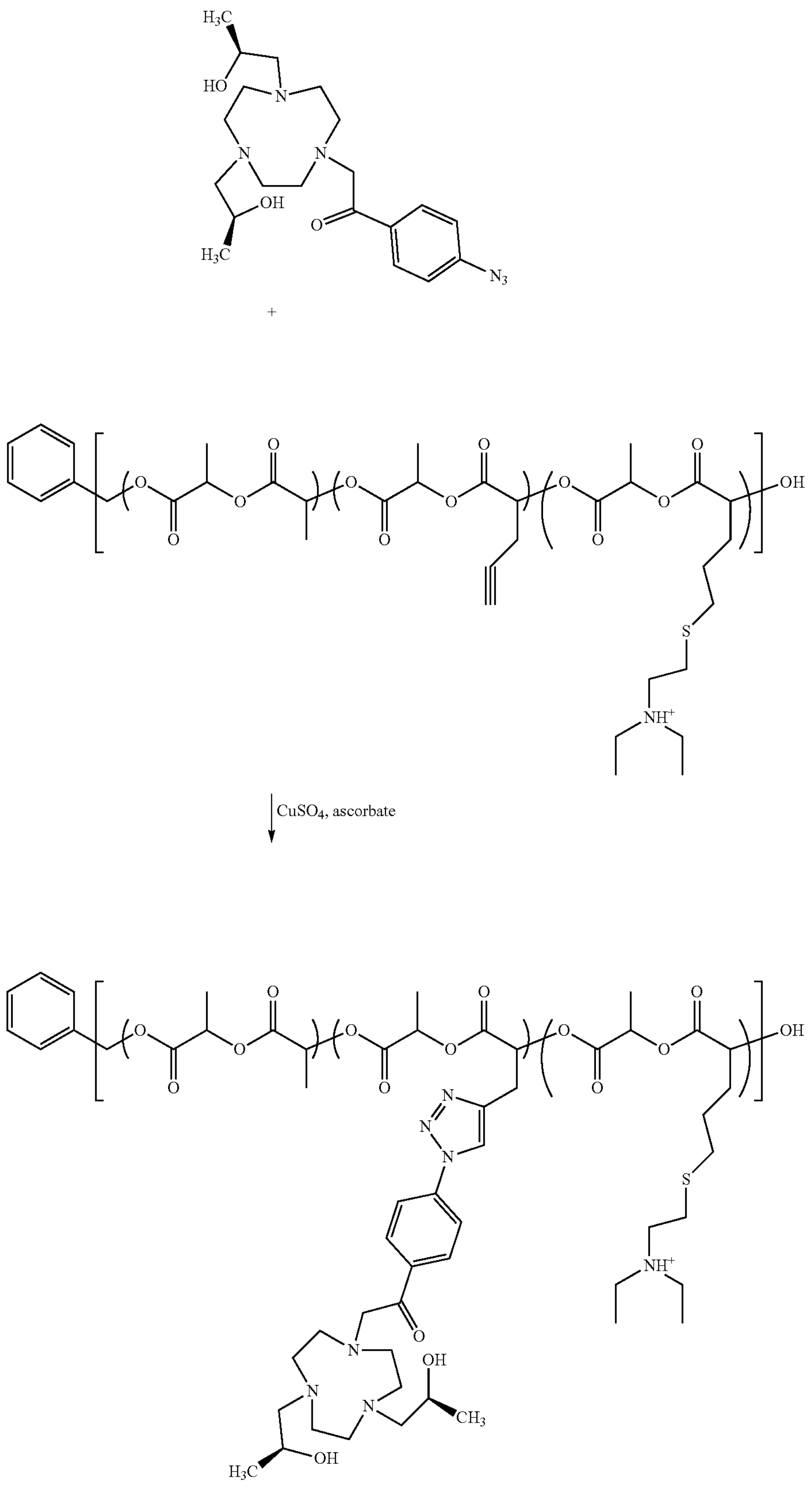
CuSO4, ascorbate

The following are examples of Fe(III) complexes, and are within the scope of the disclosure.

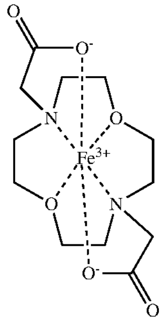

Fe(NODAC)

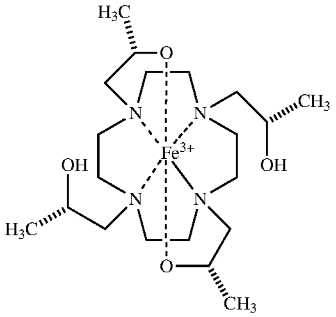

Fe(STHP)

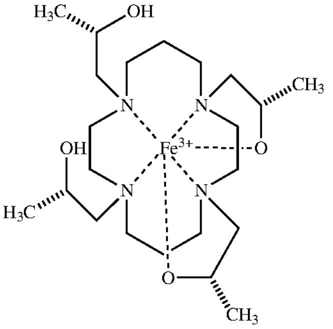

Fe(STHC)

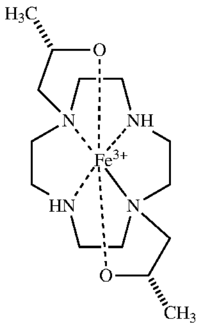

Fe(GUAC)

In various embodiments, the macrocyclic compounds, macrocyclic complexes, or compounds of the disclosure are a salt, a partial salt, a hydrate, a polymorph, or a stereoisomer, or a mixture thereof. For example, the macrocyclic compound, macrocyclic complex, or compound is present as a racemic mixture, a single enantiomer, a single diastereomer, or mixture of diastereomers. In certain embodiments, after complexation of the metal ion, the macrocyclic complexes or compounds are present as mixtures of diastereomers and/or conformers which can be determined by NMR. The diastereomers may arise from the conformation of the macrocyclic core and the directionality of the substituents on the macrocyclic core.

The compounds of the disclosure can have innersphere water or alternatively, a hydroxide ligand. In an embodiment the compounds have one innersphere ligand (q) which contributes to relaxivity as in Eq. 1.

$$R_1 = R_1^{SS} + R_1^{IS} \quad \text{Equation 1}$$

$$R_1^{IS} = \frac{q/[\mathrm{H_2O}]}{T_{1m} + \tau_m} \quad \text{Equation 2}$$

Eq. 1 shows that relaxivity has contributions from bound water (innersphere, IS) and second-sphere (SS) (outersphere) water. Eq. 2 predicts that greater numbers of bound water molecules and rapid ligand exchange rate constants (short lifetimes for bound water (Tm)) are advantageous. Notably $r_1$, the parameter used to characterize relaxivity, has units of $mM^{-1}s^{-1}$, and is obtained from a plot of $T_{1_{obs}}$ ($s^{-1}$) versus contrast agent concentration. There is an analogous relationship for second-sphere waters although the number and residence time is not well defined. The $R_1$ and $R_2$ relaxivity (from $T_1$ and $T_2$ relaxation rate constants at 4.7 T at 37° C. is shown for several complexes in FIG. 13 and FIG. 14. Data on a 3 Tesla MRI scanner are shown in FIG. 21. Table 1 summarizes $R_1$ and $R_2$ relaxivity data for several Fe(III) complexes.

TABLE 1

$T_1$ Relaxivity of Fe(III) complexes at neutral pH, Hepes buffer, 37° C. on a 4.7 Tesla MRI scanner. HSA is human serum albumin.

| Complex | $R_1$ ($mM^{-1}s^{-1}$) | $R_1$ ($mM^{-1}s^{-1}$) with HSA | $R_2$ ($mM^{-1}s^{-1}$) | $R_2$ with HSA |
|---|---|---|---|---|
| Fe(GUAC) | 0.015 | 0.41 | 1.05 | 6.5 |
| Fe(NOKA) | 2.0 | 2.5 | 4.8 | 1.3 |
| Fe(TACO) | 1.3 | 1.4 | 1.7 | 2.0 |
| Fe(TOB) | 2.5 | 3.4 | 4.3 | 4.9 |
| Fe(STHP) | 0.074 | 0.53 | 1.2 | 3.9 |
| Fe(TOM) | 0.45 | 1.3 | 2.7 | 2.5 |

Structures of certain complexes in Table 1.

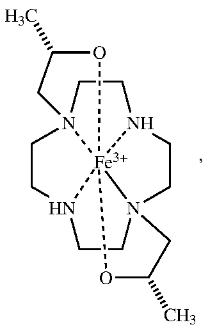

,

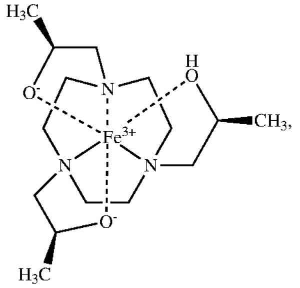

Fe(GUAC) Fe(TACO)

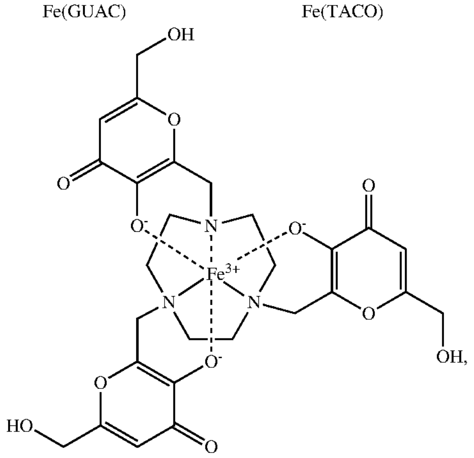

Fe(NOKA)

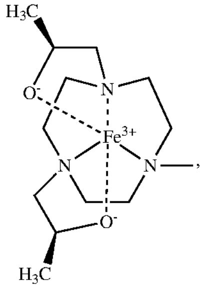

, and

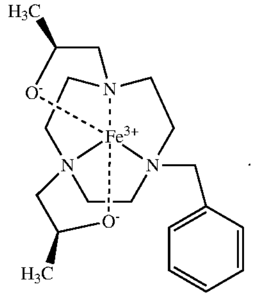

.

Fe(TOM) Fe(TOB)

It is desirable that the ratio of the $T_1$ to $T_2$ relaxivity ($R_1/R_2$) of a macrocyclic complex or compound of the present disclosure are close to one (unity). $R_2$, the transverse relaxivity, is by definition always larger than $R_1$, the longitudinal relaxivity. In various examples, Fe(III) contrast agents of the present disclosure have desirably low $R_2$ to give $R_1/R_2$ ratios close to one, for example, as shown in Table 1. In various examples, a macrocyclic complex or compound of the present disclosure have $R_1/R_2$ ratios of 0.5 to 0.2 or 0.8 to 0.6. These data demonstrate the desirability of the TACN ligand, alcohol pendents and an open coordination site, for example, in Fe(TOB) or Fe(MeOxyBz) in comparison to certain complexes with no open coordination site for the mononuclear complexes such as Fe(AmBz), or Fe(TOTO). (see, e.g., Table 2).

TABLE 2

$T_1$ relaxivity at 4.7 T, 37° C., at pH 7.4, 100 mM NaCl, 37° C. with 6 mM human serum albumin (HSA).

| | Complex alone | Complex + HSA |
|---|---|---|
| Fe(MeOxyBz) | 2.3 | 3.13 |
| Fe(AmBz) | 0.80 | 1.23 |
| Fe(TOTO) | 0.56 | 1.13 |
| Fe(ToTzB) | 0.87 | 1.09 |
| Fe(TON) | — | 0.93 |
| $Fe_2$(DT-meta) | — | 2.91 |
| $Fe_2$(DT-ortho) | — | 3.60 |
| $Fe_2$(TONO) | — | 1.10 |

Structures of certain complexes in Table 2.

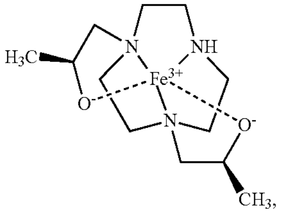

Fe(TON)

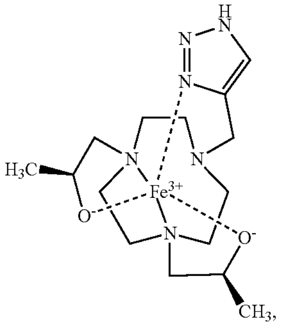

Fe(ToTz)

-continued

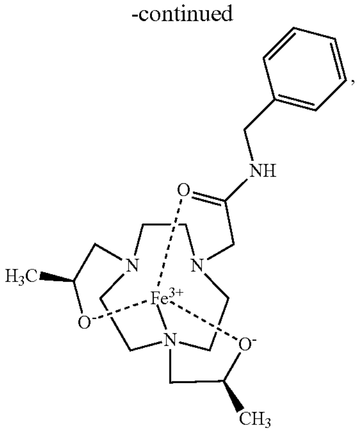

Fe(AmBz)

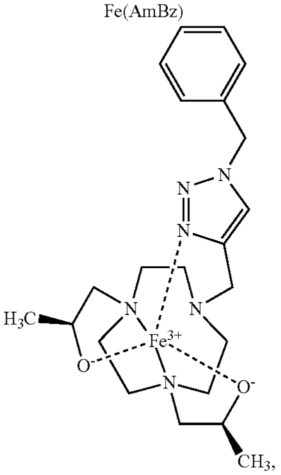

Fe(ToTzB)

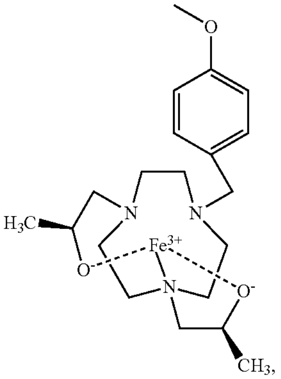

Fe(MeoxyBz)

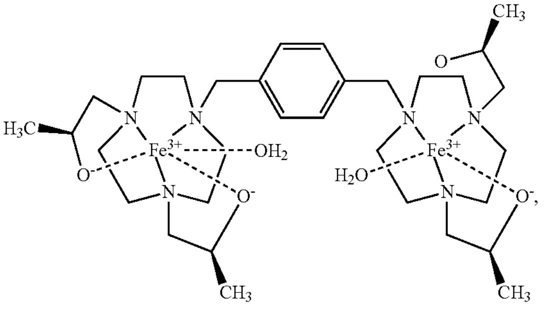

$Fe_2$(DT-para)

-continued

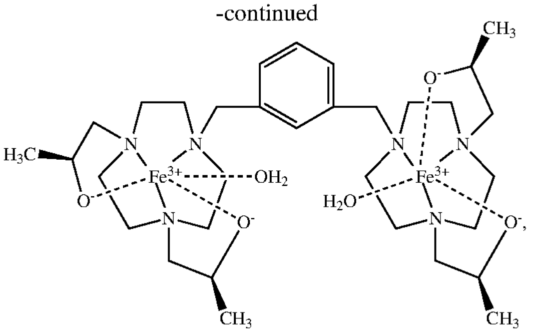

$Fe_2$(DT-meta)

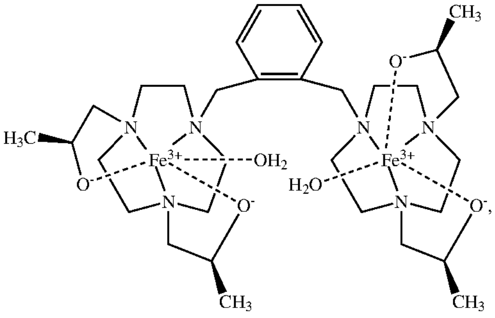

, and $Fe_2$(DT-ortho)

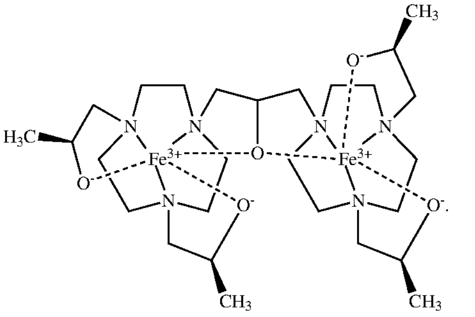

.

$Fe_2$(TONO)

Tables 1 and 2 show that desirable interaction of the Fe(III) complex with water molecules can enhance relaxation of the protons of the water. Without being bound by any particular theory, it is considered that exchange of innersphere water with bulk water is an important mechanism for proton relaxivity.

This shows that optimization of the interaction of the Fe(III) complex with water molecules to enhance relaxation of the protons of the water is important. Without being bound by any theory, exchange of innersphere water with bulk water is thought to be a dominant mechanism for proton relaxivity in Gd(III) complexes. However, Fe(III) is a much smaller metal ion than Gd(III) (0.78 Å vs. 1.25 Å, respectively). The shorter M–H distance in bound water of Fe(III) compared to Gd(III) suggests that the relative efficiency of the outersphere versus innersphere contributions may differ for the two metal ion complexes.

There are three mechanisms that contribute to paramagnetic relaxation of associated water ($1/T_{1m}$): the scalar (contact) contributions, dipole-dipole contributions and Curie spin relaxation. The most important of these for the longitudinal relaxation considered here is the dipole-dipole contribution ($1/T_1DD$). At field strengths of 1.5 T or greater, $1/T_1DD$ is defined as shown in Eq. 3 where S is the spin quantum number, $\omega_H$ is the Larmor frequency of the proton, $r_{MH}$ is the metal ion-proton distance and $\gamma_H$ is the proton gyromagnetic ratio, ge is the electronic g factor, $\mu_B$ is the Bohr magneton, and $\mu_o$ is the permittivity of a vacuum. Notably, the $1/T_1DD$ term increases (higher relaxivity) with larger total spin (S) which favors Gd(III) over Fe(III). However, the shorter distance of the paramagnetic Fe(III) center to water protons ($r_{MH}$) favors Fe(III) proton relaxation, especially given the $1/r^6$ dependence.

$$\frac{1}{T_1^{DD}} = \frac{2}{15}\left(\frac{\mu_0}{4\pi}\right)\frac{\gamma_H^2 g_e^2 \mu_B^2 S(S+1)}{r_{MH}^6}\left[\frac{3\tau_c}{1+\omega_H^2\tau_c^2}\right] \qquad \text{Equation 3}$$

$$\frac{1}{\tau_c} = \frac{1}{\tau_R} + \frac{1}{T_{1e}} + \frac{1}{\tau_m} \qquad \text{Equation 4}$$

The correlation time ($\tau c$) for the dipolar relaxation mechanism is influenced by different processes including the lifetime of the bound water ($1/\tau_m$), the rotational motion of the contrast agent ($1/\tau_R$) and the longitudinal relaxation of the unpaired electrons ($1/T_{1e}$). Although any of these three processes can contribute, their importance depends on the strength of the magnetic field. Much of the literature is focused on the importance of these processes at low field strength (<1 T). Under these conditions, the rotational processes or electronic relaxation times may be limiting, and $\tau_m$ should be in a narrow range close to 10 ns ($k_{ex}=10^8\ s^{-1}$). However at higher field strengths (≥1.5 T), simulations show that the optimal $\tau_m$ has a larger range (1-100 ns) and rotational motions should have values intermediate between small molecules and proteins. An important parameter is $T_{1e}$, the electronic relaxation time. A long $T_{1e}$ for Fe(III) may result from complexes that have a high degree of symmetry, leading to little zero field splitting and slow relaxation of the electronic state. Also, the coordination sphere needs to favor high spin (S=5/2) and not low spin S=½ Fe(III).

Studies to determine whether a metal complex has a bound water can involve the collection of variable temperature $^{17}O$ NMR data. The data were obtained using a Varian 400 MHz NMR spectrometer with a broad band probe (FIG. 10). Since the $^{17}O$ isotope has a low natural abundance, each complex was dissolved into a solution of water enriched with $H_2{}^{17}O$ such that the peak measured by the NMR would be larger and therefore easier to detect visually. NMR studies were performed at various temperatures for each complex studied. The temperature ranges for each compound tested were between 10° C. and 80° C., or 283K and 353K. In order to obtain the desired complex solubility of 45 mM for these measurements, the pH range studied was 3-5. The temperature dependent transverse relaxation data were fit to various equations via a least squares fit analysis using Scientist for Windows version 3.0. First, it is known that complexes with an open coordination site, obey the Swift-Connick equation, as shown in equation 5a:

$$\frac{1}{T_{2r}} = \frac{\pi}{P_m} * (\Delta v_{observed} - \Delta v_{solvent}) = \qquad \text{Equation 5a}$$

$$\frac{1}{\tau_m} * \frac{\left(T_{2m}^{-1} + T_{2m}^{-1} * \tau_m^{-1} + \Delta\omega_m^2\right)}{\left(T_{2m}^{-1} + \tau_m^{-1}\right)^2 + \Delta\omega_m^2} + \frac{1}{T_{2os}} \text{ where } \frac{1}{T_{2r}}$$

is the reduced transverse relaxation rate, $P_m$ is the molar fraction of bound water and $(\Delta v_{observed}-\Delta v_{solvent})$ is the difference in line widths between $H_2{}^{17}O$ with and without complex present. Since the observed line widths can be measured using NMR spectroscopy, and $P_M$ can be calculated in advance, they are the measurable quantities in the equation. In addition, $$\frac{1}{\tau_m}$$

is residence time of the bound water molecules, $T_{2m}{}^{-1}$ is the transverse relaxation rate of the bound water and $\Delta\omega_m$ is the chemical shift difference between bound and bulk water. The $T_{2OS}$ is a term taking into account the hydrogen bonding of ligand atoms to bulk water.

In the complexes studied at the temperature ranges in which data were recorded and analyzed, $$T_{2m}^{-1} \text{ and } \frac{1}{T_{2os}}$$

can be neglected and the Swift-Connick equation is reduced to equation 5b. In conjunction, since reduced transverse relaxation rates are often quite large, taking the natural logarithm of both sides of the equation allows for better scaling and simpler representation of the data, as shown in equation 5c:

$$\frac{1}{T_{2r}} = \frac{\pi}{P_m} * (\Delta v_{observed} - \Delta v_{solvent}) = \frac{1}{\tau_m} * \frac{\Delta\omega_m^2}{\tau_m^{-2} + \Delta\omega_m^2}. \quad \text{Equation 5b}$$

$$\ln\left(\frac{1}{T_{2r}}\right) = \ln\left(\frac{1}{\tau_m} * \frac{\Delta\omega_m^2}{\tau_m^{-2} + \Delta\omega_m^2}\right). \quad \text{Equation 5c}$$

The inverse bound water residence time, and the chemical shift difference between bound and bulk water are each represented by equations 6a and 6b, respectively:

$$\frac{1}{\tau_m} = k_{ex} = \frac{k_b * T}{h} * \exp\left(\frac{\Delta S^{\ddagger}}{R} - \frac{\Delta H^{\ddagger}}{RT}\right). \quad \text{Equation 6a}$$

$$\Delta\omega_m = \frac{g_L \mu_b S(S+1)B}{T}\left(\frac{A}{\hbar}\right). \quad \text{Equation 6b}$$

In equation 6a, $k_{ex}$ is the water exchange rate constant at the coordination site and is the inverse of the bound water residence time. $k_b$ is Boltzmann's constant, h is Planck's constant, T represents absolute temperature, $\Delta S^{\ddagger}$ and $\Delta H^{\ddagger}$ represent the activation entropy and enthalpy, respectively. In equation 6b, $g_L$ is the isentropic Lande factor, $\mu_b$ is the magnetic moment, S represents the total spin state, B represents the applied magnetic field, and $$\left(\frac{A}{\hbar}\right)$$

represents the hyperfine coupling constant. In equation 6b, the isentropic Lande factor, magnetic moment, spin state, magnetic field, and hyperfine coupling constant terms are consolidated into a single parameter which is solved for in the treatment of the data. This consolidation reduces equation 6a to a simple inverse temperature dependence and the simplified constant is represented by the constant C. This approach was used to determine the exchange rate constants for the bound water of Fe(TOB) as shown in FIG. 10 of $2\times10^6$ $s^{-1}$.

The macrocyclic compounds of the present disclosure are thermodynamically stable and/or kinetically inert towards dissociation. In an embodiment, the macrocyclic compounds are thermodynamically stable and kinetically inert towards dissociation. In an embodiment, the kinetic inertness of the macrocyclic compounds of the present disclosure can be described using a rate constant for dissociation. In an embodiment, the macrocyclic donors and pendant donors do not dissociate appreciably from the metal center (e.g., 1% or less, 0.1% or less, or 0.01% or less dissociation is observed) for up to 24 hours at neutral pH in the presence of 1) 25 mM carbonate, 0.40 mM phosphate, 100 mM NaCl, pH 7.2; 2) pH 4, 100 mM NaCl; or 3) with 5-fold excess $ZnCl_2$, 100 mM NaCl, pH 7.2.

In an embodiment, Fe(III) is high-spin S=5/2. For effective $T_1$ (longitudinal) relaxation, a paramagnetic spin state is needed. In order to keep Fe(III) in the high-spin state, the ligand (or crystal) field splitting must not be too large. If the crystal field splitting is larger than the pairing energy, a low spin (S=1/2) state will result. Fe(III) is readily maintained in a high-spin paramagnetic state with a range of ligand donor groups, especially containing anionic oxygen donors.

Examples of desirable macrocyclic complexes and compounds are shown below. These Fe(III) complexes may have an open coordination site for a water ligand, two alcohol pendants and a third pendant which is sterically bulky. Ancillary pendant groups such as, for example, aryl groups (e.g., benzyl groups and substituted benzyl groups, such as, for example, methoxy-benzyl groups, and fused ring aryl groups) or alkyl groups (e.g., branched alkyl groups) are particularly effective. Some may have two or more Fe(III) centers such as $Fe_2$(DT-para). The coordinatively saturated complexes, Fe(ToTzB) and Fe(AmBz) have relatively high relaxivity that may be enhanced by attachment of larger ancillary pendants to slow rotational correlation times.

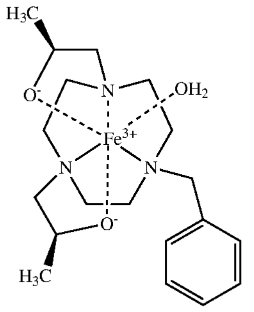

Fe(TOB)

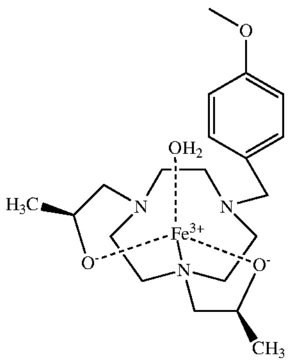

Fe(MeoxyBz)

-continued

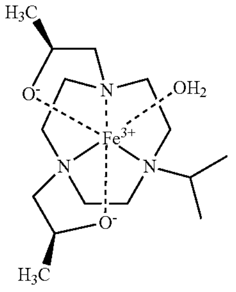

Fe(TOPI)

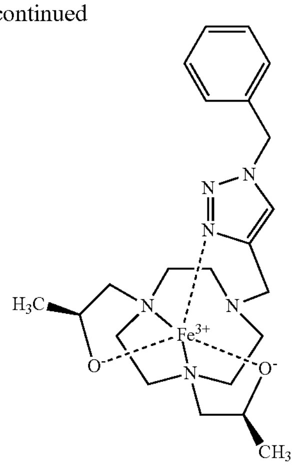

Fe(ToTzB)

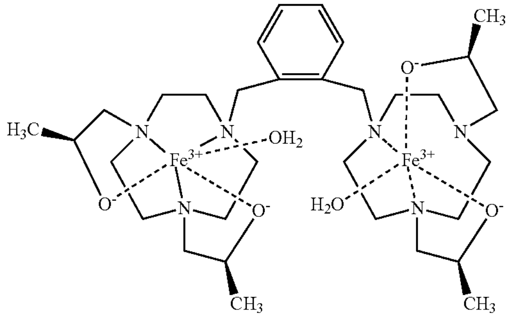

$Fe_2$(DT-ortho)

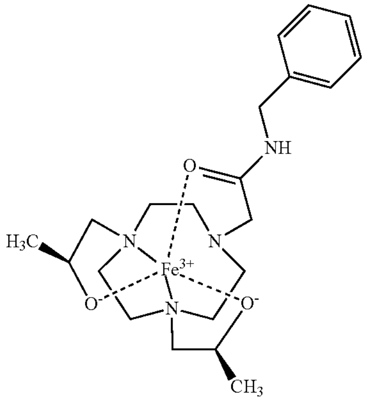

Fe(AmBz)

It is desirable that the electronic relaxation time of the high-spin Fe(III) center is sufficiently long (e.g., greater than $3\times10^{11}$ s), that it is not the limiting factor in the correlation time constant as expressed in equation 4 at field strengths of 1.5 Tesla or greater. This can be accomplished by, for example, using macrocyclic ligands that produce high symmetry at the Fe(III) center such as, for example, Fe(TACO), Fe(NOKA), and Fe(TOB). It is desirable that the zero field splitting factor (D) is small given that $(T_{1e})^{-1}$ is directly proportional to $D^2$ for high-spin Fe(III) complexes in an axially distorted complex.

It is desirable that the Fe(III) complex remain in the trivalent oxidation state and not be reduced by, for example, peroxide, superoxide, ascorbate, or by glutathione at concentrations present in the extracellular medium of cells such as, for example, mammalian cells (e.g., human cells). Normally, a redox potential more negative than zero mV (<0 mV) versus NHE is sufficient. If the complex were to be reduced to Fe(II) and the Fe(II) complex and the complex has a positive redox potential versus NHE, reactive oxygen species may be produced, for example, as shown in FIG. 8. For example, [Fe(EDTA)]—has a redox potential of approximately 300 mV and produces ROS as shown by the assay in FIG. 11.

For use in methods of the disclosure, the compounds described herein can be administered as pharmaceutical preparations. Accordingly, they can be provided in a variety of compositions, and can be combined with one or more pharmaceutically acceptable carriers. Some examples of pharmaceutically acceptable carriers can be found in: *Remington: The Science and Practice of Pharmacy* (2005) 21st Edition, Philadelphia, PA Lippincott Williams & Wilkins. The composition can be provided as a liquid, a solution, or a solid, and may be provided in combination with any suitable delivery form or vehicle, examples of which include but are not limited to caplets, capsules, tablets, an inhalant or aerosol, etc.

Various methods known to those skilled in the art may be used to introduce the compositions of the disclosure to an individual. These methods include but are not limited to intravenous, intramuscular, intracranial, intrathecal, intradermal, subcutaneous, and oral routes. In an embodiment, the composition is administered intravenously.

The necessary solubility of the complexes depends on their effectiveness in producing contrast. For Fe(III) $T_1$ contrast agents that have good relaxivity, the complexes need 100 μM-2 mM solubility. However, other additives such as human serum albumin (has) or meglumine may be used to increase solubility and/or increase relaxivity. Addition of HSA (e.g., 35 mg/mL) to some of the Iron(III) complexes produces higher $T_1$ relaxivity as shown in Table 1 and 2). Solubility is generally measured in aqueous solution at near neutral pH (e.g., 6.5 to 7.5, including all 0.1 pH values and ranges therebetween) in 100 mM NaCl with 25 mM carbonate and 0.4 mM phosphate. The dose of the composition to be used will necessarily be dependent upon the needs of the individual to whom the composition of the disclosure is to be administered. These factors include, but are not necessarily limited to the weight, age, sex, and medical history of the individual. Shown in FIGS. 15, 16, 17, 18, 19, 20 are data from in vivo MRI studies done in mice. The contrast agent, Fe(TOB) was injected at 0.20 mL of 6.3 mM Fe-TOB-HSA (10.5 mg of HAS or two equivalents of megluamine). $T_1$ relaxivity differences in tissue over a 30 minute period show that the highest signal is observed in the kidney cortex. A second in vivo study carried out with Fe(NOKA) shows that a contrast agent that lacks a water ligand does not perform as well in vivo. Fe(TOB) also produces contrast of brain tumors in mice (FIG. 20).

In an aspect, the present disclosure provides imaging methods using the macrocyclic complexes and compounds described herein. The imaging methods use magnetic resonance imaging methods. Non-limiting examples of such methods include, Magnetic Resonance Imaging (MRI).

Specifically, the macrocyclic compounds of the present disclosure, which are complexed to Fe(III), can be used as $T_1$ MRI contrast agents. These complexes may have properties that change with alterations in pH. Such properties make these complexes useful for mapping pH to enable better therapeutic treatment of diseases such as, for example, cancer, stroke and heart disease.

The imaging methods of the present disclosure can be used to image a cell, tissue, organ, vasculature, or a part thereof. The cell, tissue, organ, vasculature can be a part of an individual. By "individual" it is meant a human or non-human animal (e.g., cow, pig, mouse, rat, cat, dog, or other agricultural, pet, or service animal, and the like). In an embodiment, the disclosure provides a method to obtain an image of at least a portion of a cell, tissue, organ, or vasculature comprising the steps of: contacting a cell, tissue, organ, or vasculature with the compounds of the present disclosure, and imaging at least a portion of the cell, tissue, organ, or vasculature to obtain an image of the portion of cell, tissue, organ, or vasculature. At least part of a cell, tissue, or organ can be alive or dead. Likewise, the individual can also be alive or deceased.

In an embodiment, the macrocyclic complex compound is used as a Fe(III) $T_1$ MRI contrast agent. This contrast is produced by $T_1$ weighted imaging to give positive contrast in the region where the iron complexes accumulate. The complexes are high-spin Fe(III) under biologically reducing conditions with either innersphere and/or outersphere water interactions that give a decrease in the $T_1$ relaxation times of bulk water protons.

In this application, the use of the singular form encompasses the plural and vice versa.

The macrocyclic compounds of the present disclosure can be prepared, for example, as described in the Experimental Details. The following examples are presented to illustrate the present disclosure. They are not intended to be limiting in any manner. Those skilled in the art will recognize that routine modifications to these embodiments can be made which are intended to be within the scope of the disclosure.

The following Statements describe various examples of macrocyclic compounds, macrocyclic complexes, compounds, and compositions of the present disclosure, and uses thereof:

Statement 1. A macrocyclic compound of the present disclosure comprising: a macrocyclic core of the present disclosure (e.g., a macrocyclic core comprising from 9 to 15 atoms, where at least one of the atoms in the macrocyclic core is a N atom, at least two carbon atoms separate a heteroatom selected from the group consisting of: N atom, O atom, or S atom) and one or more pendant groups of the present disclosure, where the one or more pendant groups are substituents on (e.g., covalently bound to) the macrocyclic core (e.g., one or more pendant groups having the following structure:

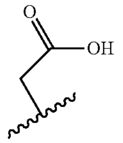
1

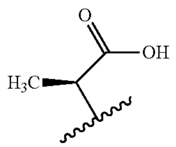
2

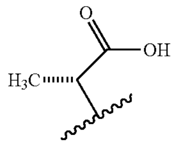
2′

-continued

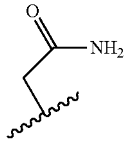
3

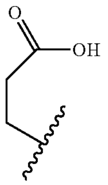
4

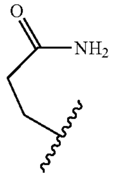
5

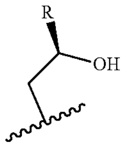
6

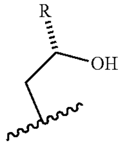
6′

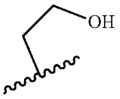
7

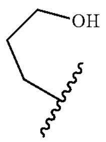
8

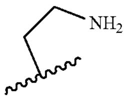
9

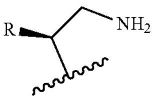
10

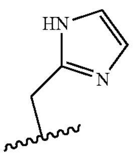
11

-continued

12

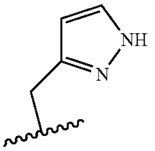

13

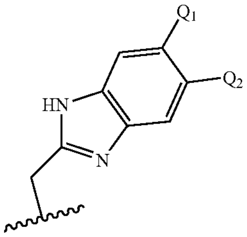

14

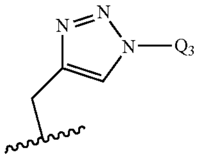

15

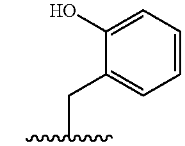

16

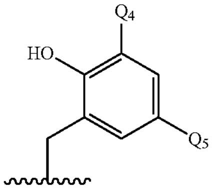

17

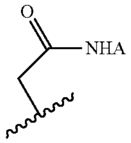

18

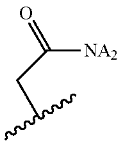

19

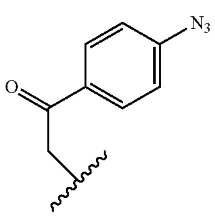

or an anionic (e.g., deprotonated) analog thereof or a stereoisomer thereof, where $Q_1$ and $Q_2$ are each independently H, $OCH_3$, $CO_2H$, or $CH_2CO_2G_4$, $G_4$ is H, $C_1$ to $C_{12}$ substituted or unsubstituted alkyl groups of linear or branched structure or PEG group $(—CH_2CH_2O—)_n$ (n=1-12), $Q_3$ is H, $C_1$ to $C_{12}$ substituted or unsubstituted alkyl groups of linear or branched structure or PEG group $(—CH_2CH_2O—)_n$ (n=1-

12), $Q_4$ and $Q_5$ are each independently H, $OCH_3$, $CO_2H$, or substituted or unsubstituted alkyl groups of linear or branched structures, A is a substituted or unsubstituted alkyl group of linear or branched structure with $C_1$ to $C_{12}$ or is a substituted or unsubstituted aryl group, or an amino acid, a salt, a partial salt, a hydrate, a polymorph, or a stereoisomer thereof.

Statement 2. A macrocyclic complex comprising a high-spin Fe(III) cation complexed to a macrocyclic core is a macrocyclic compound of the present disclosure (e.g., a macrocyclic compound according to Statement 1), and/or at least one pendant group substituent of the macrocyclic compound, or a salt, a partial salt, a hydrate, a polymorph, or a stereoisomer thereof, where the macrocyclic compound exhibits a negative redox potential (e.g., a redox potential of less than 0 vs. normal hydrogen electrode (NHE) in aqueous (e.g., water) solution at a biologically relevant pH (e.g., 6.5-7.5 or 7.2-7.4)).

Statement 3. A macrocyclic compound or complex according to Statements 1 or 2, where at least one or all of the one or more pendant groups is covalently bound to a N on the macrocyclic core.

Statement 4. A macrocyclic complex according to Statements 2 or 3, where the macrocyclic complex has at least one open coordination site.

Statement 5. A macrocyclic complex according to any one of Statements 2-4, where the macrocyclic complex has at least one water or at least one hydroxide complexed to the high-spin Fe(III) cation.

Statement 6. A macrocyclic compound or macrocyclic complex according to any one of Statements 1-5, where at least one of the pendant groups is substituted at a benzylic position or any carbon the alkyl group leading to the heteroatom of the pendant group.

Statement 7. A macrocyclic compound or macrocyclic complex according to any one of Statements 1-6, where the macrocyclic core is a cyclen moiety, a cyclam moiety, or TACN moiety.

Statement 8. A macrocyclic complex according to any one of Statements 2-4, where the macrocyclic complex comprises a TACN moiety and at least one (e.g., one or two) anionic pendant groups.

Statement 9. A macrocyclic complex according to Statement 8, where the anionic pendants are individually chosen from carboxylate pendants, imidazolate pendants, pyrazolate pendants, alkoxide pendants, and phenoxide pendants.

Statement 10. A macrocyclic complex according to Statement 8 or 9, where the macrocyclic complex further comprises a coordinating pendant group or a non-coordinating pendant.

Statement 11. A macrocyclic compound or macrocyclic complex according to any one of Statements 1-10, where the macrocyclic core has one of the following structures:

A

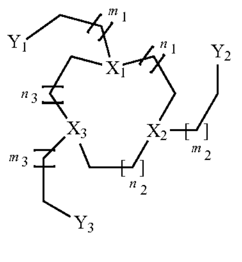

-continued
B
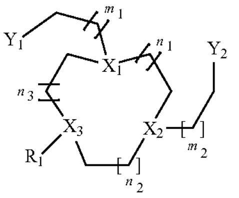
C
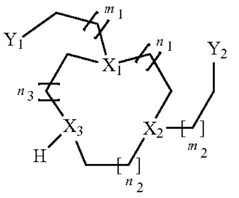
D
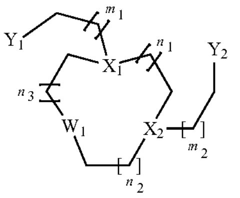
E
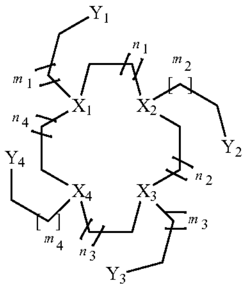
F
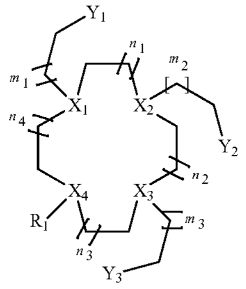
G
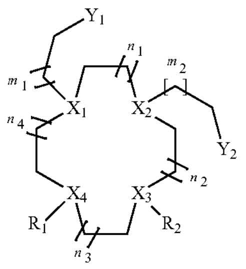
-continued
H
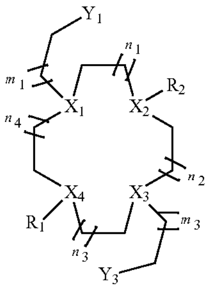
I
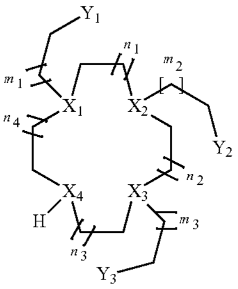
J
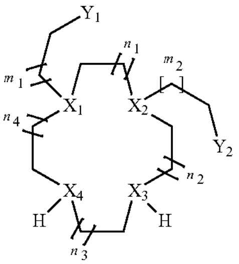
K
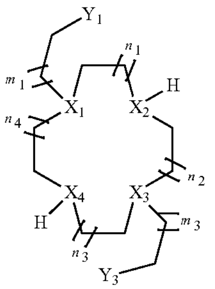
L
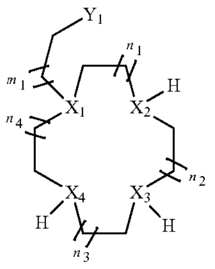

-continued

M

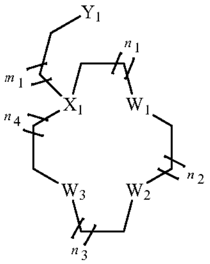

N

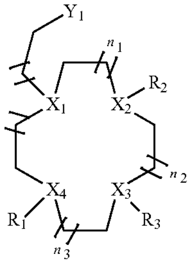

O

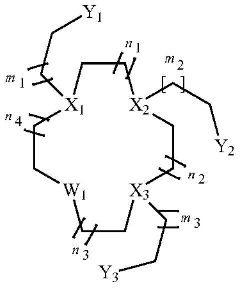

P

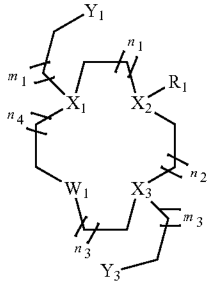

Q

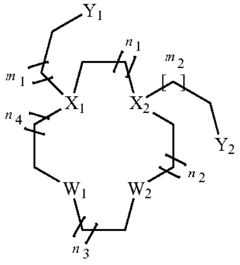

-continued

R

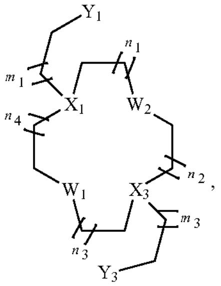

where $X_1$, $X_2$, $X_3$, and $X_4$ are N; $W_1$, $W_2$, and $W_3$ are each independently O or S; $Y_1$, $Y_2$, $Y_3$, and $Y_4$ are each independently pendant donors comprising N, where N has a lone pair of electrons (e.g., amino, benzimidazole, imidazole, aniline, pyrazoyl, triazole, benzotriazole), or a pendant donor comprising O, where O has at least one lone pair of electrons but preferably two or three lone pairs (e.g., ketone, alcohol, alkoxide, carboxylic acid, amide, phenol or phenoxide, or a deprotonated form of the foregoing, such as a carboxylate ion, an imidazolate ion, a pyrazolate ion or an oxide, including, for example, an alkoxide or a phenoxide); $m_1$, $m_2$, $m_3$, and $m_4$ are each independently 0, 1, or 2; $n_1$, $n_2$, $n_3$, and $n_4$ are each independently 1 or 2; and $R_1$, $R_2$, and $R_3$ are each independently substituted or unsubstituted aryl, substituted or unsubstituted heteroaryl or substituted or unsubstituted alkyl group, where $R_1$, $R_2$, and $R_3$ are not substituted by a pendant donor, where the alkyl segment of the alkyl-Y chain (alkyl-$Y_1$, alkyl-$Y_2$, alkyl-$Y_3$ and/or alkyl-$Y_4$) may each independently be substituted (e.g., Structure a or Structure b) or unsubstituted (Structure c or Structure d). For Structures a-f, the pendent may have either R or S configuration at the chiral carbon:

a

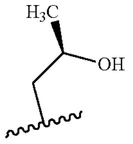

b

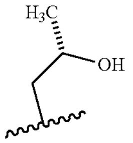

c

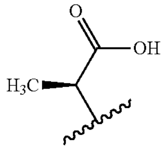

d

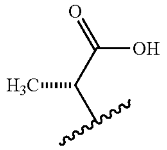

-continued
e
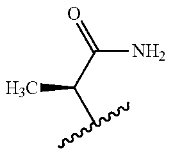
f
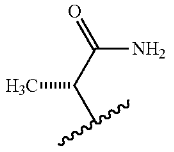
Statement 12. A macrocyclic compound or complex according to any one of Statements 2-11, where the macrocyclic core has the following structure:
Scheme II
(I)
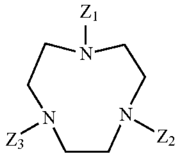
(II)
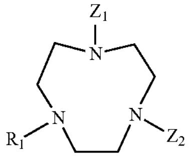
(III)
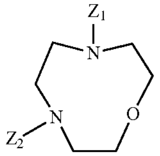
(IV)
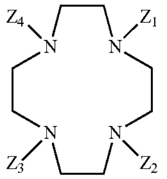
(V)
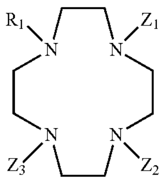
(VI)
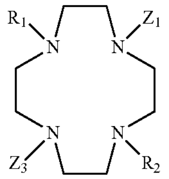
-continued
(VII)
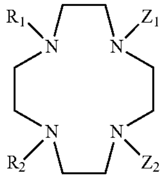
(VIII)
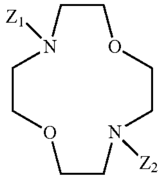
(IX)
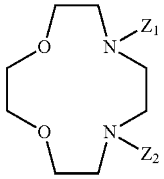
(X)
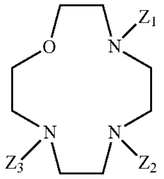
(XI)
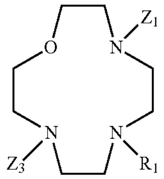
(XII)
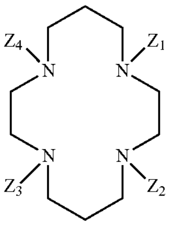
(XIII)
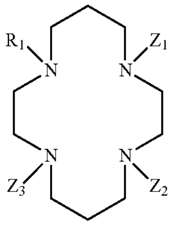
(XIV)
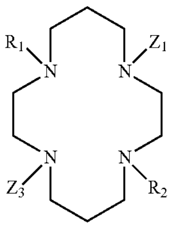

-continued (XV)

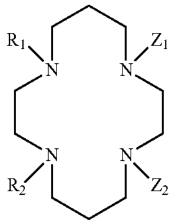

(XVI)

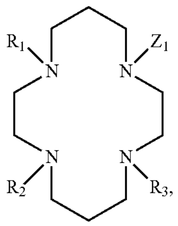

where $R_1$, $R_2$, and $R_3$ each independently=substituted or unsubstituted aryl, substituted or unsubstituted heteroaryl or substituted or unsubstituted alkyl group, where $R_1$, $R_2$, and $R_3$ are not substituted by pendant donors; and when the macrocycle has Structure I, $Z_1$=H or one of the pendant groups in Scheme III and $Z_2$ and $Z_3$ each independently=one of the pendant groups in Scheme III;

when the macrocycle has Structure II, III, VII, VIII, IX or XV, $Z_1$ and $Z_2$ each independently=one of the pendant groups in Scheme III; when the macrocycle has Structure VI, XI or XIV, $Z_1$ and $Z_3$ each independently=one of the pendant groups in Scheme III;

when the macrocycle has Structure XVI, $Z_1$=one of the pendant groups in Scheme III; when the macrocycle has Structure IV, $Z_4$=one of the pendant groups in Scheme III and $Z_1$, $Z_2$ and $Z_3$ each independently=H or one of the pendant groups in Scheme III, provided that at most two of $Z_1$, $Z_2$ and $Z_3$=H;

when the macrocycle has Structure V, $Z_1$ and $Z_2$ each independently=H or one of the pendant groups in Scheme III and $Z_3$=one of the pendant groups in Scheme III;

when the macrocycle has Structure X, $Z_1$ and $Z_3$ each independently=one of the pendant groups in Scheme III and $Z_2$=H or one of the pendant groups in Scheme III; when the macrocycle has Structure XII, $Z_4$=one of the pendant groups in Scheme III and $Z_1$, $Z_2$ and $Z_3$ each independently=H or one of the pendant groups in Scheme III, provided that at most two of $Z_1$, $Z_2$, and $Z_3$=H;

when the macrocycle has Structure XIII, $Z_1$ and $Z_3$ each independently=one of the pendant groups in Scheme III and $Z_2$=H or one of the pendant groups in Scheme III; where for all Structures I-XVI, each of $Z_1$, $Z_2$, $Z_3$ and $Z_4$, as applicable, are selected independently of each other.

Statement 13. A macrocyclic compound or complex according to any one of Statements 2-12, where the macrocyclic core has the following structure:

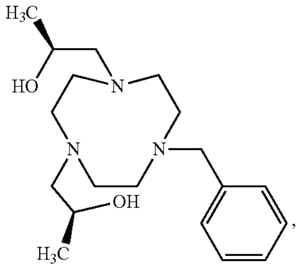

TOB

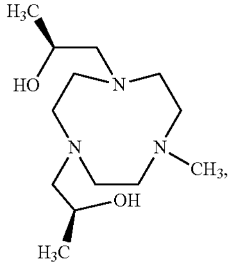

TOM

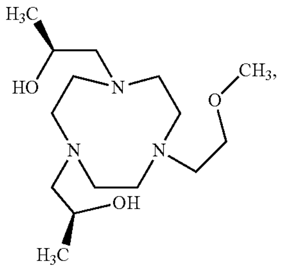

TOP

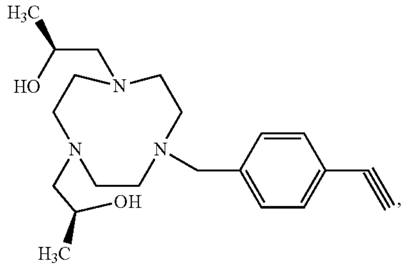

TOBAC

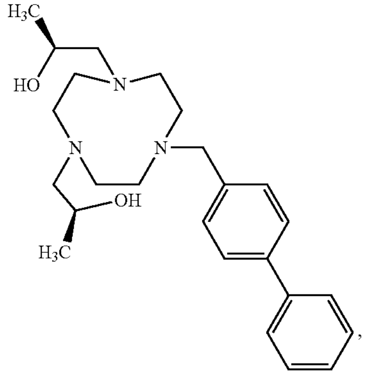

TOBI

-continued
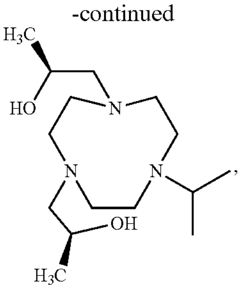
TOPI
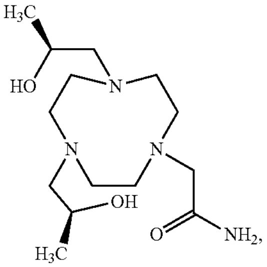
TOA
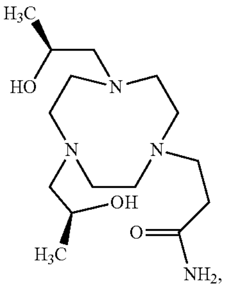
TOPID
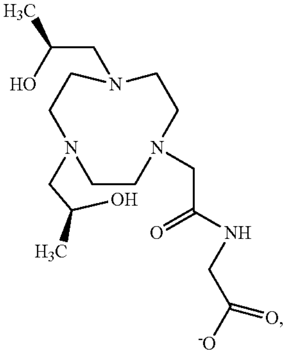
TOAG
-continued
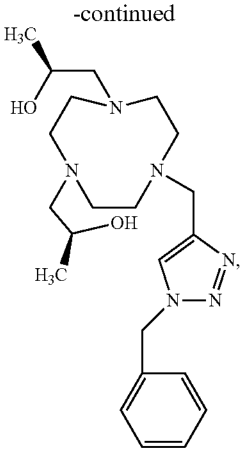
TOTzB
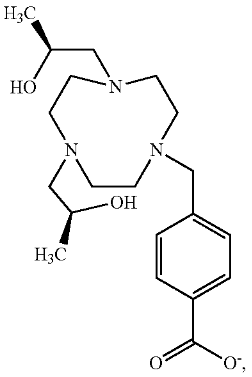
TOBA
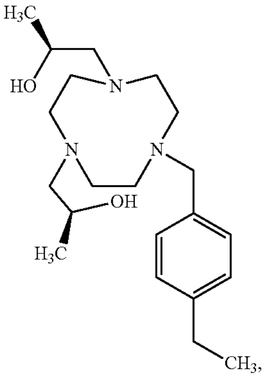
MeoxyBz -continued
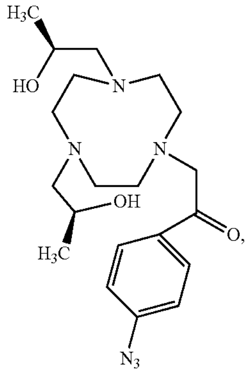
TOCBA
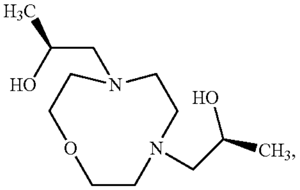
(HPN2O)
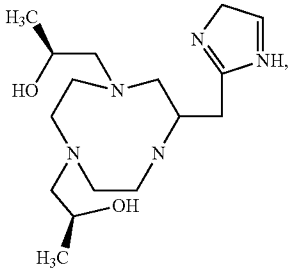
TOI
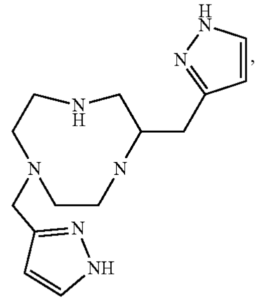
TBP
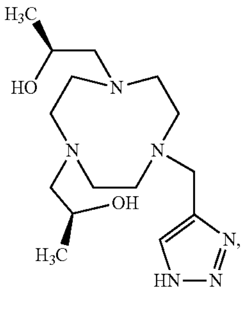
TOTO
-continued
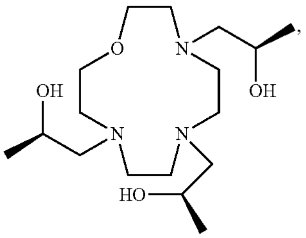
(HPN3O)
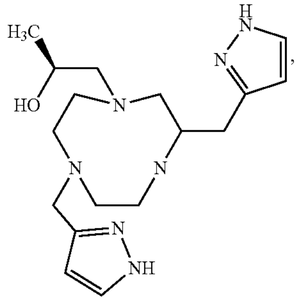
TOBP
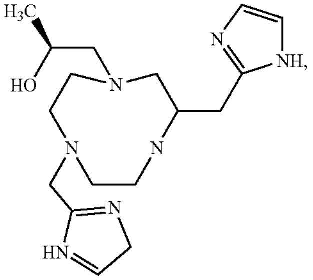
TOBIM
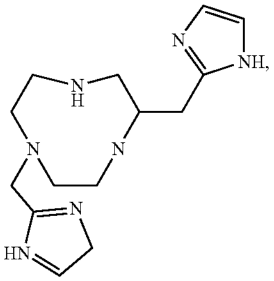
TBI
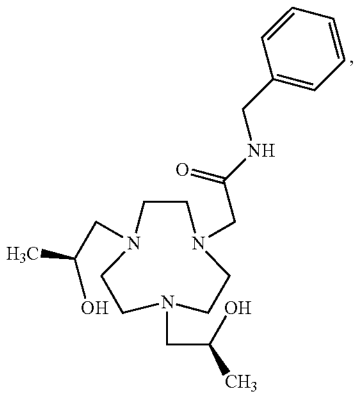
TOPID -continued
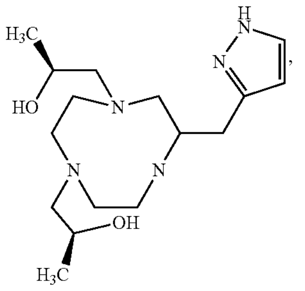
and
TOPy
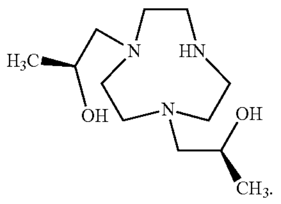
TON
Statement 14. A macrocyclic compound or complex according to any one of Statements 2-13, where the macrocyclic compound has one of the following structures:
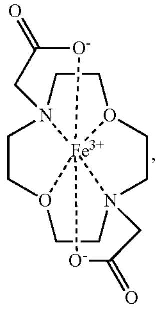
Fe(NODAC)
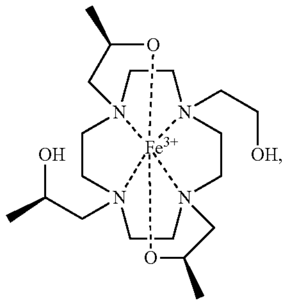
Fe(STHP)
-continued
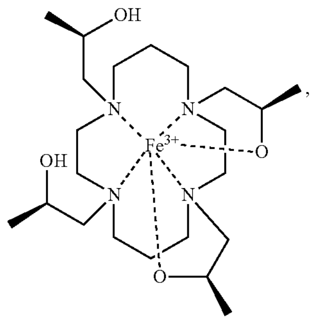
Fe(STHC)
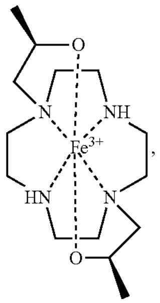
Fe(GUAC)
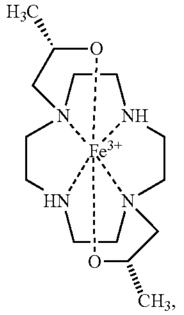
Fe(GUAC)
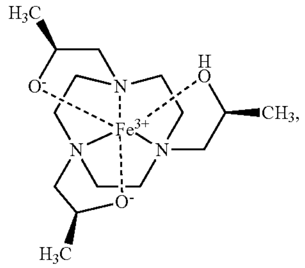
Fe(TACO)

-continued
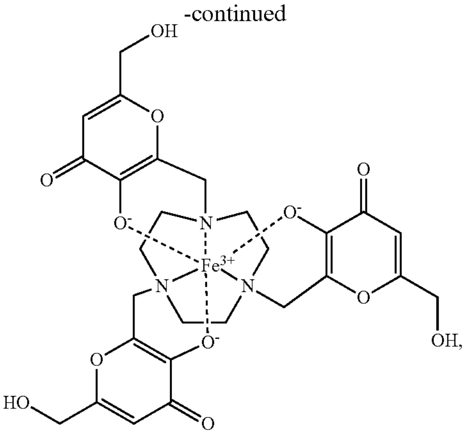
Fe(NOKA)
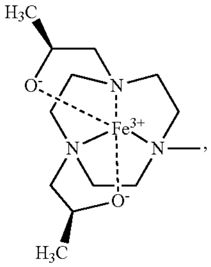
Fe(TOM)
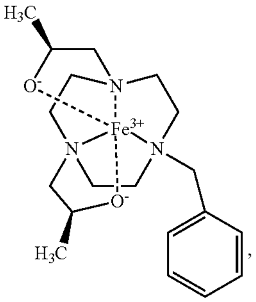
Fe(TOB)
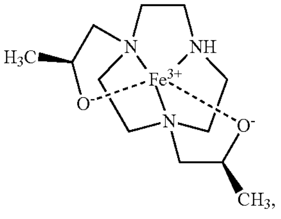
Fe(TON)
-continued
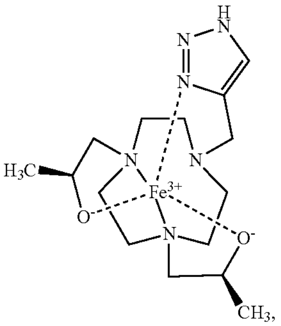
Fe(ToTz)
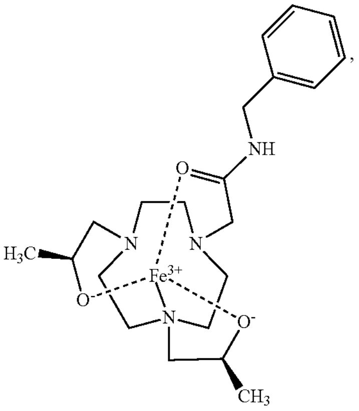
Fe(AmBz)
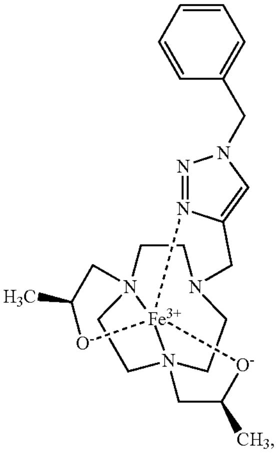
and
Fe(ToTzB)

-continued

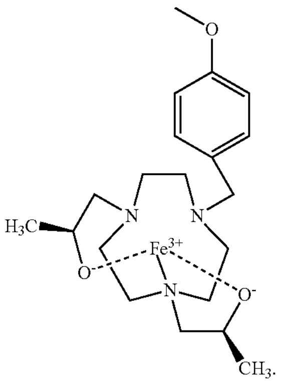

Fe(MeoxyBz)

Statement 15. A compound comprising one or more macrocyclic groups (e.g., macrocyclic complex groups) tethered together (e.g., covalently linked) by a linker group or a polymer, a dendrimer, a protein, or a peptide, comprising one or more pendant macrocyclic groups (e.g., macrocyclic complex groups) covalently linked (e.g., bound) to the polymer, the dendrimer, the protein, or the peptide, where each of the individual macrocyclic groups (e.g., macrocyclic complex groups) are derived from a macrocyclic compound of the present disclosure (e.g., a macrocyclic compound according to any one of Statements 1-14).

Statement 16. A compound or polymer according to Statement 15, where the compound has the following structure:

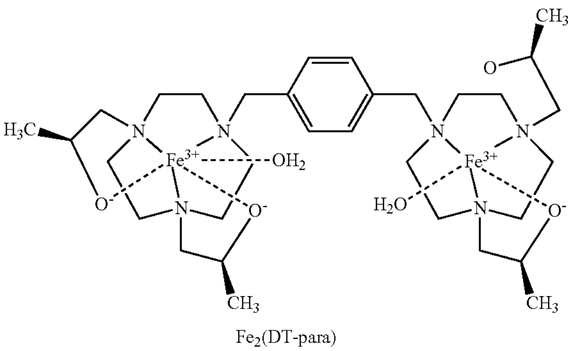

$Fe_2$(DT-para)

-continued

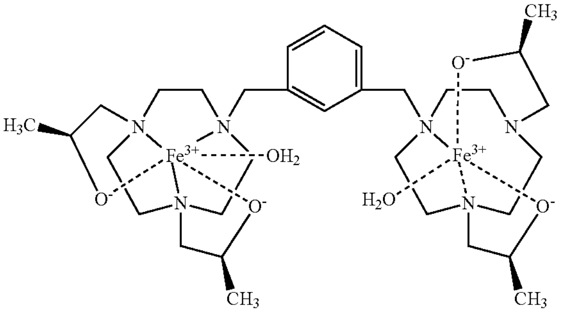

$Fe_2$(DT-meta)

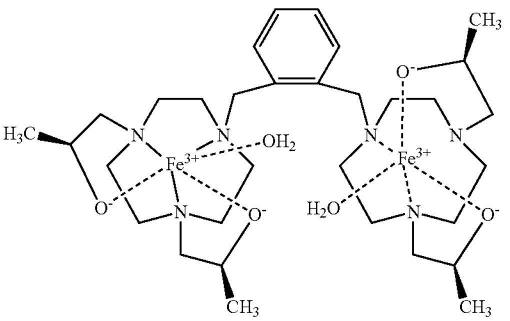

$Fe_2$(DT-ortho)

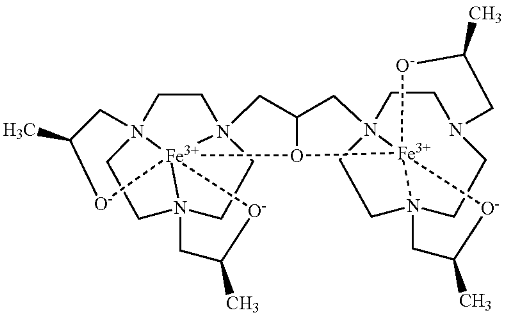

$Fe_2$(TONO)

Statement 17. A compound or polymer according to Statement 15, where the polymer has the following structure:

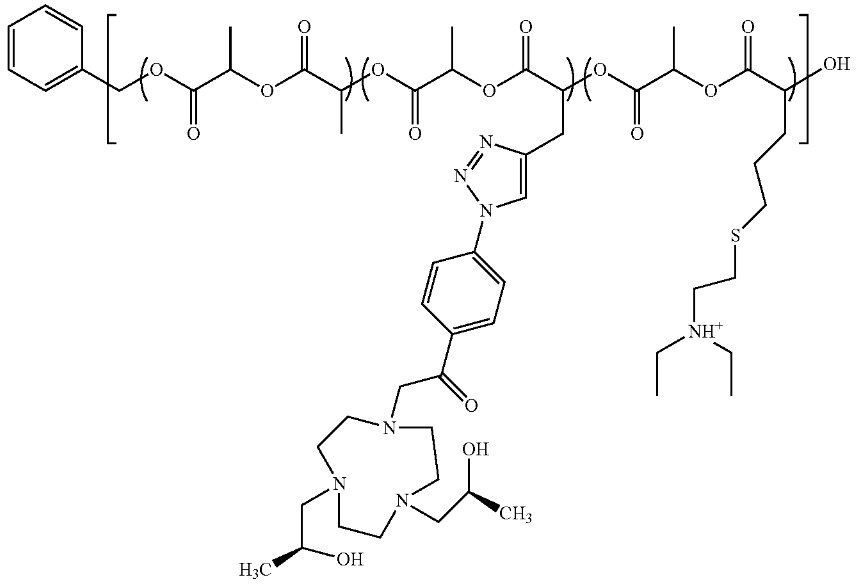

Statement 18. A composition comprising one or more macrocyclic compound and/or one or more macrocyclic complex of the present disclosure (e.g., one or more macrocyclic compound according to Statements 1 and/or one or more macrocyclic complex according to any one of Statements 2-14) and/or one or more compound of the present disclosure (e.g., a compound according to any one of Statements 15-17) and a pharmaceutically acceptable carrier.

Statement 19. A composition according to Statement 18, where the composition further comprises human serum albumin and/or meglumine.

Statement 20. A method to obtain an image of at least a portion of a cell, organ, vasculature or tissue comprising: contacting the cell, organ, vasculature, or tissue with one or more macrocyclic compound and/or one or more macrocyclic complex of the present disclosure (e.g., one or more macrocyclic compound according to Statement 1 and/or one or more macrocyclic complex according to any one of Statements 2-14) and/or one or more compound of the present disclosure (e.g., a compound according to any one of Statements 15-17), and imaging at least a portion of the cell, organ, vasculature, or tissue to obtain an image of the portion of a cell, organ, vasculature, or tissue, where the image is obtained by using magnetic resonance.

Statement 21. A method according to Statement 20, where the cell, organ, vasculature, or tissue is part of an individual.

Statement 22. A method according to Statement 20 or 21, where the image is obtained using magnetic resonance imaging (MM).

Statement 23. A method according to any one of Statements 20-22, where the macrocyclic compound(s) and/or compound(s) is/are a $T_1$ agent or $T_1$ agents.

EXPERIMENTAL DETAILS

General procedure for synthesis of disubstituted TACN (1,4,7-triazacyclononane) ligands. Other synthetic procedures are shown in FIGS. 27, 28, 29, 30.

TACN-Protection: N,N-Dimethylformamide dimethylacetal (304 mg, 2.55 mmol, 1.1 equiv) was added to a solution of TACN (300 mg, 2.32 mmol) in chloroform (2 mL) and toluene (8 mL). The solution was stirred at room temperature for 12 hours. The solvent was evaporated under reduced pressure to yield an oily product. This crude product was used in the next synthesis without further purification. ESI-MS (m/z) of 1,4,7-triazatricyclo[5.2.1.04,10]decane (tacn orthoamide), calculated: 140.1 [M+H+] (100%).

Protected TACN alkylations. The crude TACN-orthoamide product isolated above was dissolved in dry THF (5 mL) and Ar(g) was bubbled through this solution for 5 minutes to produce an inert atmosphere. Halogenated reagents were added to this solution either directly or pre-dissolved in 1 mL dry THF. These reagents may include one of the following including: benzyl bromide, iodomethane, propargyl bromide, 1-Bromo-2-(2-methoxy-ethoxy)ethane, 4-(bromomethyl)-1,1'-biphenyl, ethyl 4-(bromomethyl)-benzoate or benzyl chloromethyl ether. Solutions were stirred for 1-7 days depending on the chosen reagent. The product precipitated from solution, which was then filtered and washed with diethyl ether (3×15 mL). If the product did not precipitate, such as is the case with 1-Bromo-2-(2-methoxy-ethoxy)ethane, solvent was removed under pressure to yield a crude product which can be utilized in the next synthesis without further purification.

Deprotection of alkylated protected TACN derivatives. Products of the previous synthesis were dissolved in 12 M HCl/MeOH 1:1 solution or KOH solution. The solution was refluxed overnight. After the solution was allowed to cool to room temperature, purification of products was carried out by one of two methods. To isolate the free-base form of the product, the pH of the solution was adjusted to 12 (in the case of KOH deprotection, no adjustment is needed) and product was extracted using chloroform (3×10 mL). Chloroform layers were combined and solvent removed under pressure. To isolate the product as HCl salt, solvent was evaporated under pressure and crude HCl salt was dissolved in ethanol (5 mL). 12 M HCl was added to the solution (1-2 mL) and solvent was evaporated under pressure to yield product.

Propyl alcohol donor group addition. One of the mono-alkylated products (free base form) described in the paragraph above was dissolved in ethanol, water, or an ethanol/ water mixture. (S)-(−) propylene oxide was added to the solution and stirred for 12 hours. Solvent was removed under pressure to yield the crude product. Purification of final ligands was performed using column chromatography, chloroform/methanol 100/0 to 50/50. Alternatively, (R)-(+) propylene oxide may be used instead of (S)-(−) propylene oxide to give the macrocycle with pendent groups of an opposite chirality.

General Procedure for forming Fe(III) TACN derivatives. The ligand described immediately above was dissolved in ethanol and $FeCl_2 \cdot 4H_2O$ was added to the solution. The solution was heated to 40° C. and allowed to stir for 1 hour. After the solution was allowed to cool to RT, diethyl ether was added until product precipitates. The product was filtered and washed with diethyl ether (3×20 mL). Alternatively, an equivalent of $FeCl_3$, was added to a stirred solution of the ligand in acetonitrile along with two equivalents of trimethylamine. Diethyl ether was added until the product precipitated.

SPECIFIC EXAMPLES

Synthesis of TOB ligand. Synthesis of 1,1'-(7-benzyl-1,4,7-triazonane-1,4-diyl)bis(propan-2-ol). In a 10 mL round-bottom flask, 1-Benzyl[1,4,7]-triazacyclononane (0.127 g, 0.5795 mmol) was dissolved in 5.0 mL absolute ethanol. To this solution was added (S)-(−)-propylene oxide (2.9 mmol, 5.0 eq). After the solution was stirred at RT for 2 days the solvent was removed under pressure to yield an oily crude product. The crude product was then dissolved in diethyl ether and precipitate removed through filtration. The filtrate was dried under pressure to yield 1,1'-(7-benzyl-1,4,7-triazonane-1,4-diyl)bis(propan-2-ol) as a clear oil (0.1657 g, 0.4942 mmol, 85%). ESI-MS: m/z=336.3 [M+H]+. $^1H$ NMR (400 MHz, CD3OD); δ 1.09 (d, 6H, J=6), 2.25-2.94 (m, 16H), 3.55-3.83 (m, 4H), 7.15-7.44 (m, 5H). $^{13}C$ NMR (75 MHz, $CDCl_3$): δ 19.9, 54.4, 55.2, 62.7, 63.8, 66.4, 127.1, 128.2, 129.6, 139. To the TOB ligand in acetonitrile was added one equivalent of $FeCl_3$, two equivalents of triethylylamine and the reaction was stirred overnight. Diethyl ether was added until the product precipitated. The precipitate was isolated and washed with diethyl ether and dried under vacuum. Yield 35%. ESI-MS: m/z=389.2 $[M]^+$, 425.0 $[M+H+Cl]^+$. Wash with diethyl ether. Dry under vacuum. Yield 35%. ESI-MS: m/z=389.2 $[M]^+$, 425.0 $[M+H+Cl]^+$.

Synthesis of TON ligand. Benzyl deprotection was performed by Pd/C (10%) catalyst. 30 mg Pd/C (10%) in 5 mL methanol 1 mL water was added into the ligand solution. The air was removed from the solution under argon gas for 30 minutes. Catalytic hydrogenation was performed for 3 days with vigorous shaking on a Parr hydrogenator at room temperature under hydrogen atmosphere. The mixture was filtrated over celite to remove the catalyst from the reaction solution and (1,4,7-triazonane-1,4-diyl)bis(propan-2-ol) (TON ligand) was obtained. ESI-MS (m/z), calculated: 246.3 $[M+H^{30}]$ (100%). The solution was dried by placing flask on a rotoevaporator.

Synthesis of NODAC (2,2'-(1,7-dioxa-4,10-diazacyclododecane-4,10-diyl) diacetic acid). A mass of 0.122 grams (0.701 mmol) of 4,10-Diaza-12-crown 4-ether and 0.0987 grams (0.714 mmol) of potassium carbonate were added into 5 mL of acetonitrile and stirred a round bottom flask at room temperature. To the stirring mixture, 0.2848 grams (1.46 mmol) of tert-butyl bromoacetate was slowly added by pipette. The solution continued to stir for four hours. Next the solution was filtered, removing any undissolved potassium carbonate and the filtrate was put under vacuum to remove the solvent, leaving behind a yellow oil. The oil was dissolved in 3 mL of dichloromethane and 1 mL of trifluoroacetic acid and allowed to stir at room temperature overnight. Next, the solvent was removed by vacuum, and the remaining white solid was washed in a 50:50 ether-methanol mixture, and filtered for collection. The yield of the product was 0.1822 grams (0.628 mmol, 89.5%). $^1H$ NMR (300 MHz) ppm: 4.004 (s, pendent $CH_2$, 4H), 3.760 (t, O—$CH_2$, 8H), 3.535 (s, ring N—$CH_2$, 8H). ESI-MS:m/z=347.2 $[M+2Na—H)]^+$, 375.0 $[M+2Na+K—2H+]^+$).

Synthesis of Fe(III)NODAC complex. A mass of 0.1108 grams (0.381 mmol) of 2,2'-(1,7-dioxa-4,10-diazacyclododecane-4,10-diyl) diacetic acid was dissolved in 3 mL of water and stirred into solution, adding small aliquots of a 1 M NaOH until a pH of 6 was reached. Next, 0.1028 grams (0.380 mmol) of iron(III)chloride hexahydrate was added to the solution and stirred overnight. Acetonitrile was added into the solution and centrifuged to form a precipitate. The precipitate was repeatedly washed and centrifuged with ether to remove water, then allowed to dry under vacuum. A red solid was obtained. Yield, 0.0601 grams of [Fe(III){NODAC)OH] was obtained (0.139 mmol, 36.6%). ESI-MS: m/z=384.1 $([M+NaOH—2H]^+)$.

Synthesis of NODOH (2,2'-(1,7-dioxa-4,10-diazacyclododecane-4,10-diyl) bis(propan-2-ol). A mass of 102.6 mg (0.589 mmol) of 4,10-Diaza-12-crown 4-ether was dissolved in 4 mL ethanol and stirred in a round bottom flask. A large excess of S-propylene oxide (0.400 mL, 0.332 g, 5.716 mmol) was added to the solution and stirred for three days at room temperature. Solvent was removed under vacuum to yield a yellow oil product (0.0603 g, 0.207 mmol, 35.1%). $^1H$ NMR (300 MHz) ppm: 3.75 (m, CH, 2H), 3.48 and 3.33 (t, O—$CH_2$, 8H), 2.69 and 2.49 (t, N—$CH_2$ (ring), 8H), 2.34 and 3.24 (t, N—$CH_2$ pendent, 4H), 1.00 (d, CH3, 6H). ESI-MS:m/z=291.3 [M+H]+, 313.3 [M+Na]+.

Synthesis of Fe(NODOH). A mass of 0.0796 grams of NODOH was dissolved in ethanol and added to a round bottom flask. Next 0.0548 grams of $FeCl_2$ tetrahydrate was added to the flask and stirred in solution overnight. The solvent was removed under vacuum, then the complex was allowed to oxidize by exposure to air.

Synthesis of TOBA ligand. TON ligand was dissolved in 12 mL acetonitrile in the 25 mL round bottom flask. Then, 0.189 g ethyl-4-(bromomethyl) benzoate (0.776 mmol) and 0.100 g N, N-Diisopropylethylamine (DIEA) (0.774 mmol) was added to the flask. The solution was stirred for 3 days at room temperature. ESI-MS (m/z), calculated: 408.3 $[M+H^+]$ (100%). Ester deprotection was accomplished in 0.150 M NaOH ethanol solution. HCl was added for pH adjustment to 7. The resulting NaCl salt was filtered off. Chloroform solvent was used to wash the ligand (TOBA). ESI-MS (m/z), calculated: 380. 3 $[M+H^+]$ (100%).

Synthesis of the Fe(TOBA) complex. In a 25 mL round bottom flask with a stir bar, TOBA ligand (0.1 g, 0.263 mmol) and 10 mL ethanol were added. $FeCl_2 \cdot 4H_2O$ (0.0523 g, 0.263 mmol) was dissolved in 5 mL ethanol and added into the flask. The solution was stirred at room temperature for 2 days. A yellow precipitate was obtained after addition of diethylether. The solution was filtered and washed with diethyl ether. The yellow powder was obtained by removing the solvent through rotary evaporation. ESI-MS (m/z), calculated: 433.2 $[M+H^+]$ (100%).

Synthesis of the TOPID ligand. TON ligand was dissolved in 12 mL acetonitrile in the 25 mL round bottom flask. 0.118 g 3-bromopropionamide (0.776 mmol) and 0.100 g N, N-Diisopropylethylamine (DIEA) (0.776 mmol) was added to the flask. The solution was stirred for 3 days at room temperature. ESI-MS (m/z), calculated: 317.3 [$M+H^+$] (40%), 339.2 [$M+Na^+$] (100%). Purification was applied by using basic alumina column and dichloromethane and methanol solvents.

DT-Meta. To a 25 mL round bottom flask with gas inlet and stir bar was added 0.100 g TACN (0.774 mmol) in 4 mL toluene 1 mL chloroform solution. 0.0920 g N,N-dimethylformamide dimethylacetal (0.774 mmol) was added to the flask. The solution was stirred for 24 hours at room temperature. ESI-MS (m/z) of 1,4,7-triazatricyclo[5.2.1.$0^{4,10}$]decane (tacn orthoamide), calculated: 140.1 [$M+H^+$] (100%). The solution was dried by placing flask on a rotary evaporator. The dried tacn orthoamide and 15 mL dry acetonitrile was added in 50 mL 3-necked round bottom flask equipped with a magnet stir bar, reflux condenser, gas inlet tube and addition funnel. 0.100 g α, α'-Dibromo-m-xylene (0.384 mmol) in 10 ml dry acetonitrile solution was added into the flask by dropwise addition with an addition funnel for 30 min. The solution was heated to reflux for 2 hours and was stirred overnight at room temperature. A white-beige color precipitate was collected by suction filtration method and washed with dry acetonitrile (5 mL) and diethyl ether (5 mL). 6 mL methanol and 6 mL 12 M HCl was added to the precipitate in the flask for the deprotection process. The solution was heated to reflux for 4 hours. After the solution was cooled to room temperature, NaOH pellets were added to bring the pH of the solution to 8. Then the solution was filtered to remove NaCl salt precipitate and extracted with chloroform (3×60 mL). ESI-MS (m/z), calculated: 361.4 [$M+H^+$] (100%). The solution was subjected to rotoevaporation and dissolved in 15 mL ethanol in 25 mL round bottom flask with 0.202 g S-propylene oxide (3.483 mmol) and stirred for 24 hours at room temperature. The solvent was removed from the final solution and the sample was dried on a Schlenk line under vacuum. The yield was calculated as 58%. ESI-MS (m/z), calculated: 593.6 [$M+H^{30}$] (45%), 615.6 [$M+Na^+$] (100%) and 297.5 [($M+Na^+$] (45%). $^1$H NMR ($CDCl_3$, 25° C., 500 MHz): δ 1.20 (12H, $CH_3$), 2.30/2.82 (8H, $N\underline{CH_2}CH$), 2.60 (24H, $CH_2CH_2$), 3.60 (4H, $\underline{CH}OH$), 3.75 (4H, $N\underline{CH_2}C$) and 7.28 (4H, CH in benzene ring).

Fe(III) complexes of DT-ortho, DT-meta, DT-para. In a 25 mL round bottom flask with a stir bar the ligand (DT) (0.1 g, 0.168 mmol) and 10 mL ethanol were added. FeCl2·4H2O (0.0334 g, 0.168 mmol) was dissolved in 2 ml ethanol and added into the flask. The solution was heated to 60° C. for 1 hour and cooled to room temperature. A yellow precipitate was obtained after addition of diethylether. The solution was filtered and washed with diethyl ether. The yellow powder was obtained by removing the solvent through rotoevaporation. ESI-MS (m/z), calculated: 350.4 [M/2] (100%). Effective magnetic moments measured in aqueous solution by using Evans method gave a $\mu_{eff}$ of 6.4 BM for the $Fe_2$(DT-meta) complex and 8.2 BM for the $Fe_2$(DT-ortho) complex.

TON macrocyclic compound. To a 25 mL round bottom flask with gas inlet and stir bar was added 0.100 g TACN (0.774 mmol) in 4 mL toluene 1 mL chloroform solution. 0.0920 g N,N-dimethylformamide dimethylacetal (0.774 mmol) was added to the flask. The solution was stirred for 24 hours at room temperature. ESI-MS (m/z) of 1,4,7-triazatricyclo[5.2.1.04,10]decane (tacn orthoamide), calculated: 140.1 [M+H+] (100%). The solution was dried by placing flask on a rotoevaporator. The dried tacn orthoamide and 15 mL dry tetrahydrofuran (THF) was added in 50 mL 3-necked round bottom flask equipped with a magnet stir bar, reflux condenser, gas inlet tube and addition funnel. 92.2 μL benzyl bromide (0.774 mmol) was added into the flask. the solution was stirred overnight at room temperature. A white-beige color precipitate was collected by suction filtration method and washed with dry THF (10 mL) and diethyl ether (10 mL). 7 mL methanol and 7 mL 12 M HCl was added to the precipitate in the flask for the deprotection process. The solution was heated to reflux for 4 hours. After the solution was cooled to room temperature, NaOH pellets were added to bring the pH of the solution to 8. Then the solution was filtered to remove NaCl salt precipitate and extracted with chloroform (3×60 mL). ESI-MS (m/z), calculated: 220.3[$M+H^+$](100%). The solution was subjected to rotoevaporation and dissolved in 15 mL ethanol in 25 mL round bottom flask with 0.225 g S-propylene oxide (3.870 mmol) and stirred for 24 hours at room temperature. The solution was rotoevaporated and dried on a Schlenk line under vacuum and dissolved in 10 mL methanol. %. ESI-MS (m/z), calculated: 336.3 [$M+H^+$] (100%). Benzyl deprotection was performed by Pd/C (10%) catalyst. 30 mg Pd/C (10%) in 5 mL methanol 1 mL water was added into the ligand solution. The air was removed from the solution under argon gas for 30 minutes. Catalytic hydrogenation was performed for 3 days with vigorously stirring at room temperature under hydrogen atmosphere. The mixture was filtrated over celite to remove the catalyst from the reaction solution and (1,4,7-triazonane-1,4-diyl)bis(propan-2-ol) (TON ligand) was obtained. ESI-MS (m/z), calculated: 246.3 [$M+H^+$] (100%). The solution was dried by placing flask on a rotoevaporator.

TONO. The TON ligand was dissolved in 12 mL acetonitrile in the 25 mL round bottom flask. 0.0499 g 1,3-Dichloro-2-propanol (0.387 mmol) and 0.100 g N, N-Diisopropylethylamine (DIEA) (0.774 mmol) was added to the flask. The solution was stirred for 2 days at 50° C. TONO ligand was purified by using basic alumina column with dichloromethane and methanol solvents. ESI-MS (m/z), calculated: 547.5 [$M+H^+$] (18%), 569.5 [$M+Na^+$](100%), 274.5[($M+H^+$)/2] (10%).

ICP-MS. Iron concentration was determined using Thermo X-Series 2 ICP-MS. All samples were diluted (1 μM) with 2% nitric acid in 10 mL total water solution and were decomposed by heating (90° C.) for 24 hours. A linear calibration curve for iron metal ranging from 0.1 ppb to 250 ppb was generated daily for the quantification. Samples were digested in nitric acid over a period of four days and the iron concentration determined.

Magnetic moments. Samples for studies of magnetic moment by using the Evans method were prepared using a coaxial NMR insert which contained the diamagnetic standard of 5% t-butanol in $D_2O$. The outer 5 mm NMR tube contained 5 mM paramagnetic complex with fixed concentrations; 4 mM, 8 mM, 40 mM, and 70 mM in presence of 5% t-butanol. The effective magnetic moment ($\mu_{eff}$, BM) was calculated by using a modified Evans method for small molecules at 298 K (T).

pH Potentiometric Titrations. Solutions containing 1-1.5 mM Fe(III) complex in 100 mM NaCl were titrated with NaOH under Ar at 25° C. HYPERQUAD 2013 Version 6.0.1 program was used to determine the protonation states and the $pK_a$ values of the complex from the pH data. A speciation diagram was obtained by using the HySS Version 4.0.31 program.

Preparation of Samples for Phantom MR Imaging: Samples for phantom imaging experiments contained 50-500 μM complex, 20 mM HEPES and 100 mM NaCl. For samples containing Human Serum Albumin (HSA), 35 mg of HSA was added to these solutions. The pH of all solutions was adjusted to 7.0.

Phantom (in vitro) imaging at 4.7 T. MRI acquisitions were performed using a General Electric 4.7T/33 cm horizontal bore magnet (GE NMR instruments, Fremont, CA) incorporating AVANCE digital electronics (Bruker BioSpec platform with ParaVision v 3.0.2 acquisition software, Bruker Medical, Billerica, MA). Each complex was diluted with HEPES in 100 mM NaCl (pH 7.4) to a concentration ranging from 0.0.5 mM to 400 mM and imaged at 25° C. $T_1$ relaxation rates ($R_1$) were acquired utilizing a saturation recovery, spin-echo (SE) sequence with a fixed echo time (TE), 10 ms and repetition times (TR) ranging from 75 to 8000 ms. Signal intensities at each repetition time were sampled by taking the mean intensity within regions of interest (ROI's) using commercially available image processing software (Analyze 7.0, AnalyzeDirect, Overland, KS), and R1 and SMAX were calculated by nonlinear fitting of the equation using Matlab's Curve Fitting Toolbox (Matlab 7.0, MathWorks Inc., Natick, MA). The $T_1$ relaxivity for each complex was then determined by obtaining the slope of the compound's molar concentration vs $R_1$ via linear regression fitting of the data. Similarly, $T_2$ relaxation rates ($R_2$) were acquired using a multiecho, Carr-Purcell-Meiboom Gill (CPMG) SE sequence with a fixed TR of 2500 ms and TE times ranging from 15 to 300 ms, NEX) 2. $R_2$ and SMAX were calculated as described above using the equation As before, the $T_2$ relaxivity was determined by obtaining the slope of concentration vs $R_2$ via linear regression fitting of the data.

In vivo imaging in mice. Efficacy of the Fe(III) complexes for in vivo contrast enhancement was studied on at 4.7 T Bruker preclinical MRI in a mouse model (BABC/cJ, Jackson Laboratory). Sealed phantoms were included for imaging sessions for signal normalization. Prior to administration of contrast agents, scans were acquired to serve as baseline values of enhancement. Two scan protocols were used: (1) a $T_1$-weighted, 3D, spoiled-gradient echo scan covering the mouse from thorax to tail to determine signal enhancement and (2) inversion-recovery, steady state free precession scans (IR-SSFP) to measure $T_1$ rates in the blood (inferior vena cava), kidneys, liver, gall bladder and back muscle. Compounds were injected intravenously via tail vein at a dose of 50 μmol [Fe]/kg and MR data were acquired continuously for up to 1 hour after injection to study distribution and clearance kinetics. Thus, 0.2 mL of a 6 mM stock solution was injected into the mouse or 0.05 mmol/Kg. Additional scans were acquired at 3 and 6 hours post-injection to characterize slower clearance rates by the biliary system. The FDA-approved MM contrast agent gadopentetate dimeglumine (Gd-DTPA, Magnevist®) was injected into a separate cohort of mice at 50 μmol [Gd]/kg for comparison. Data is shown in FIGS. 15, 16, 17, 18, and 19. For SPGR datasets, signal intensities were normalized to the phantoms and signal increase for each organ was measured, as well as an increase in contrast-to-noise ratios as compared to back muscle. Fe(III) concentrations were estimated by calculating the increase in $T_1$ rates and dividing by the compound's relaxivity value as determined in vitro. The data showed that Fe(TOB) had greater contrast than Gd(DTPA) in kidney and liver over 30 minutes. Fe(NOKA) showed less contrast than either Gd(DTPA) or Fe(TOB) in kidneys and was roughly equivalent contrast to that of Gd(DTPA) in liver (FIG. 18).

The invention claimed is:

1. A macrocyclic core having the following structure:

(I)

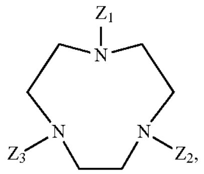

(II)

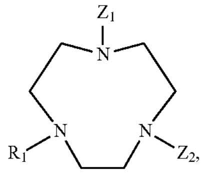

(III)

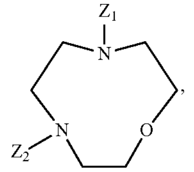

, or

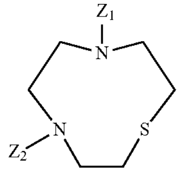

and $Z_1$, $Z_2$, and $Z_3$ are each independently H or one or more of the following pendant groups:

2

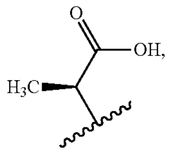

2'

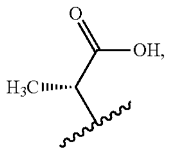

6

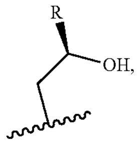

6'

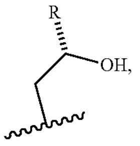

7

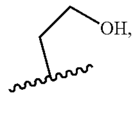

-continued

8

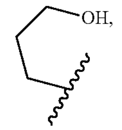

15

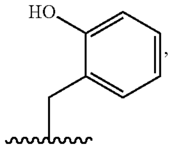

16

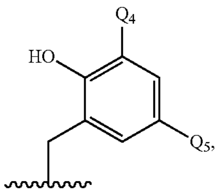

17

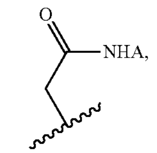

18

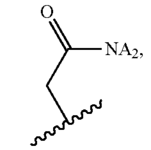

19

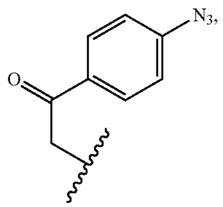

or a deprotonated analog thereof or a stereoisomer thereof, wherein R is methyl, and Ri is independently a substituted or unsubstituted aryl, substituted or unsubstituted heteroaryl, or substituted or unsubstituted alkyl group, and $R_1$ is not pendant donors;

$Q_4$ and $Q_5$ are each independently H, $OCH_3$, $CO_2H$, or substituted or unsubstituted alkyl groups of linear or branched structures, A is a substituted or unsubstituted alkyl group of linear or branched structure with $C_1$ to $C_{12}$ or is a substituted or unsubstituted aryl group or an amino acid, or a salt, a partial salt, a hydrate, a polymorph, or a stereoisomer thereof, wherein the macrocyclic core has structure II or III, $Z_1$ and $Z_2$ are each independently a pendant group;

wherein for all structures I, II, and III, each of $Z_1$, $Z_2$, and $Z_3$, as applicable, are selected independently of each other, and at least one of R, $Z_1$, $Z_2$, and $Z_3$ is different than the remaining R, $Z_1$, $Z_2$, and $Z_3$.

2. The macrocyclic core of claim 1, wherein the macrocyclic core has the following structure:

(I)

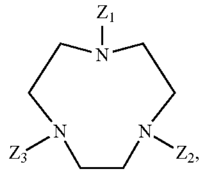

(II)

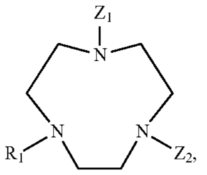

and at least one anionic pendant group.

3. The macrocyclic core of claim 1, wherein the macrocyclic core has the following structure:

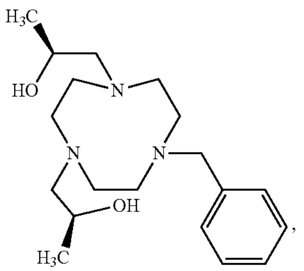

TOB

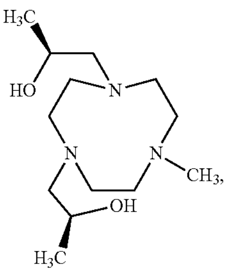

TOM

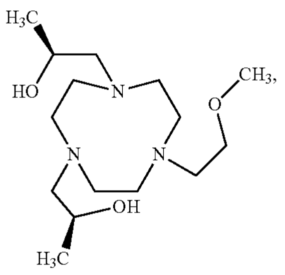

TOP

-continued
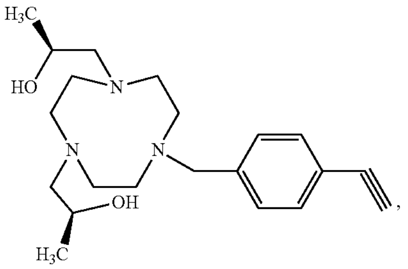
TOBAC
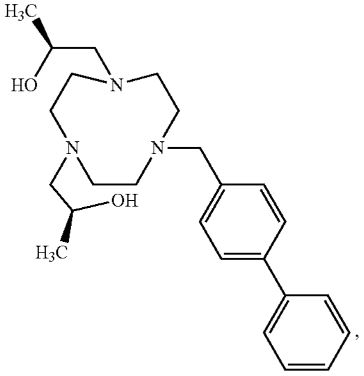
TOBI
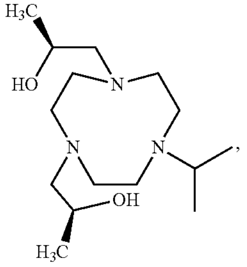
TOPI
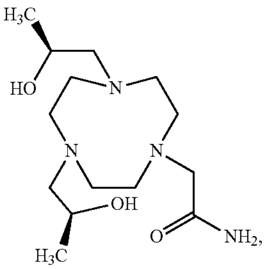
TOA
-continued
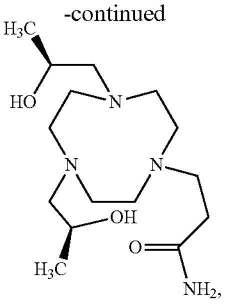
TOPID
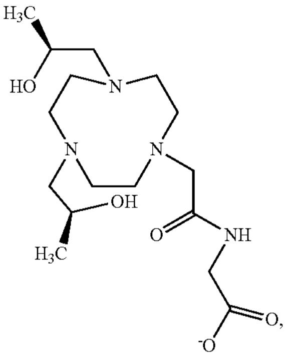
TOAG
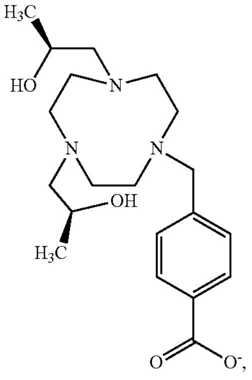
TOBA
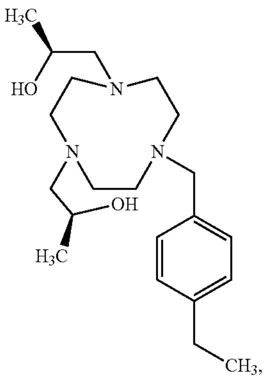
MeoxyBz -continued
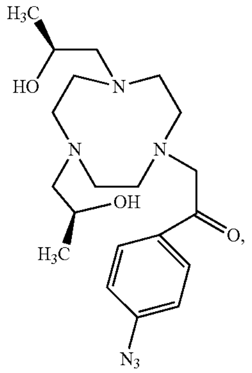
TOCBA
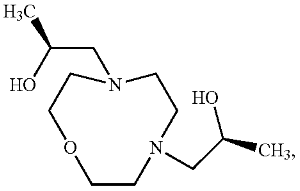
(HPN2O)
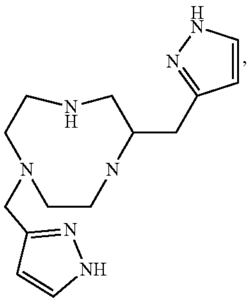
TBP
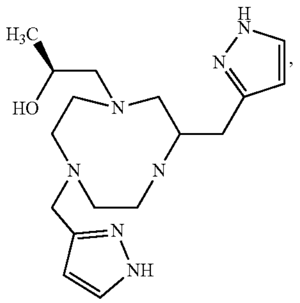
TOBP
-continued
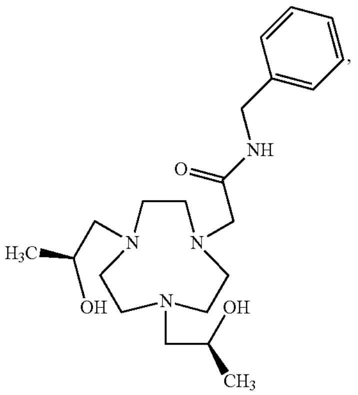
TOPID
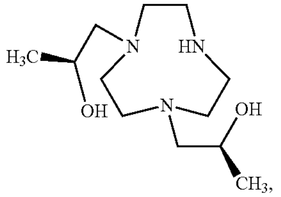
TON
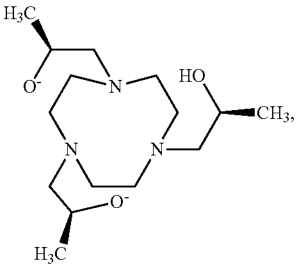
TACO
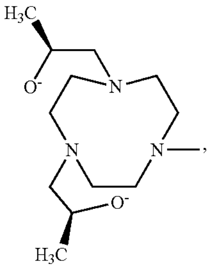
TOM
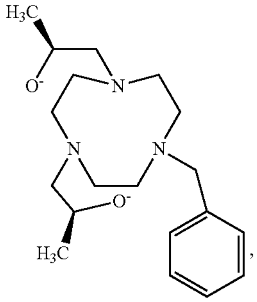
TOB -continued
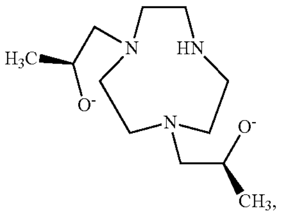
TON
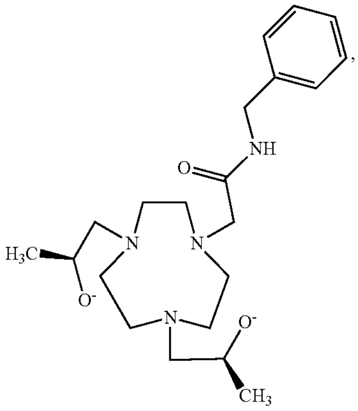
, or
AmBz
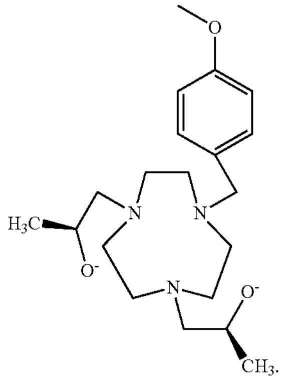
MeoxyBz
4. A macrocyclic core having the following structure:
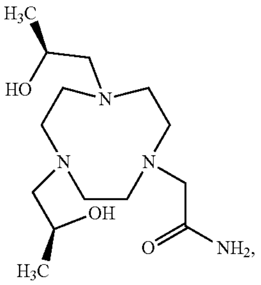
TOA
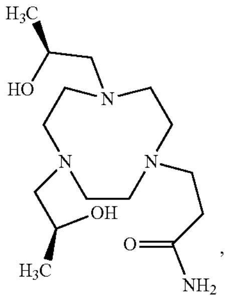
,
TOPID
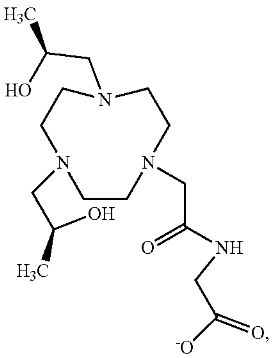
TOAG
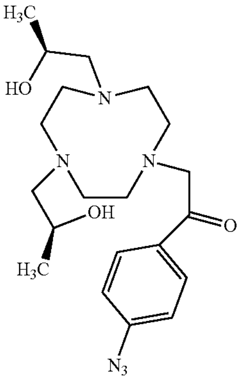
, or
TOCBA
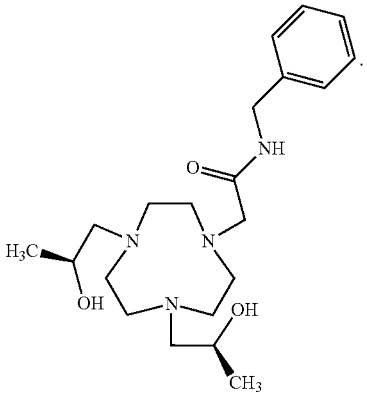
TOPID
* * * * *